United States Patent
Kipps et al.

(10) Patent No.: US 11,883,492 B2
(45) Date of Patent: Jan. 30, 2024

(54) COMBINATION TREATMENT OF CHEMORESISTANT CANCERS

(71) Applicant: THE REGENTS OF THE UNIVERSITY OF CALIFORNIA, Oakland, CA (US)

(72) Inventors: Thomas Kipps, San Diego, CA (US); Suping Zhang, La Jolla, CA (US); Emanuela M. Ghia, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 65 days.

(21) Appl. No.: 16/979,469

(22) PCT Filed: Mar. 11, 2019

(86) PCT No.: PCT/US2019/021694
§ 371 (c)(1),
(2) Date: Sep. 9, 2020

(87) PCT Pub. No.: WO2019/173843
PCT Pub. Date: Sep. 12, 2019

(65) Prior Publication Data
US 2021/0085786 A1 Mar. 25, 2021

Related U.S. Application Data

(60) Provisional application No. 62/641,035, filed on Mar. 9, 2018.

(51) Int. Cl.
| | |
|---|---|
| *A61K 39/395* | (2006.01) |
| *A61K 9/00* | (2006.01) |
| *A61K 39/00* | (2006.01) |
| *A61P 35/00* | (2006.01) |
| *C07K 16/28* | (2006.01) |
| *A61K 31/337* | (2006.01) |

(52) U.S. Cl.
CPC ........ *A61K 39/3955* (2013.01); *A61K 9/0019* (2013.01); *A61K 31/337* (2013.01); *A61P 35/00* (2018.01); *C07K 16/2803* (2013.01); *A61K 2039/505* (2013.01); *A61K 2039/54* (2013.01); *A61K 2039/545* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 9,217,040 B2 * | 12/2015 | Kipps | G01N 33/6854 |
| 2017/0368173 A1 | 12/2017 | Kipps et al. | |
| 2018/0066063 A1 | 3/2018 | Kipps et al. | |

FOREIGN PATENT DOCUMENTS

| | | | | |
|---|---|---|---|---|
| WO | WO-2016187220 A2 * | 11/2016 | | A61K 38/05 |

OTHER PUBLICATIONS

NCT02776917 (Year: 2016).*
NCT02776917 (First published May 17, 2016), (Year: 206).*
Zhang et al.(2016) (Abstract 1193: Treatment of breast cancer xenografts with paclitaxel enriches for cancer stem cells that can be targeted by a ROR1-specific antibody, Cancer Research, 76), (Year: 2016).*
Zhang et al.(2012) (ROR1 is expressed in Human Breast Cancer and Associated with Enhanced Tumor-Cell Growth, PLoS One, vol. 7, 2012) (Year: 2012).*
Cabanes et al.(Comparative in vivo studies with paclitaxel and liposome-encapsulated paclitaxel, International Journal of Oncology, pp. 1035-1075, 1998) (Year: 1998).*
Extended European Search Report dated Nov. 4, 2021, for EP Patent Application No. 19764748.0, 8 pages.
International Search Report dated Jul. 19, 2019, for PCT Application No. PCT/US2019/021694, filed Mar. 11, 2019, 5 pages.
Written Opinion dated Jul. 19, 2019, for PCT Application No. PCT/US2019/021694, filed Mar. 11, 2019, 10 pages.
Zhang, S. et al. "Breast Cancer Initiating Cells Express Functional ROR1, Which Can Be Targeted By Cirmtuzumab to Potentially Mitigate the Risk of Relapse After Therapy," Poster in 2017 San Antonio Breast Cancer Symposium. Dec. 5-9, 2017 [Retrieved on Jun. 4, 2019]. Retrieved from the Internet: <URL: http://sabcsl7.posterview.com/nosl/p/P1-09-07>; 4 pages.
Zhang, S. et al. (Jan. 22, 2019, e-published Jan. 8, 2019). "Inhibition of chemotherapy resistant breast cancer stem cells by a ROR1 specific antibody," *PNAS USA* 116(4):1370-1377.

* cited by examiner

*Primary Examiner* — Laura B Goddard
*Assistant Examiner* — Sarah A Alsomairy
(74) *Attorney, Agent, or Firm* — MINTZ, LEVIN, COHN, FERRIS, GLOVSKY AND POPEO, P.C.

(57) ABSTRACT

There are provided, inter alia, compositions and methods for treatment of chemoresistant cancer (breast cancer). The methods include administering to a subject in need a therapeutically effective amount of a chemotherapeutic agent and a ROR-1 antagonist. Further provided are pharmaceutical compositions including chemotherapeutic agent, ROR-1 antagonist and a pharmaceutically acceptable excipient. In embodiments, the chemotherapeutic agent is paclitaxel and the ROR-1 antagonist is cirmtuzumab.

15 Claims, 33 Drawing Sheets

Specification includes a Sequence Listing.

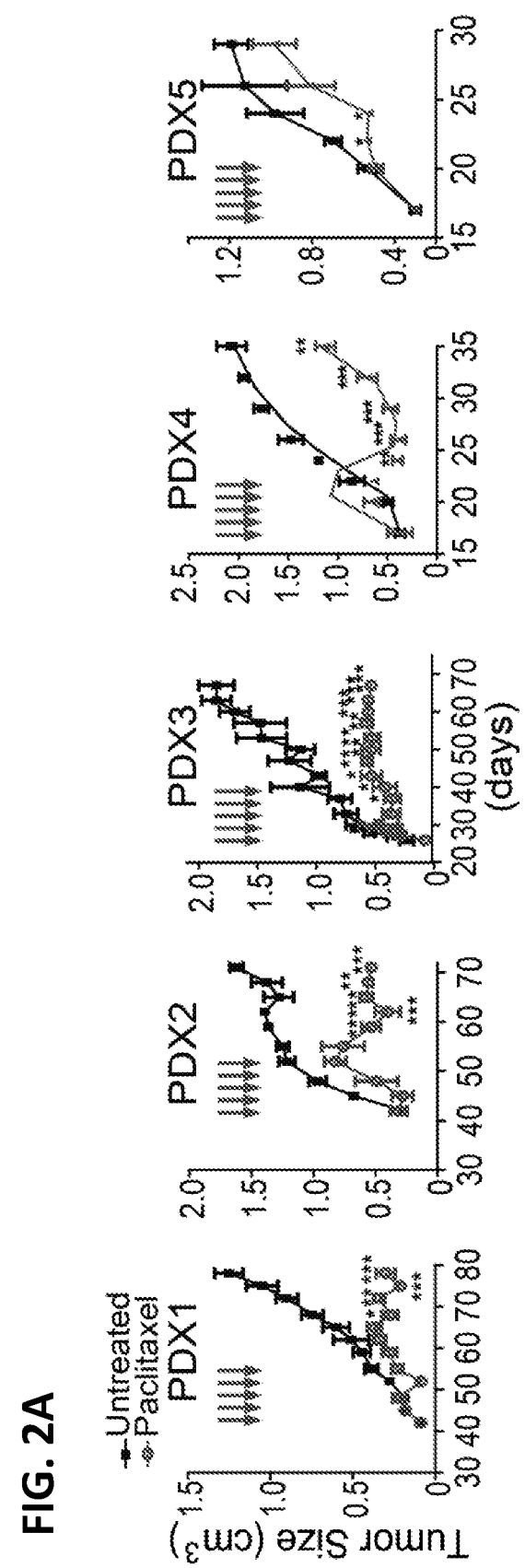

| Tissue ID | Treatment | Cell Number | | Frequency of Tumorigenic Cell | P Value |
|---|---|---|---|---|---|
| | | $10^4$ | $10^3$ | | |
| PDX4 | Untreated | 3/5 | 0/5 | 1/12683 | 0.0002 |
| | Paclitaxel | 5/5 | 4/5 | 1/622 | |
| PDX5 | Untreated | 4/5 | 0/5 | 1/7697 | 0.002 |
| | Paclitaxel | 5/5 | 4/5 | 1/622 | |

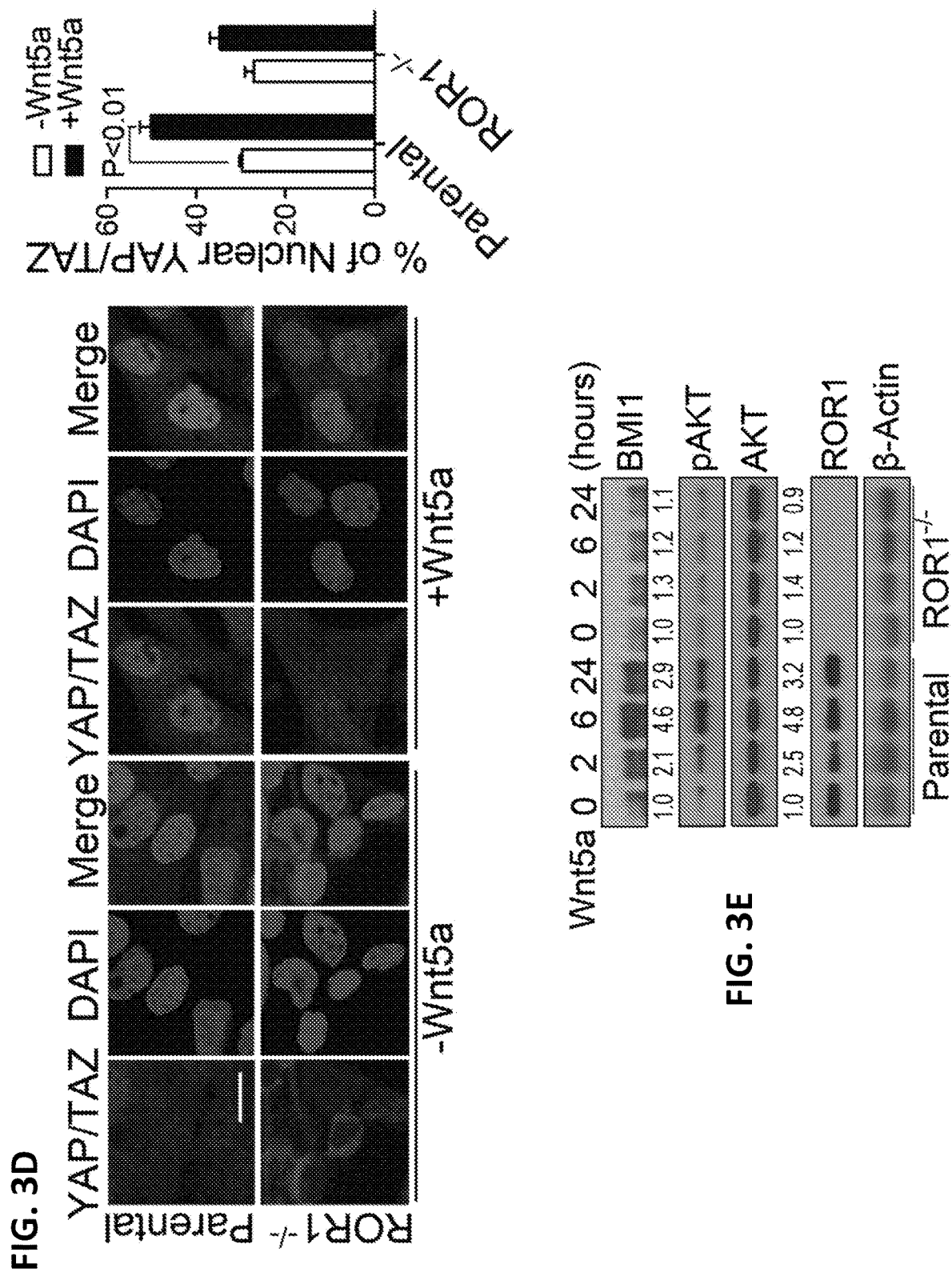

| | Treatment | Cell Number | | | Frequency of Tumorigenic Cell | P Value |
|---|---|---|---|---|---|---|
| | | 1X10⁵ | 1X10⁴ | 1X10³ | | |
| PDX4 | hIgG | 10/10 | 10/10 | 0/5 | 1/3285 | 8.61e-13 |
| | cirmtuzumab | 2/10 | 1/10 | 0/5 | 1/247052 | |
| PDX5 | hIgG | N.D | 5/5 | 2/4 | 1/1420 | 0.001 |
| | cirmtuzumab | N.D | 1/5 | 1/3 | 1/23572 | |

| Treatment | Cell Number | | | |
|---|---|---|---|---|
| | PDX4 | | PDX5 | |
| | $1 \times 10^5$ | $1 \times 10^4$ | $1 \times 10^5$ | $1 \times 10^4$ |
| Control | 5/5 | 5/5 | 5/5 | 5/5 |
| cirmtuzumab | 2/5 | 1/5 | 3/5 | 2/5 |
| Paclitaxel | 5/5 | 5/5 | 4/5 | 3/3 |
| cirmtuzumab + Paclitaxel | 0/5 | 0/4 | 0/5 | 0/3 |

2nd transplantation

Control (n=5)

cirmtuzumab (n=5)

Paclitaxel (n=3)

cirmtuzumab +Paclitaxel (n=3)

— 1cm

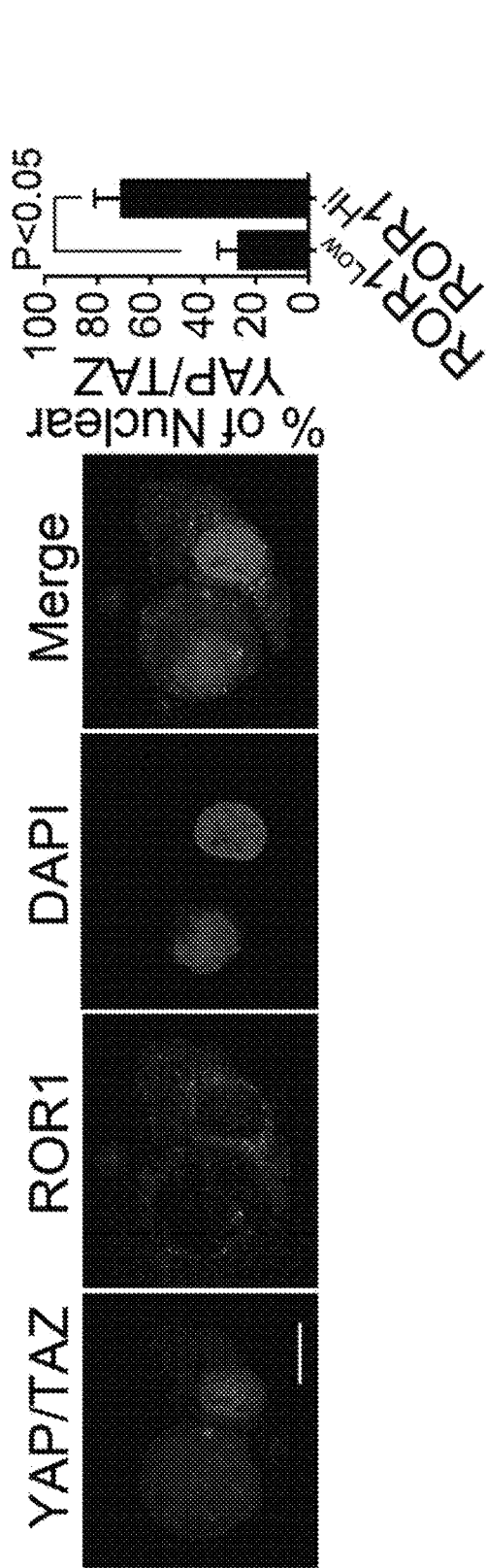
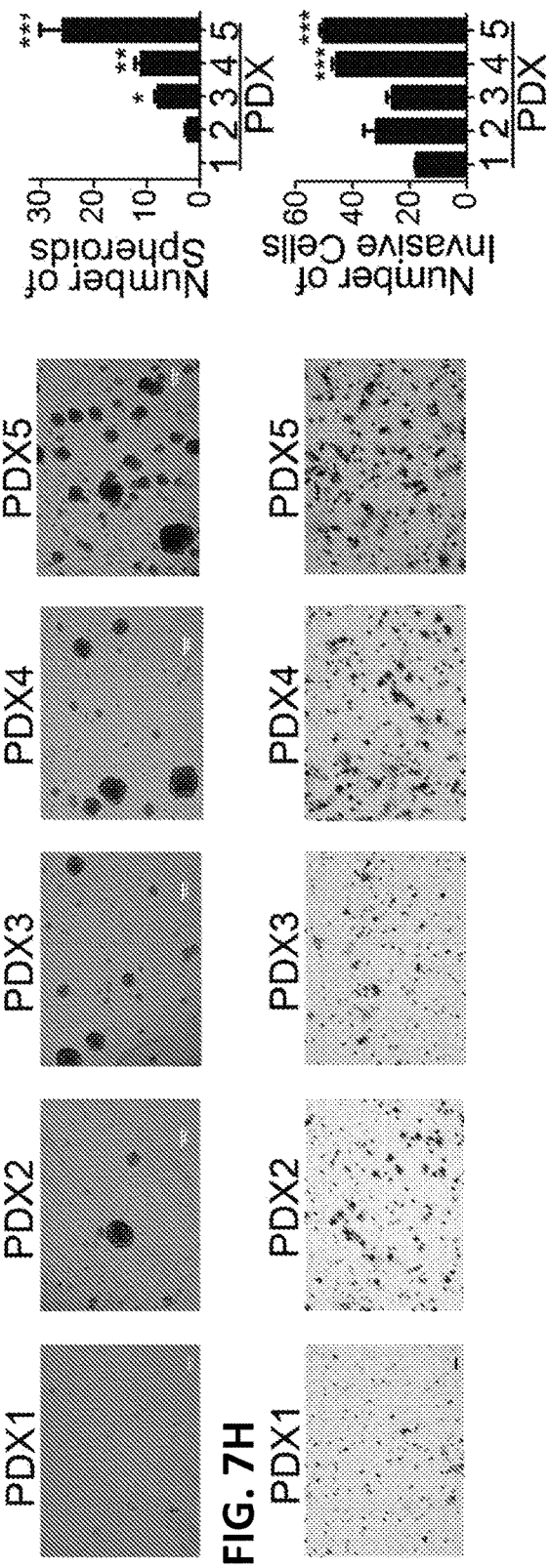
FIG. 7F
FIG. 7G
FIG. 7H

FIG. 7N
| Tissue ID | | Cell Number | | | Frequency of Tumorigenic Cell | P Value |
|---|---|---|---|---|---|---|
| | | 5000 | 500 | 100 | | |
| PDX4 | ROR1+ | 6/6 | 4/6 | N.D | 1/455 | <0.001 |
| | ROR1Neg | 3/6 | 2/6 | N.D | 1/4740 | |
| PDX5 | ROR1+ | N.D | 8/9 | 1/10 | 1/329 | <0.001 |
| | ROR1Neg | N.D | 1/9 | 0/10 | 1/5247 | |
FIG. 8A
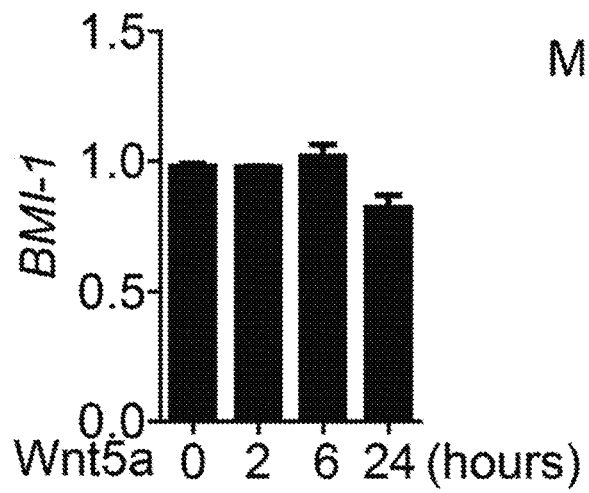
FIG. 8B
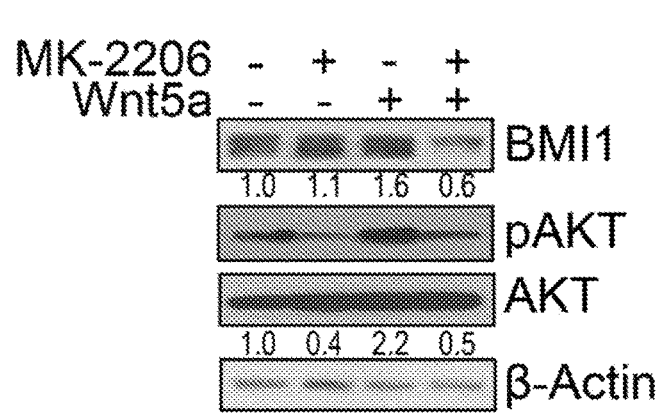

FIG. 12
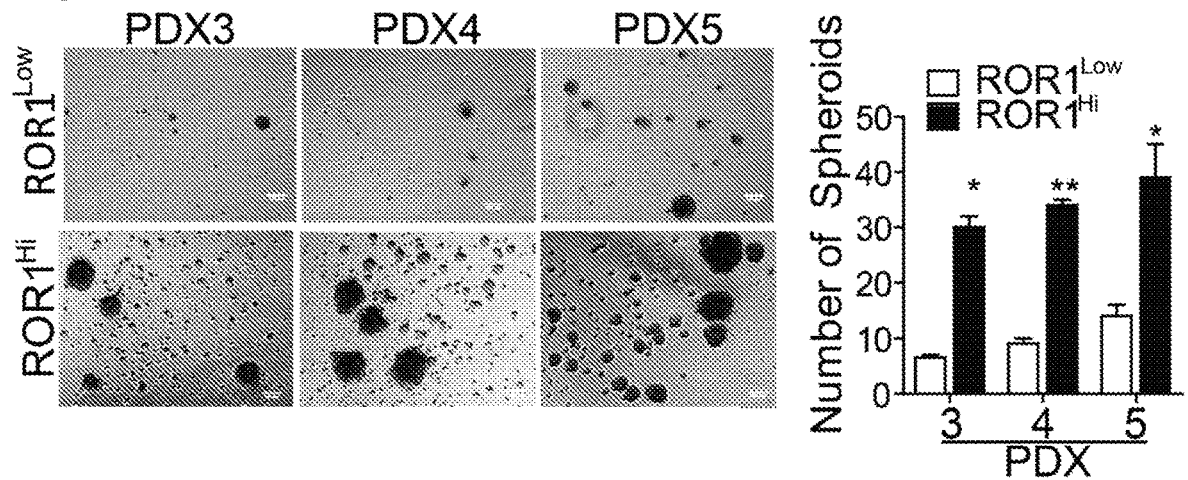
FIG. 13
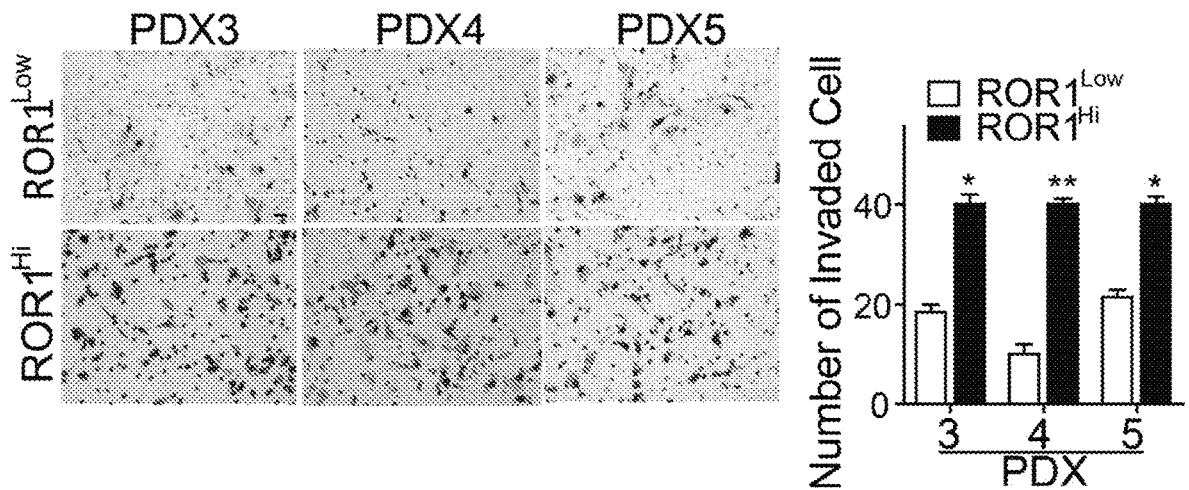
FIG. 14
| Tissue ID | | Cell Number | | | Frequency of Tumorigenic Cell | P Value |
|---|---|---|---|---|---|---|
| | | 5000 | 500 | 100 | | |
| PDX3 | ROR1$^{Low}$ | 0/4 | 0/9 | 0/10 | 1/2913 | <0.01 |
| | ROR1$^{Hi}$ | 2/5 | 5/10 | 1/10 | Inf | |
| PDX4 | ROR1$^{Low}$ | 3/6 | 2/6 | N.D | 1/455 | <0.001 |
| | ROR1$^{Hi}$ | 6/6 | 4/6 | N.D | 1/4740 | |
| PDX5 | ROR1$^{Low}$ | N.D | 1/9 | 0/10 | 1/329 | <0.001 |
| | ROR1$^{Hi}$ | N.D | 8/9 | 1/10 | 1/5247 | |

FIG. 15
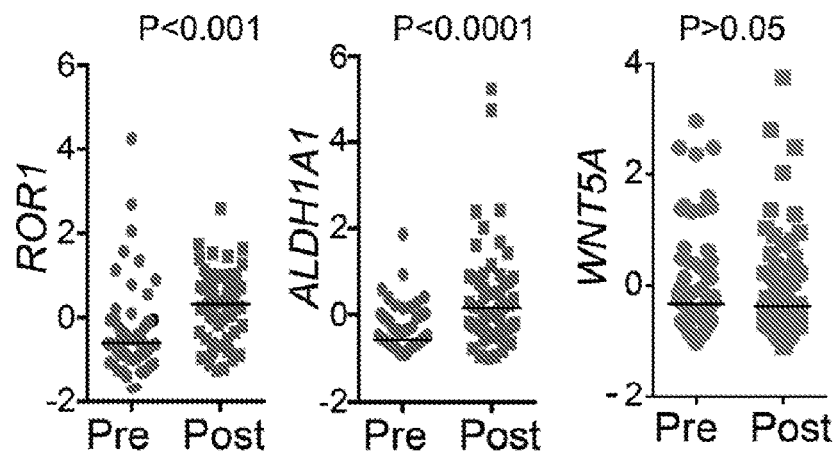
FIG. 16
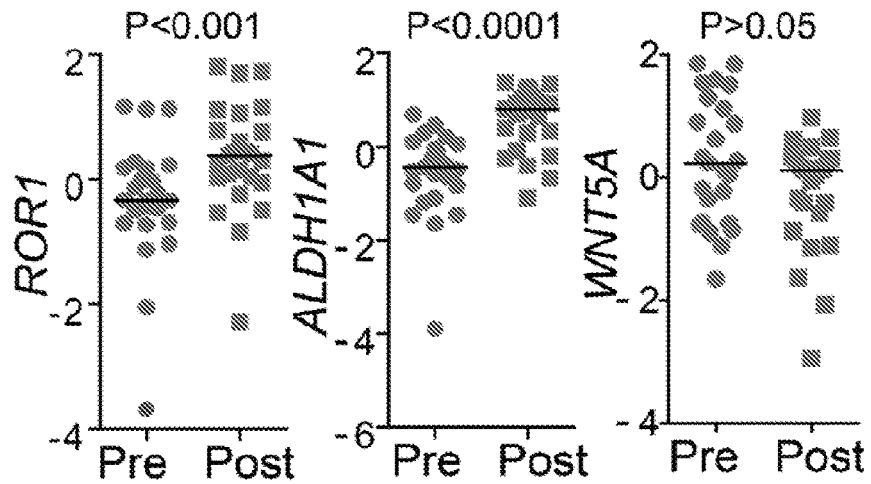
FIG. 17
| Gene Sets | Size | ES | | NES | | NOM p-val | | FDR q-val | |
|---|---|---|---|---|---|---|---|---|---|
| | | $ROR1^{hi}$ vs $ROR1^{Low}$ | Post vs Pre | $ROR1^{hi}$ vs $ROR1^{Low}$ | Post vs Pre | $ROR1^{hi}$ vs $ROR1^{Low}$ | Post vs Pre | $ROR1^{hi}$ vs $ROR1^{Low}$ | Post vs Pre |
| $CD44^+/CD24^{Low}$ MS | 99 | 0.46 | 0.52 | 1.61 | 2.16 | 0.03 | 0.00 | 0.07 | 0.00 |
| EMT | 220 | 0.52 | 0.31 | 1.78 | 1.47 | 0.00 | 0.00 | 0.00 | 0.03 |
| Rac1 Pathway | 22 | 0.48 | 0.52 | 1.44 | 1.61 | 0.05 | 0.01 | 0.08 | 0.01 |
| RhoA Pathway | 45 | 0.44 | 0.41 | 1.34 | 1.52 | 0.12 | 0.03 | 0.12 | 0.02 |
| cdc42 | 30 | 0.46 | 0.35 | 1.47 | 1.19 | 0.05 | 0.22 | 0.12 | 0.16 |
| Hippo-Yap | 57 | 0.53 | 0.36 | 1.60 | 1.33 | 0.04 | 0.07 | 0.03 | 0.07 |
| BMI1 | 143 | 0.32 | 0.42 | 1.17 | 1.90 | 0.20 | 0.00 | 0.20 | 0.00 |

SEQUENCE LISTING

<160> NUMBER OF SEQ ID NOS: 17

<210> SEQ ID NO 1
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 1

Gly Tyr Ala Phe Thr Ala Tyr Asn
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 2

Phe Asp Pro Tyr Asp Gly Gly Ser
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 3

Gly Trp Tyr Tyr Phe Asp Tyr
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 4

Lys Ser Ile Ser Lys Tyr
1               5

<210> SEQ ID NO 5
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 5

Ser Gly Ser
1

<210> SEQ ID NO 6
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 6

Gln Gln His Asp Glu Ser Pro Tyr
1               5

```
<210> SEQ ID NO 7
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 7

Gly Phe Ser Leu Thr Ser Tyr Gly
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 8

Ile Trp Ala Gly Gly Phe Thr
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 9

Arg Gly Ser Ser Tyr Ser Met Asp Tyr
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 10

Ser Asn Val Ser Tyr
1               5

<210> SEQ ID NO 11
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 11

Glu Ile Ser
1

<210> SEQ ID NO 12
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 12

Gln Gln Trp Asn Tyr Pro Leu Ile Thr
1               5
```

```
<210> SEQ ID NO 13
<211> LENGTH: 19
<212> TYPE: DNA
<213> ORGANISM: Artificial Sequence
<220> FEATURE:
<223> OTHER INFORMATION: GAPDH forward primer

<400> SEQUENCE: 13
gaaggtgaag gtcggagtc                                                  19

<210> SEQ ID NO 14
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 14
gaagatggtg atgggatttc                                                 20

<210> SEQ ID NO 15
<211> LENGTH: 22
<212> TYPE: DNA
<213> ORGANISM: Artificial Sequence
<220> FEATURE:
<223> OTHER INFORMATION: BMI1 forward primer

<400> SEQUENCE: 15
cgtgtattgt tcgttacctg ga                                              22

<210> SEQ ID NO 16
<211> LENGTH: 22
<212> TYPE: DNA
<213> ORGANISM: Artificial Sequence
<220> FEATURE:
<223> OTHER INFORMATION: BMI1 reverse primer

<400> SEQUENCE: 16
ttcagtagtg gtctggtctt gt                                              22

<210> SEQ ID NO 17
<211> LENGTH: 23
<212> TYPE: DNA
<213> ORGANISM: Homo sapiens

<400> SEQUENCE: 17
ccagtgcgtg gcaacaaacg gca                                             23
```

COMBINATION TREATMENT OF CHEMORESISTANT CANCERS

CROSS-REFERENCES TO RELATED APPLICATIONS

This application is a U.S. National Phase Application of International Application No. PCT/US2019/021694, filed Mar. 11, 2019, which is an international application of and claims the benefit of priority under 35 U.S.C. § 119(e) to U.S. Provisional Application No. 62/641,035, filed Mar. 9, 2018 each of which are hereby incorporated by reference in their entirety and for all purposes.

STATEMENT AS TO RIGHTS TO INVENTIONS MADE UNDER FEDERALLY SPONSORED RESEARCH AND DEVELOPMENT

This invention was made with government support under Grant No. CA081534 awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048537-605001WO__SEQUENCE_LISTING_ST25.TXT, created on Mar. 8, 2019, 3,371 bytes, machine format IBM-PC, MS-Windows operating system, is hereby incorporated by reference.

BACKGROUND

Advances in chemotherapy and endocrine therapy have reduced breast cancer mortality, but 20% of patients still relapse and ultimately succumb to this disease. (Early Breast Cancer Trialists' Collaborative et al., 2012) One model accounting for this posits that there exists cancer stem cells (CSCs), which are relatively resistant to chemotherapy, have self-renewal capacity, can repopulate the tumor, and can spread to distant sites. (Brooks et al., 2015; Wahl and Spike, 2017). If so, therapies that also target CSCs may improve treatment outcomes and patient survival.

Studies have identified characteristics that distinguish CSCs from other cancer cells. CSCs have the distinctive capacities to form non-adherent cellular spheroids and engraft immune-deficient mice. (Al-Hajj et al., 2003; Creighton et al., 2009) Such cells have gene-expression signatures that reflect their relatively high capacity for self-renewal and/or drug-resistance. (Creighton et al., 2009) Notable is activation of the Hippo-YAP pathway, which induces genetic changes that contribute to self-renewal, resistance to chemotherapy, and/or metastatic potential. (Chan et al., 2008; Cordenonsi et al., 2011; Maugeri-Sacca and De Maria, 2016; Moroishi et al., 2015)

Another notable feature of CSCs is the enhanced expression of B-lymphoma-Mo-MLV insertion region 1 homolog (BMI1); high-level BMI1 is associated with breast cancers that have a basal-like phenotype, which is associated with poor patient survival. (Wang et al., 2012) BMI1 may promote CSCs self-renewal and tumor-initiation capacity (Kreso et al., 2014; Paranjape et al., 2014; Wu et al., 2011). Moreover, BMI1 can enhance expression of genes encoding ATP-binding cassette (ABC) transporters, which enhance resistance to chemotherapy. (Su et al., 2015; Wu et al., 2011)

Breast CSCs also have phenotypic features that distinguish them from other neoplastic cells. CSCs have distinctive expression of Aldehyde Dehydrogenase 1 (ALDH1) and generally express CD2, CD49f, CD133, and/or CD44, in conjunction with low levels of CD24 ($CD24^{low}$) or CD47. (Al-Hajj et al., 2003; Ginestier et al., 2007; Kaur et al., 2016) However, such CSC-associated surface proteins are not restricted to neoplastic cells. An exception is ROR1, a type I orphan-receptor tyrosine kinase-like, which is expressed by many cancers, but not by normal post-partum tissues. (Zhang et al., 2012b) Breast cancers with high-levels of ROR1+ cells tend to be poorly differentiated and to express markers associated with epithelial-to-mesenchymal transition (EMT). (Cui et al., 2013) High-level expression of ROR1 is associated with relatively short post-treatment disease-free or overall survival of patients with triple-negative breast cancer. (Zhang et al., 2012a; Chien et al., 2016) Conversely, silencing ROR1 attenuated expression of genes associated with EMT and impaired cancer-cell migration/invasion in vitro and metastasis in vivo, revealing a relationship between ROR1 and features associated with CSCs and/or poor prognosis. (Cui et al., 2013)

Prior studies showed ROR1 is a receptor for Wnt5a, (Fukuda et al., 2008) which can induce non-canonical Wnt-signaling in chronic lymphocytic leukemia (CLL), leading to activation of Rho-GTPases and enhanced tumor-cell proliferation and survival. (Yu et al., 2015) Rho proteins, including RhoA, Rac1, and cdc42, are expressed at high levels in breast cancer relative to non-neoplastic breast tissue. (Fritz et al., 1999) Activation of Rho GTPases can contribute oncogenesis and enhance resistance to chemotherapy. (Hein et al., 2016) Moreover, Wnt-induced activation of Rho-GTPases can promote activation YAP/TAZ in HEK293A cells. (Park et al., 2015) However, it is not known whether aberrant expression of ROR1 contributes to activation of Rho-GTPase signaling, YAP/TAZ activation, or BMI1 in breast-cancer cells, or whether ROR1-dependent signaling enhances drug-resistance and/or tumor-cell self-renewal.

Provided here are solutions to these and other problems in the art.

BRIEF SUMMARY OF THE INVENTION

In an aspect is provided, a method of treating a chemoresistant cancer in a subject in need thereof. The method includes administering to the subject a therapeutically effective amount of a chemotherapeutic agent and a therapeutically effective amount of a tyrosine kinase-like orphan receptor 1 (ROR-1) antagonist, thereby treating a chemoresistant cancer in the subject.

In an aspect is provided, a method of treating breast cancer in a subject in need thereof. The method includes administering to the subject a therapeutically effective amount of a chemotherapeutic agent and a therapeutically effective amount of a tyrosine kinase-like orphan receptor 1 (ROR-1) antagonist, thereby treating a chemoresistant breast cancer in the subject.

In an aspect is provided, a pharmaceutical composition including (i) a chemotherapeutic agent selected from the group consisting of plant alkaloid, an antitumor antibiotic and a topoisomerase inhibitor, (ii) a ROR-1 antagonist and (iii) a pharmaceutically acceptable excipient.

In an aspect is provided, a pharmaceutical composition including (i) a chemotherapeutic agent selected from the group consisting of a plant alkaloid, an antitumor antibiotic and a topoisomerase inhibitor, (ii) an anti-ROR-1 antibody and (iii) a pharmaceutically acceptable excipient, wherein the chemotherapeutic agent and the anti-ROR-1 antibody are present in a combined synergistic amount, wherein the combined synergistic amount is effective to treat breast cancer in a subject in need thereof.

BRIEF DESCRIPTION OF THE DRAWINGS

(FIG. 1B), ROR1 or ALDH1A1 expression levels in breast cancer patient samples before ("Pre") or matched after chemotherapy ("Post") (Post, Pre, N=57). The line indicates the median expression level of genes in the pre- versus the post-treatment subgroup. (FIG. 1C), Enrichment plots of genes activated by Rae1/RhoA/cdc42-signaling on post-treatment samples (N=57) versus matched pre-treatment samples (N=57) in the GSE87455 dataset. (FIG. 1D), Immunoblot analyses for proteins as indicated on the right, using lysates prepared from breast cancer tissues of treatment naïve patients. Probing for β-actin served as protein-loading control. The numbers below each lane represent the ratios of the band densities for each protein relative to that of β-actin, normalized with respect to the ratios noted for Patient 1. (FIG. 1E), Pearson correlation analysis for ROR1 versus TAZ or ROR1 versus BMI1 in breast cancer biopsies obtained from patients prior to therapy. (FIG. 1F), Representative images of breast cancer tissues stained with the anti-ROR1 mAb, 4A5. Scale bar: 25 μM. (FIG. 1G), Immunohistochemical staining of ROR1 in breast biopsy specimens obtained from patients before (Pre) or after (Post) therapy with docetaxel/epirubicin±cyclophosphamide. The P value was determined using Fisher's exact test FIGS. 2A-2E. The figures show ROR1+ Breast Cancer Cells Are Enriched For Cells With The Phenotypic And Functional Features of Breast CSCs After Palcitaxel Treatment. (FIG. 2A), The graph depicts the mean tumor growth over time (±SEM) for animals that did not receive treatment (square data points, N=7) or had received paclitaxel (round data points, N=5) on the days indicated by the arrows.

(FIG. 3A), Immunoblot analyses for proteins as indicated on the right, using lysates prepared from Hs578T cells (Parental), or Hs578T knocked out for ROR1 (ROR1−/−), that were stimulated with Wnt5a for times indicated at the top. The numbers below each lane represent the ratios of the band densities for each protein relative to that of 13-actin, normalized with respect to cells treated without Wnt5a. (FIG. 3B), Immunoblot analyses for proteins indicated on the right, using lysates of Hs578T cells that had been treated with an isotype control IgG (hIgG) or cirmtuzumab, and then stimulated with Wnt5a for the times indicated on the top. The numbers below each lane represent the ratios of band densities for each protein relative to that of 13-actin, normalized with respect to the hIgG-treated cells without Wnt5a. (FIG. 3D), Photomicrographs of parental (top row) or ROR1−/− Hs578T cells (bottom row) that were treated without or with Wnt5a, as indicated at the bottom, and then stained for YAP/TAZ and DAPI, as indicated at the top, and then examined using confocal microscopy. Scale bar: 20 μm. The histogram to the right of the photomicrographs provides the average percentages of YAP/TAZ located within the nuclei of the cells in each field (N=10, ±SEM). (FIG. 3E), Immunoblot analyses for proteins indicated on the right, using lysates prepared from Hs578T cells that were cultured with cirmtuzumab or hIgG, and then treated without or with Wnt5a, as indicated at the top. The numbers below each lane are as in 3B. (FIG. 3P), Percent viable cells of Hs578T that were cultured in medium with hIgG or cirmtuzumab that was supplemented without or with Wnt5a (as indicated in the legend) and then treated with paclitaxel, at the concentrations indicated below. Data points represent the mean percentages of viable cells in triplicate wells ±SEM.

(FIG. 4A), The line graph depicts the mean tumor growth of PDX4 or PDX5 over time (±SEM, N=6-8) for animals that did not receive treatment (data points represented by squares) or that were treated with cirmtuzumab (data points represented by circles) on the days indicated by the black arrows. One asterisk indicates P<0.05, two indicates P<0.01, using Student's t-Test. (FIG. 4B), The bar graph provides average weight of tumors extirpated from the mice in each group described in FIG. 1A (±SEM, N=6-8). (FIG. 4C), HE staining of lung tissue from a representative tumor-bearing mouse engrafted with cells of PDX5 and treated with control hIgG or cirmtuzumab, as indicated on the left. A dashed-lined circle highlights a metastatic focus. Scale bar: 100 µm. The scatter plot shows average numbers of metastatic foci that were found in the lungs of each animal by treatment group (±SEM, N=6). (FIG. 4D), Enrichment plots of genes associated with activation of Rho-GTPases, Hippo-YAP, or BMI1, or genes up-regulated in CD44+/CD24$^{Low}$ cells (CD44+/CD24$^{Low}$ UP) in PDX derived from PDX4 in mice treated with control hIgG versus cirmtuzumab, as assessed via RNAseq (GSE108632). (FIG. 4E), Immunoblot analyses for proteins indicated on the right, using lysates prepared from PDX4 or PDX5 (as indicated on the bottom) that were extirpated from mice treated with control hIgG or cirmtuzumab, as indicated at the top. Numbers below each row are the ratios of band densities of activated versus total GTPase, pAKT versus total AKT, BMI1, ABCG2, TAZ/YAP, CTGF versus 13-Actin, or ROR1 versus 13-Actin normalized to that of the first control sample. (FIG. 4F), Representative contour plots showing the relative expression of CD44 and CD24 on tumor cells isolated from PDX4 that was removed from mice treated with either hIgG or cirmtuzumab. The scatter plot shows the average proportions of CD44+/CD24$^{Low}$ that were found in PDX4 tumors of each group (N=6). (FIG. 4G), Table providing the numbers of mice that developed tumors (numerator) versus the numbers of mice implanted (denominator) with cells from either PDX4 or PDX5 (as indicated in the left column), which were removed from mice treated with either hIgG or cirmtuzumab (as indicated in the second column). For these experiments, mice were given varying numbers of tumor cells (as indicated in the row below "cell number"). The frequencies of tumorigenic cells computed using ELDA software are provided in the penultimate right column. The P values indicate the significance of the difference between the tumorigenic frequencies of tumor cells recovered from hIgG-versus cirmtuzumab-treated mice.

(FIG. 5A), The line graph depicts the mean tumor growth of PDX4 or PDX5 over time (±SEM, N=8-10) in mice that either were untreated (Control, data points represented by squares) or treated with cirmtuzumab (data points represented by circles) on the days indicated by the black arrows, paclitaxel (data points represented by triangles pointing up) on the days indicated by the red arrows, or both (data points represented by triangles pointing down). (FIG. 5B), Immunoblot analyses for proteins indicated on the right, using lysates prepared from PDX4 isolated from mice that had not been treated (Control) or treated with cirmtuzumab, paclitaxel, or both, as indicated on the top. Numbers below each row are the ratios of band densities as in 4E. (FIG. 5C), Table providing the numbers of mice that developed PDX (numerator) versus the numbers of mice engrafted (denominator) with cells from either PDX4 or PDX5 (as indicated in the top row) that were removed from mice treated with either hIgG, cirmtuzumab, paclitaxel, or cirmtuzumab and paclitaxel (as indicated in the far left column). For these experiments, mice were given varying numbers of tumor cells (as indicated in the row below the PDX designation). The bottom panel provides a photograph of representative tumors that developed in mice engrafted with tumor cells from PDX4 removed from mice that were untreated or treated with cirmtuzumab and/or paclitaxel, as indicated on the right.

(FIG. 6A), Enrichment plots of genes associated with activation of Rac1/RhoA/cdc42, Hippo-YAP, BMI1 for the ROR1$^{Low}$ and ROR1$^{Hi}$ sample groups from the GSE21974 (N=25). SIZE is the number of genes included in the analysis. NES (normalized enrichment score) accounts for the difference in gene-set size and can be used to compare the analysis results across gene sets. FDR q-val (false discovery rate q value) is the estimated probability that a gene set with a given NES represents a false positive. Each gene set is considered significant when the false discovery rate (FDR) is less than 0.25. The middle portion of the plot shows where the members of the gene set appear in the list of ranked genes. (FIG. 6B), ROR1 or ALDH1A1 expression levels in matched breast cancer patient samples before ("Pre") or after chemotherapy ("Post") (Post, Pre, N=25). The line indicates the median expression level of genes in pre-versus post-treatment group.

FIGS. 7A-7N. The figures show ROR1$^{Hi}$ Breast Cancers Express Higher Levels Of Markers Associated With CSCs And Had Greater Capacity To Form Spheroids, Invade Matrigel Or Form Xenografts Than ROR$^{Low}$ Breast Cancers. (FIG. 7A), Gating strategy for primary tumor cells isolated from each PDX. Single-cell suspensions were made from extirpated tumor nodules and stained with propidium iodide (PI), Calcein Violet or fluorescein diacetate (FDA), and fluorochrome-conjugated mAb specific for EpCAM, or an irrelevant antigen (control). We gated on cells having the appropriate forward light scatter (FSC) and side scatter (SSC) characteristics (left). We excluded dead cells labeled with PI and gated on live cells that stained with Calecein Violet (middle). Because the cells also were stained with fluorochrome-conjugated mAbs, we gated on human breast cancer cells that were stained with mAbs specific for EpCAM (right). (FIG. 7F), Confocal microscopy examining for ROR1 or YAP/TAZ on single tumor cells isolated from PDX tumors. Scale bar: 20 µm. The right bar graph provides the average percentages of nuclear YAP/TAZ in the cells isolated from each PDX. (FIG. 7G), Photomicrographs of spheroids generated by cells isolated from each of PDX. Scale bar: 100 µm. The bar graph depicts the average numbers of spheroids formed by cells from each PDX in triplicate wells ±SEM. (FIG. 7H), Representative photomicrographs of invasive cells from isolated tumor cells of each PDX. To the right of the photomicrographs are bar graphs depicting the mean relative proportions of tumor cells that migrated into Matrigel (±SEM) from each tumor cell population in three independent experiments, each normalized to the proportion of the tumor cells from PDX5 that migrated into Matrigel. Scale bar: 10 µm. An asterisk represents P<0.05,  denotes P<0.01, and * represents P<0.001, using Dunnett's multiple comparison test. (FIG. 7J), The open boxes in the right of the contour plots depict the gates used to identify cells that are certain to have ALDH1 activity. The number in each histogram depicts percentage of ALDH1+ cells. (FIG. 7N), Tumor incidence in animals implanted with ROR1+ or ROR1$^{Neg}$ cells isolated from each of the various breast cancer PDX. Frequency of tumorigenic cells and probability estimates were computed using ELDA software. N.D indicates not done.

FIGS. 8A-8B. The figures show Enhanced BMI1 Expression Induced By Wnt5a Is Dependent On Activation Of AKT. (FIG. 8A), BMI1 mRNA level in Hs578T cells treated with Wnt5a at 100 ng/ml at indicated time point were examined by quantitative PCR (qPCR). Data shown were the mean expression levels of BMI1 relative to time 0 samples in triplicate and normalized with respect to GAPDH. Error bars indicate SEM. (FIG. 8B), Hs578T cells were cultured in serum-free medium, pre-treated with or without MK-2206 for 3 hours, and then stimulated with or without Wnt5a at 100 ng/ml for 6 hours. BMI1, pAKT and AKT were examined on these samples via immunoblot analyses. Numbers below the row for AKT provide the ratios of band densities of pAKT to AKT that were normalized to that of samples treated for 0 minutes with Wnt5a. β-Actin served as protein-loading control. Numbers below the row for BMI1 provide the ratios of band densities of BMI1 to β-Actin, normalized with respect to that of samples treated for 0 minutes with Wnt5a.

(FIG. 9A), Lysates from PDX1-PDX5 were examined for expression of Wnt5a, as indicated on the right margin. β-Actin serves as loading control. (FIG. 9B), Single cell suspension isolated from PDX4 or PDX5 treated with cirmtuzumab antibody or control antibody at 50 µg/ml for 4 hours were examined for YAP/TAZ via confocal microscopy. Right bar graph provides the average percentages of nuclear YAP/TAZ in the cells of each field. Scale bar: 20 µm. (FIG. 9C), Lysates from PDX4 or PDX5 treated with cirmtuzumab antibody or control antibody at 50 µg/ml for the indicated times were examined for BMI1, ROR1 or 13-Actin via immunoblot analyses. (FIG. 9D), Representative photomicrographs of spheroids formed from isolated tumor cells of different PDX treated with either control antibody or cirmtuzumab at 50 µg/ml. The bar graph on right panel depicts the average numbers of spheroids formed from tumor cells of PDX4 or PDX5 treated with cirmtuzmab or a control antibody in three separate culture wells of each treatment ±SEM. (FIG. 9E), Representative photomicrographs of invasive cells from isolated tumor cells of different PDX treated with either control antibody or cirmtuzumab at 50 µg/ml. To the right of the photomicrographs are bar graphs depicting the mean number of invaded cells of each of the cell preparations in three independent experiments ±SEM. Scale bar: 10 m. (FIG. 9F), 1×106 cells from each PDX sample in 50 µl were mixed with equal volumes of Matrigel and then injected into the mammary pad of female Rag2−/−γc−/− mice. Tumor growth was monitored over time for 42 or 48 days. Representative photographs of each PDX removed at 42 (PDX5) or 48 (PDX4) days. Scale bar: 1 cm.

FIG. 12. This figure shows photomicrographs of spheroids formed from ROR1HI or ROR1$^{Neg}$ cells isolated from each of the PDX, as indicated on the top. Scale bar: 100 μm. The bar graph to the right depicts the average numbers of spheroids formed ±SEM by each of the cell preparations in three separate cultures, as indicated at the bottom of the histograms.

FIG. 13. This figure shows photomicrographs of Matrigel-invading cells from ROR1HI or ROR1Low cells isolated from different PDX, as indicated on the top. Scale bar: 10 μm. The bar graph to the right depicts the mean invaded cells into Matrigel (±SEM) per field for 10-20 fields of each of the cell preparations in three independent experiments.

FIG. 14. This figure shows tumor incidence in animals implanted with ROR1Hi or ROR1Low cells isolated from each of the various breast cancer PDX. Frequency of tumorigenic cells and probability estimates were computed using ELDA software. N.D indicates not done.

FIG. 15. This figure shows ROR1, ALDH1A1, Wnt5a expression levels in matched breast cancer patient samples before ("Pre") or after chemotherapy ("Post") (Post, Pre, N=57, GSE87455).

FIG. 16. This figure shows ROR1, ALDH1A1 or Wnt5a expression levels in matched breast cancer patient samples before ("Pre") or after chemotherapy ("Post") (Post, Pre, N=25, GSE21974). The line indicates the median expression level of genes in pre-versus post-treatment group.

FIG. 17. This figure shows gene Set Enrichment (GSE) Analysis for genes associated with CD44+/CD24Low MS, ETM, activation of Rac1/RhoA/cdc42, Hippo-YAP, BMI1 for the ROR1Low and ROR1Hi sample groups (N=25) or on breast cancer biopsies from patients who received neoadjuvant chemotherapy (N=25) Versus Matched Pre-treatment Samples (N=25) in the GSE21974 database. SIZE is the number of genes included in the analysis. NES (normalized enrichment score) accounts for the difference in gene-set size and can be used to compare the analysis results across gene sets. NOM p-val (nominal p value) is the statistical significance of the enrichment score not adjusted for gene set size or multiple gene sets testing, FDR q-val (false discovery rate q value) is the estimated probability that a gene set with a given NES represents a false positive. Each gene set is considered significant when the false discovery rate (FDR) is less than 0.25.

DETAILED DESCRIPTION

I. Definitions

Figure 1A:
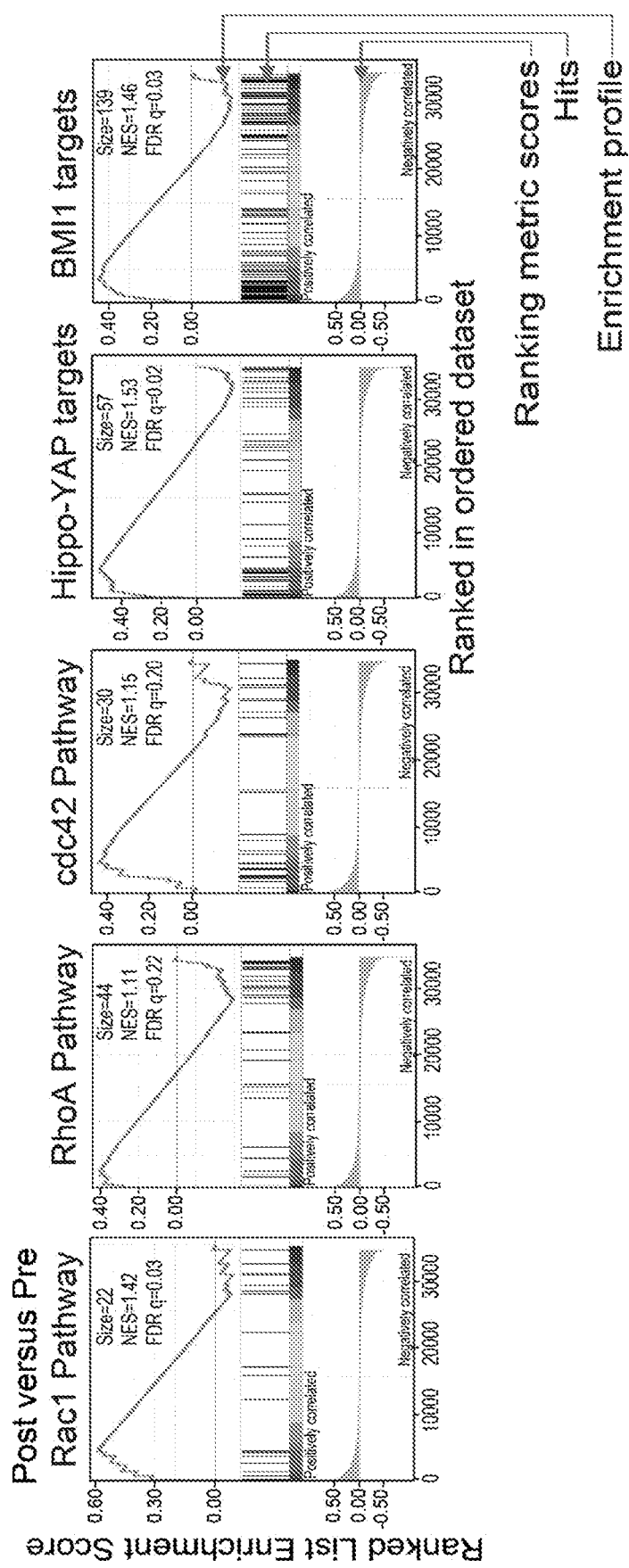
FIGS. 1A-1G. The figures show Expression Of ROR1 And Genes Associated With CSC Before and After Chemotherapy (FIG. 1A), Enrichment plots of Rac1/RhoA/cdc42 signaling pathway, Hippo-YAP target genes and BMI1 target genes on ROR1Hi tumors (N=61) versus ROR1Low tumors (N=61) from patients prior to therapy in the GSE87455 dataset.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched non-cyclic chain, or combinations thereof, including at least one carbon atom and at least one heteroatom (e.g. O, N, P, Si, and S), and wherein the nitrogen and sulfur atoms may optionally be oxidized, and the nitrogen heteroatom may optionally be quaternized. The heteroatom(s) (e.g. O, N, P, S, and Si) may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CHO—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S(O$_2$)—R', where R' is a substituted or unsubstituted alkyl group as defined above. R' may have a specified number of carbons (e.g., "C$_1$-C$_4$ alkylsulfonyl").

Each of the above terms (e.g., "alkyl", "heteroalkyl", "cycloalkyl", "heterocycloalkyl", "aryl", and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In embodiments, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:
  (i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, heteroaryl, substituted with at least one substituent selected from:
    (a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present invention, whether radioactive or not, are encompassed within the scope of the present invention.

Analog" and "analogue" are used interchangeably and are used in accordance with their plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "antibody" is used according to its commonly known meaning in the art. Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_{H1}$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms "variable heavy chain," "$V_H$," or "VH" refer to the variable region of an immunoglobulin heavy chain, including an Fv, scFv, dsFv or Fab; while the terms "variable light chain," "$V_L$" or "VL" refer to the variable region of an immunoglobulin light chain, including of an Fv, scFv, dsFv or Fab.

Examples of antibody functional fragments include, but are not limited to, complete antibody molecules, antibody fragments, such as Fv, single chain Fv (scFv), complementarity determining regions (CDRs), VL (light chain variable region), VH (heavy chain variable region), Fab, F(ab)2' and any combination of those or any other functional portion of an immunoglobulin peptide capable of binding to target antigen (see, e.g., FUNDAMENTAL IMMUNOLOGY (Paul ed., 4th ed. 2001). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al., (1990) Nature 348:552). The term "antibody" also includes bivalent or bispecific molecules, diabodies, triabodies, and tetrabodies. Bivalent and bispecific molecules are described in, e.g., Kostelny et al. (1992) J. Immunol. 148:1547, Pack and Pluckthun (1992) Biochemistry 31:1579, Hollinger et al. (1993), PNAS. USA 90:6444, Gruber et al. (1994) J Immunol. 152:5368, Zhu et al. (1997) Protein Sci. 6:781, Hu et al. (1996) Cancer Res.

56:3055, Adams et al. (1993) *Cancer Res.* 53:4026, and McCartney, et al. (1995) *Protein Eng.* 8:301.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

An amino acid residue in a protein "corresponds" to a given residue when it occupies the same essential structural position within the protein as the given residue.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

The term "peptidyl" and "peptidyl moiety" means a monovalent peptide.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The terms "numbered with reference to" or "corresponding to," when used in the context of the numbering of a given amino acid or polynucleotide sequence, refer to the numbering of the residues of a specified reference sequence when the given amino acid or polynucleotide sequence is compared to the reference sequence. An amino acid residue in a protein "corresponds" to a given residue when it occupies the same essential structural position within the protein as the given residue. One skilled in the art will immediately recognize the identity and location of residues corresponding to a specific position in a protein (e.g., ROR-1) in other proteins with different numbering systems. For example, by performing a simple sequence alignment with a protein (e.g., ROR-1) the identity and location of residues corresponding to specific positions of said protein are identified in other protein sequences aligning to said protein.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (website at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment.

The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

"Selective" or "selectivity" or the like of a compound refers to the compound's ability to discriminate between molecular targets (e.g. a compound having selectivity toward HMT SUV39H1 and/or HMT G9a).

"Specific", "specifically", "specificity", or the like of a compound refers to the compound's ability to cause a particular action, such as inhibition, to a particular molecular target with minimal or no action to other proteins in the cell (e.g. a compound having specificity towards ROR-1) displays inhibition of the activity of ROR1 whereas the same compound displays little-to-no inhibition of other ROR proteins such as ROR2).

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Typically a specific or selective reaction will be at least twice background signal or noise and more typically more than 10 to 100 times background.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *Spodoptera*) and human cells. Cells may be useful when they are naturally nonadherent or have been treated not to adhere to surfaces, for example by trypsinization.

A "stem cell" is a cell characterized by the ability of self-renewal through mitotic cell division and the potential to differentiate into a tissue or an organ. Among mammalian stem cells, embryonic stem cells (ES cells) and somatic stem cells (e.g., HSC) can be distinguished. Embryonic stem cells reside in the blastocyst and give rise to embryonic tissues, whereas somatic stem cells reside in adult tissues for the purpose of tissue regeneration and repair. A "neural stem cell" as provided herein refers to a stem cell capable to self-renew through mitotic cell division and to differentiate into a neural cell (e.g., glia cell, neuron, astrocyte, oligodendrocyte).

"B Cells" or "B lymphocytes" refer to their standard use in the art. B cells are lymphocytes, a type of white blood cell (leukocyte), that develops into a plasma cell (a "mature B cell"), which produces antibodies. An "immature B cell" is a cell that can develop into a mature B cell. Generally, pro-B cells undergo immunoglobulin heavy chain rearrangement to become pro B pre B cells, and further undergo immunoglobulin light chain rearrangement to become an immature B cells. Immature B cells include T1 and T2 B cells.

"T cells" or "T lymphocytes" as used herein are a type of lymphocyte (a subtype of white blood cell) that plays a central role in cell-mediated immunity. They can be distinguished from other lymphocytes, such as B cells and natural killer cells, by the presence of a T-cell receptor on the cell surface. T cells include, for example, natural killer T (NKT) cells, cytotoxic T lymphocytes (CTLs), regulatory T (Treg) cells, and T helper cells. Different types of T cells can be distinguished by use of T cell detection agents.

A "memory T cell" is a T cell that has previously encountered and responded to its cognate antigen during prior infection, encounter with cancer or previous vaccination. At a second encounter with its cognate antigen memory T cells can reproduce (divide) to mount a faster and stronger immune response than the first time the immune system responded to the pathogen.

A "regulatory T cell" or "suppressor T cell" is a lymphocyte which modulates the immune system, maintains tolerance to self-antigens, and prevents autoimmune disease.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation). A "ROR1 inhibitor" is a compound that negatively affects (e.g. decreases) the activity or function of ROR1 relative to the activity or function of ROR1 in the absence of the inhibitor. The terms "ROR-1 inhibitor" and "ROR-1 antagonist" are used interchangeably throughout and have the same meaning as defined herein.

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The terms "disease" or "condition" refer to a state of being or health status of a patient or subject capable of being treated with the compounds or methods provided herein. The disease may be a cancer. The disease may be an autoimmune disease. The disease may be an inflammatory disease. The disease may be an infectious disease. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "inflammatory disease" refers to a disease or condition characterized by aberrant inflammation (e.g. an increased level of inflammation compared to a control such as a healthy person not suffering from a disease). Examples of inflammatory diseases include autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis.

As used herein, the term "cancer" refers to all types of cancer, neoplasm or malignant tumors found in mammals (e.g. humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

As used herein, the terms "metastasis," "metastatic," and "metastatic cancer" can be used interchangeably and refer to the spread of a proliferative disease or disorder, e.g., cancer, from one organ or another non-adjacent organ or body part. "Metastatic cancer" is also called "Stage IV cancer." Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

A "chemotherapeutic agent" as used herein refers to a molecule (e.g. compound, peptide, protein, nucleic acid, 0103) used to treat cancer through destruction or inhibition of cancer cells or tissues. Chemotherapeutic agent agents may be selective for certain cancers or certain tissues. In embodiments, chemotherapeutic agents herein may include epigenetic inhibitors and multi-kinase inhibitors.

"Chemotherapeutic" or "chemotherapeutic agent" is used in accordance with its plain ordinary meaning and refers to a chemical composition (e.g. compound, drug, antagonist, inhibitor, modulator) or compound having antineoplastic properties or the ability to inhibit the growth or proliferation of cells. In some embodiments, a chemotherapeutic agent is an agent identified herein having utility in methods of treating cancer. In some embodiments, a chemotherapeutic agent is an agent approved by the FDA or similar regulatory agency of a country other than the USA, for treating cancer. Examples of chemotherapeutic agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, melphalan), ethylenimine and methylmelamines (e.g., hexamethylmelamine, thiotepa), alkyl sulfonates (e.g., busulfan), nitrosoureas (e.g., carmustine, lomustine, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxuridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaliplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin;

cytarabine ocfosfate; cytolytic factor; cytostatin; daclix-imab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stemcell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin;

mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, Inanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*Pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

A "ROR1 antagonist" refers to a compound (e.g. compounds described herein) that reduces the activity of ROR1 when compared to a control, such as absence of the compound or a compound with known inactivity.

The terms "cirmtuzumab", "UC-961", and "99961.1" are used herein interchangeably and refer to a humanized monoclonal antibody capable of binding the extracellular domain of the human receptor tyrosine kinase-like orphan receptor 1 (ROR-1). In embodiments, cirmtuzumab is any one of the antibodies or fragments thereof disclosed in U.S. patent application Ser. No. 14/422,519, which is incorporated by reference herein in its entirety and for all purposes.

The term "paclitaxel" also known as taxol or the like, refers in the usual and customary sense, to the compound identified by CAS Registry number 33069-62-4.

The term "docetaxel" also known as "DTX", "DXL", "Taxotere" and "Docecad" or the like, refers in the usual and customary sense, to the compound identified by CAS Registry number 114977-28-5.

The term "epirubicin" also known as "Ellence" or the like, refers in the usual and customary sense, to the compound identified by CAS Registry number 56420-45-2.

The term "doxorubicin" also known as "Adriamycin" or the like, refers in the usual and customary sense, to the compound identified by CAS Registry number 23214-92-8.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being.

The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

The term "prevent" refers to a decrease in the occurrence of disease symptoms in a patient. As indicated above, the prevention may be complete (no detectable symptoms) or partial, such that fewer symptoms are observed than would likely occur absent treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

Cancer model organism, as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

As defined herein, the term "activation", "activate", "activating", "activator" and the like in reference to a protein-inhibitor interaction means positively affecting (e.g. increasing) the activity or function of the protein relative to the activity or function of the protein in the absence of the activator. In embodiments activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "modulator" refers to a composition that increases or decreases the level of a target molecule or the function of a target molecule or the physical state of the target of the molecule relative to the absence of the modulator. In some embodiments, a ROR1 associated disease modulator is a compound that reduces the severity of one or more symptoms of a disease associated with ROR1 (e.g. cancer, inflammatory disease, autoimmune disease, or infectious disease). A ROR1 modulator is a compound that increases or decreases the activity or function or level of activity or level of function of ROR1.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease (e.g. a protein associated disease, a cancer associated with ROR1 activity, ROR1 associated cancer, ROR1 associated disease (e.g., cancer, inflammatory disease, autoimmune disease, or infectious disease)) means that the disease (e.g. cancer, inflammatory disease, autoimmune disease, or infectious disease) is caused by (in whole or in part), or a symptom of the disease is caused by (in whole or in part) the substance or substance activity or function. For example, a cancer associated with ROR1 activity or function may be a cancer that results (entirely or partially) from aberrant ROR1 function (e.g. enzyme activity, protein-protein interaction, signaling pathway) or a cancer wherein a particular symptom of the disease is caused (entirely or partially) by aberrant ROR1 activity or function. As used herein, what is described as being associated with a disease, if a causative agent, could be a target for treatment of the disease. For example, a cancer associated with ROR1 activity or function or a ROR1 associated disease (e.g., cancer, inflammatory disease, autoimmune disease, or infectious disease), may be treated with a ROR1 modulator or ROR1 inhibitor, in the instance where increased ROR1 activity or function (e.g. signaling pathway activity) causes the disease (e.g., cancer, inflammatory disease, autoimmune disease, or infectious disease). For example, an inflammatory disease associated with ROR1 activity or function or an ROR1 associated inflammatory disease, may be treated with an ROR1 modulator or ROR1 inhibitor, in the instance where increased ROR1 activity or function (e.g. signaling pathway activity) causes the disease.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components. For example, binding of ROR1 with a compound as described herein may reduce the level of a product of the ROR1 catalyzed reaction or the level of a downstream derivative of the product or binding may reduce the interactions between the ROR1 enzyme or an ROR1 reaction product and downstream effectors or signaling pathway components, resulting in changes in cell growth, proliferation, or survival.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

A "synergistic amount" as used herein refers to the sum of a first amount (e.g., an amount of a compound provided herein) and a second amount (e.g., a therapeutic agent) that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of the compound administered in combination where the measured effect is greater than the sum of the individual effects of each of the compounds provided herein administered alone as a single agent.

In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the compound provided herein when used separately from the therapeutic agent. In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the therapeutic agent when used separately from the compound provided herein.

The term "EC50" or "half maximal effective concentration" as used herein refers to the concentration of a molecule (e.g., antibody, chimeric antigen receptor or bispecific antibody) capable of inducing a response which is halfway between the baseline response and the maximum response after a specified exposure time. In embodiments, the EC50 is the concentration of a molecule (e.g., antibody, chimeric antigen receptor or bispecific antibody) that produces 50% of the maximal possible effect of that molecule.

II. Methods

The methods provided herein are, inter alia, useful for the treatment of cancer. In embodiments, the methods and compositions as described herein provide effective treatment for chemoresistant cancers expressing ROR-1. Applicants have surprisingly discovered that expression of ROR-1 is increased in cancer cells following treatment with chemotherapy. Further, Applicants show that ROR-1 expression enhances the capacity of cancer cells to metastasize and survive chemotherapy treatment resulting in chemoresistance. Applicants describe herein how coadministration of a ROR-1 antagonist (e.g., a ROR-1 antibody) and a chemotherapeutic agent (e.g., paclitaxel) is more effective than treatment with either alone and therefore effectively treats cancer (e.g., breast cancer).

In an aspect is provided, a method of treating a chemoresistant cancer in a subject in need thereof, the method including administering to the subject a therapeutically effective amount of a chemotherapeutic agent and a therapeutically effective amount of a tyrosine kinase-like orphan receptor 1 (ROR-1) antagonist, thereby treating a chemoresistant cancer in the subject.

In another aspect is provided a method of treating breast cancer in a subject in need thereof, the method including administering to said subject a therapeutically effective amount of a chemotherapeutic agent and a therapeutically effective amount of a tyrosine kinase-like orphan receptor 1 (ROR-1) antagonist, thereby treating breast cancer in the subject. In embodiments, the breast cancer is chemoresistant breast cancer.

The term "ROR-1" as used herein refers to the any of the recombinant or naturally-occurring forms of tyrosine kinase-like orphan receptor 1 (ROR-1) or variants or homologs thereof that maintain ROR-1 activity (e.g., within at least 50%, 80%, 90%, 95%, 96%, 97%, 98%, 99% or 100% activity compared to ROR-1). In some aspects, the variants or homologs have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring ROR-1 protein. In embodiments, the ROR-1 protein is substantially identical to the protein identified by Accession No. NP_005003.1 or a variant or homolog having substantial identity thereto.

In the instance where the ROR-1 antagonist is an antibody, the antibody specifically binds to a ROR-1 polypeptide. Thus, in embodiments, the ROR-1 antagonist is an anti-ROR-1 antibody. In embodiments, the anti-ROR-1 antibody is a humanized antibody.

The anti-ROR-1 antibody may include amino acid sequences (e.g., CDRs) allowing it to bind portions of a ROR-1 polypeptide or a fragment thereof. Therefore, in embodiments, the antibody includes a humanized heavy chain variable region and a humanized light chain variable region, wherein the humanized heavy chain variable region includes the sequences set forth in SEQ ID NO:1, SEQ ID NO:2, and SEQ ID NO:3; and wherein the humanized light chain variable region includes the sequences set forth in SEQ ID NO:4, SEQ ID NO:5, and SEQ ID NO:6.

In embodiments, the antibody is cirmtuzumab. Cirmtuzumab as defined herein is also referred to herein as UC-961 or 99961.1 and these terms are used interchangeably throughout. The development and structure of cirmtuzumab is disclosed in U.S. patent application Ser. No. 14/422,519 which is incorporated by reference herein in its entirety and for all purposes. In embodiments, cirmtuzumab (i.e., 99961.1, UC-961) includes a humanized heavy chain variable region and a humanized light chain variable region, wherein the humanized heavy chain variable region includes the sequences set forth in SEQ ID NO:1, SEQ ID NO:2, and SEQ ID NO:3; and wherein the humanized light chain variable region includes the sequences set forth in SEQ ID NO:4, SEQ ID NO:5, and SEQ ID NO:6.

In embodiments, the antibody includes a humanized heavy chain variable region and a humanized light chain variable region, wherein the humanized heavy chain variable region includes the sequences set forth in SEQ ID NO:7, SEQ ID NO:8, and SEQ ID NO:9; and wherein the humanized light chain variable region includes the sequences set forth in SEQ ID NO:10, SEQ ID NO: 11, and SEQ ID NO:12. An antibody including the amino acid sequences (i.e., CDRs) set forth by SEQ ID NOs:7, 8, 9, 10, 11, 12 may be referred to herein as antibody D10. The development and use of antibody D10 is disclosed in U.S. Pat. No. 9,217,040 which is incorporated by reference herein in its entirety and for all purposes.

In embodiments, the antibody binds to amino acids 130-160 of ROR-1 or a fragment thereof. In embodiments, the antibody binds a peptide including a glutamic acid at a position corresponding to position 138 of ROR-1. In embodiments, the antibody specifically binds either the 3' or middle Ig-like region of the extracellular domain of the ROR-1 protein. In embodiments, the antibody binds the 3' end of the Ig-like region of the extracellular domain of ROR-1 protein from position 1-147.

In embodiments, the antibody inhibits metastasis. In embodiments, the antibody is an antibody fragment. In embodiments, the antibody is human. In embodiments, the antibody is humanized. In embodiments, the antibody is a chimeric antibody. In embodiments, the antibody is a single chain antibody.

In embodiments, the antibody has a binding affinity of about 500 pM to about 6 nM. In embodiments, the antibody has a binding affinity of about 550 pM to about 6 nM. In embodiments, the antibody has a binding affinity of about 600 pM to about 6 nM. In embodiments, the antibody has a binding affinity of about 650 pM to about 6 nM. In embodiments, the antibody has a binding affinity of about 700 pM to about 6 nM. In embodiments, the antibody has a binding affinity of about 750 pM to about 6 nM. In embodiments, the antibody has a binding affinity of about 800 pM to about 6 nM. In embodiments, the antibody has a binding affinity of about 850 pM to about 6 nM. In embodiments, the antibody has a binding affinity of about 900 pM to about 6 nM. In embodiments, the antibody has a binding affinity of about 950 pM to about 6 nM. In embodiments, the antibody has a binding affinity of about 1 nM to about 6 nM. In embodiments, the antibody has a binding affinity of about 1 nM to about 6 nM. In embodiments, the antibody has a binding affinity of about 1.5 nM to about 6 nM. In embodiments, the antibody has a binding affinity of about 2 nM to about 6 nM. In embodiments, the antibody has a binding affinity of about 2.5 nM to about 6 nM. In embodiments, the antibody has a binding affinity of about 3 nM to about 6 nM. In embodiments, the antibody has a binding affinity of about 3.5 nM to about 6 nM. In embodiments, the antibody has a binding affinity of about 4 nM to about 6 nM. In embodiments, the antibody has a binding affinity of about 4.5 nM to about 6 nM. In embodiments, the antibody has a binding affinity of about 5 nM to about 6 nM. In embodiments, the antibody has a binding affinity of about 5.5 nM to about 6 nM.

In embodiments, the antibody has a binding affinity of 500 pM to 6 nM. In embodiments, the antibody has a binding affinity of 550 pM to 6 nM. In embodiments, the antibody has a binding affinity of 600 pM to 6 nM. In embodiments, the antibody has a binding affinity of 650 pM to 6 nM. In embodiments, the antibody has a binding affinity of 700 pM to 6 nM. In embodiments, the antibody has a binding affinity of 750 pM to 6 nM. In embodiments, the antibody has a binding affinity of 800 pM to 6 nM. In embodiments, the antibody has a binding affinity of 850 pM to 6 nM. In embodiments, the antibody has a binding affinity of 900 pM to 6 nM. In embodiments, the antibody has a binding affinity of 950 pM to 6 nM. In embodiments, the antibody has a binding affinity of 1 nM to 6 nM. In embodiments, the antibody has a binding affinity of 1 nM to 6 nM. In embodiments, the antibody has a binding affinity of 1.5 nM to 6 nM. In embodiments, the antibody has a binding affinity of 2 nM to 6 nM. In embodiments, the antibody has a binding affinity of 2.5 nM to 6 nM. In embodiments, the antibody has a binding affinity of 3 nM to 6 nM. In embodiments, the antibody has a binding affinity of 3.5 nM to 6 nM. In embodiments, the antibody has a binding affinity of 4 nM to 6 nM. In embodiments, the antibody has a binding affinity of 4.5 nM to 6 nM. In embodiments, the antibody has a binding affinity of 5 nM to 6 nM. In embodiments, the antibody has a binding affinity of 5.5 nM to 6 nM.

In embodiments, the antibody has a binding affinity of about 500 pM to about 5.5 nM. In embodiments, the antibody has a binding affinity of about 500 pM to about 5 nM. In embodiments, the antibody has a binding affinity of about 500 pM to about 4.5 nM. In embodiments, the antibody has a binding affinity of about 500 pM to about 4 nM. In embodiments, the antibody has a binding affinity of about 500 pM to about 3.5 nM. In embodiments, the antibody has a binding affinity of about 500 pM to about 3 nM. In embodiments, the antibody has a binding affinity of about 500 pM to about 3.5 nM. In embodiments, the antibody has a binding affinity of about 500 pM to about 3 nM. In embodiments, the antibody has a binding affinity of about 500 pM to about 2.5 nM. In embodiments, the antibody has a binding affinity of about 500 pM to about 2 nM. In embodiments, the antibody has a binding affinity of about 500 pM to about 1.5 nM. In embodiments, the antibody has a binding affinity of about 500 pM to about 1 nM. In embodiments, the antibody has a binding affinity of about 500 pM to about 950 pM. In embodiments, the antibody has a binding affinity of about 500 pM to about 900 pM. In embodiments, the antibody has a binding affinity of about 500 pM to about 850 pM. In embodiments, the antibody has a binding affinity of about 500 pM to about 800 pM. In embodiments, the antibody has a binding affinity of about 500 pM to about 750 pM. In embodiments, the antibody has a binding affinity of about 500 pM to about 700 pM. In embodiments, the antibody has a binding affinity of about 500 pM to about 650 pM. In embodiments, the antibody has a binding affinity of about 500 pM to about 600 pM. In embodiments, the antibody has a binding affinity of about 500 pM to about 550 pM.

In embodiments, the antibody has a binding affinity of 500 pM to 5.5 nM. In embodiments, the antibody has a binding affinity of 500 pM to 5 nM. In embodiments, the antibody has a binding affinity of 500 pM to 4.5 nM. In embodiments, the antibody has a binding affinity of 500 pM to 4 nM. In embodiments, the antibody has a binding affinity of 500 pM to 3.5 nM. In embodiments, the antibody has a binding affinity of 500 pM to 3 nM. In embodiments, the antibody has a binding affinity of 500 pM to 3.5 nM. In embodiments, the antibody has a binding affinity of 500 pM to 3 nM. In embodiments, the antibody has a binding affinity of 500 pM to 2.5 nM. In embodiments, the antibody has a binding affinity of 500 pM to 2 nM. In embodiments, the antibody has a binding affinity of 500 pM to 1.5 nM. In embodiments, the antibody has a binding affinity of 500 pM to 1 nM. In embodiments, the antibody has a binding affinity of 500 pM to 950 pM. In embodiments, the antibody has a binding affinity of 500 pM to 900 pM. In embodiments, the antibody has a binding affinity of 500 pM to 850 pM. In embodiments, the antibody has a binding affinity of 500 pM to 800 pM. In embodiments, the antibody has a binding affinity of 500 pM to 750 pM. In embodiments, the antibody has a binding affinity of 500 pM to 700 pM. In embodiments, the antibody has a binding affinity of 500 pM to 650 pM. In embodiments, the antibody has a binding affinity of 500 pM to 600 pM. In embodiments, the antibody has a binding affinity of 500 pM to 550 pM.

In embodiments, the antibody has a binding affinity of about 500 pM. In embodiments, the antibody has a binding affinity of 500 pM. In embodiments, the antibody has a binding affinity of about 550 pM. In embodiments, the antibody has a binding affinity of 550 pM. In embodiments, the antibody has a binding affinity of about 600 pM. In embodiments, the antibody has a binding affinity of 600 pM. In embodiments, the antibody has a binding affinity of about 650 pM. In embodiments, the antibody has a binding affinity of 650 pM. In embodiments, the antibody has a binding affinity of about 700 pM. In embodiments, the antibody has a binding affinity of 700 pM. In embodiments, the antibody has a binding affinity of about 750 pM. In embodiments, the antibody has a binding affinity of 750 pM. In embodiments, the antibody has a binding affinity of about 800 pM. In embodiments, the antibody has a binding affinity of 800 pM. In embodiments, the antibody has a binding affinity of about 850 pM. In embodiments, the antibody has a binding affinity of 850 pM. In embodiments, the antibody has a binding affinity of about 900 pM. In embodiments, the antibody has a binding affinity of 900 pM. In embodiments, the antibody has a binding affinity of about 950 pM. In embodiments, the antibody has a binding affinity of 950 pM. In embodiments, the antibody has a binding affinity of about 1 nM. In embodiments, the antibody has a binding affinity of about 1 nM. In embodiments, the antibody has a binding affinity of 1 nM. In embodiments, the antibody has a binding affinity of about 1.5 nM. In embodiments, the antibody has a binding affinity of 1.5 nM. In embodiments, the antibody has a binding affinity of about 2 nM. In embodiments, the antibody has a binding affinity of 2 nM. In embodiments, the antibody has a binding affinity of about 2.5 nM. In embodiments, the antibody has a binding affinity of 2.5 nM. In embodiments, the antibody has a binding affinity of about 3 nM. In embodiments, the antibody has a binding affinity of 3 nM. In embodiments, the antibody has a binding affinity of about 3.5 nM. In embodiments, the antibody has a binding affinity of 3.5 nM. In embodiments, the antibody has a binding affinity of about 4 nM. In embodiments, the antibody has a binding affinity of 4 nM. In embodiments, the antibody has a binding affinity of about 4.5 nM. In embodiments, the antibody has a binding affinity of 4.5 nM. In embodiments, the antibody has a binding affinity of about 5 nM. In embodiments, the antibody has a binding affinity of 5 nM. In embodiments, the antibody has a binding affinity of about 5.5 nM. In embodiments, the antibody has a binding affinity of 5.5 nM. In embodiments, the antibody has a binding affinity of about 6 nM. In embodiments, the antibody has a binding affinity of 6 nM.

In embodiments, the antibody binds to an ROR-1 protein with a $K_D$ of less than about 40 nM (e.g., 35, 30, 25, 20, 15, 10, 9, 8, 7, 6, 5, 4, 3, 2, 1, 0.5, 0.25, 0.1 nM). In embodiments, the antibody binds to an ROR-1 protein with a $K_D$ of less than 40 nM (e.g., 35, 30, 25, 20, 15, 10, 9, 8, 7, 6, 5, 4, 3, 2, 1, 0.5, 0.25, 0.1 nM). In embodiments, the antibody binds to an ROR-1 protein with a $K_D$ of less than about 35 nM. In embodiments, the antibody binds to an ROR-1 protein with a $K_D$ of less than 35 nM. In embodiments, the antibody binds to an ROR-1 protein with a $K_D$ of less than about 30 nM. In embodiments, the antibody binds to an ROR-1 protein with a $K_D$ of less than 30 nM. In embodiments, the antibody binds to an ROR-1 protein with a $K_D$ of less than about 25 nM. In embodiments, the antibody binds to an ROR-1 protein with a $K_D$ of less than 25 nM. In embodiments, the antibody binds to an ROR-1 protein with a $K_D$ of less than about 20 nM. In embodiments, the antibody binds to an ROR-1 protein with a $K_D$ of less than 20 nM. In embodiments, the antibody binds to an ROR-1 protein with a $K_D$ of less than about 15 nM. In embodiments, the antibody binds to an ROR-1 protein with a $K_D$ of less than 15 nM. In embodiments, the antibody binds to an ROR-1 protein with a $K_D$ of less than about 10 nM. In embodiments, the antibody binds to an ROR-1 protein with a $K_D$ of less than 10 nM. In embodiments, the antibody binds to an ROR-1 protein with a $K_D$ of less than about 9 nM. In embodiments, the antibody binds to an ROR-1 protein with a $K_D$ of less than 9 nM. In embodiments, the antibody binds to an ROR-1 protein with a $K_D$ of less than about 8 nM. In embodiments, the antibody binds to an ROR-1 protein with a $K_D$ of less than 8 nM. In embodiments, the antibody binds to an ROR-1 protein with a $K_D$ of less than about 7 nM. In embodiments, the antibody binds to an ROR-1 protein with a $K_D$ of less than 7 nM. In embodiments, the antibody binds to an ROR-1 protein with a $K_D$ of less than about 6 nM. In embodiments, the antibody binds to an ROR-1 protein with a $K_D$ of less than 6 nM. In embodiments, the antibody binds to an ROR-1 protein with a $K_D$ of less than about 5 nM. In embodiments, the antibody binds to an ROR-1 protein with a $K_D$ of less than 5 nM. In embodiments, the antibody binds to an ROR-1 protein with a $K_D$ of less than about 4 nM. In embodiments, the antibody binds to an ROR-1 protein with a $K_D$ of less than 4 nM. In embodiments, the antibody binds to an ROR-1 protein with a $K_D$ of less than about 3 nM. In embodiments, the antibody binds to an ROR-1 protein with a $K_D$ of less than 3 nM. In embodiments, the antibody binds to an ROR-1 protein with a $K_D$ of less than about 2 nM. In embodiments, the antibody binds to an ROR-1 protein with a $K_D$ of less than 2 nM. In embodiments, the antibody binds to an ROR-1 protein with a $K_D$ of less than about 1 nM. In embodiments, the antibody binds to an ROR-1 protein with a $K_D$ of less than 1 nM. In embodiments, the antibody binds to an ROR-1 protein with a $K_D$ of less than about 0.5 nM. In embodiments, the antibody binds to an ROR-1 protein with a $K_D$ of less than 0.5 nM. In embodiments, the antibody binds to an ROR-1 protein with a $K_D$ of less than about 0.25 nM. In embodiments, the antibody binds to an ROR-1 protein with a $K_D$ of less than 0.25 nM. In embodiments, the antibody binds to an ROR-1 protein with a $K_D$ of less than about 0.1 nM. In embodiments, the antibody binds to an ROR-1 protein with a $K_D$ of less than 0.1 nM.

In embodiments, the antibody is cirmtuzumab, also referred to herein as 99961.1 or UC-961. In embodiments, the antibody is D10.

In embodiments, the chemotherapeutic agent and the ROR-1 antagonist are administered in a combined synergistic amount. In embodiments, the chemotherapeutic agent and anti-ROR-1 antibody are administered in a combined synergistic amount. A "combined synergistic amount" as used herein refers to the sum of a first amount (e.g., an amount of a chemotherapeutic agent) and a second amount (e.g., an amount of a ROR-1 antagonist) that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of compounds administered in combination where the measured effect is greater than the sum of the individual effects of each of the compounds administered alone as a single agent.

In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the chemotherapeutic agent when used separately from the ROR-1 antagonist. In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the ROR-1 antagonist when used separately from the chemotherapeutic agent.

The synergistic effect may be a cell (e.g., cancer cell) division decreasing effect and/or a ROR-1 activity decreasing effect. In embodiments, synergy between the chemotherapeutic agent and the ROR-1 antagonist may result in about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% greater decrease (e.g., decrease of cell (e.g., cancer cell) division or decrease of ROR-1 activity) than the sum of the decrease of the chemotherapeutic agent or the ROR-1 antagonist when used individually and separately. In embodiments, synergy between the chemotherapeutic agent and the ROR-1 antagonist may result in 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% greater inhibition of the cell (e.g., cancer cell) division and/or the ROR-1 protein than the sum of the inhibition of the chemotherapeutic agent or the ROR-1 antagonist when used individually and separately.

The synergistic effect may be a cancer-treating effect such as a breast cancer (i.e. a breast cancer-treating synergistic effect), a lymphoma (i.e. a lymphoma-treating synergistic effect), leukemia (i.e. a leukemia-treating synergistic effect), myeloma (i.e. a myeloma-treating synergistic effect), AML (i.e. a AML-treating synergistic effect), B-ALL (i.e. a B-ALL-treating synergistic effect), T-ALL (i.e. a T-ALL-treating synergistic effect), renal cell carcinoma (i.e. a renal cell carcinoma-treating synergistic effect), colon cancer (i.e. a colon cancer-treating synergistic effect), colorectal cancer (i.e. a colorectal cancer-treating synergistic effect), epithelial squamous cell cancer (i.e., epithelial squamous cell cancer-treating synergistic effect), melanoma (i.e., melanoma-treating synergistic effect), stomach cancer (i.e. a stomach cancer-treating synergistic effect), brain cancer (i.e. a brain cancer-treating synergistic effect), lung cancer (i.e. a lung cancer-treating synergistic effect), pancreatic cancer (i.e. a pancreatic cancer-treating synergistic effect), cervical cancer (i.e. a cervical cancer-treating synergistic effect), ovarian cancer (i.e. an ovarian cancer-treating synergistic effect), liver cancer (i.e. a liver cancer-treating synergistic effect), bladder cancer (i.e. a bladder cancer-treating synergistic effect), prostate cancer (i.e. a prostate cancer-treating synergistic effect), testicular cancer (i.e. a testicular cancer-treating synergistic effect), thyroid cancer (i.e. a thyroid cancer-treating synergistic effect), head and neck cancer (i.e. a head and neck cancer-treating synergistic effect), uterine cancer (i.e. an uterine cancer-treating synergistic effect), adenocarcinoma (i.e. an adenocarcinoma-treating synergistic effect), adrenal cancer (i.e. a adrenal cancer-treating synergistic effect), chronic lymphocytic leukemia (i.e. a chronic lymphocytic leukemia-treating synergistic effect), small lymphocytic lymphoma (i.e. a small lymphocytic lymphoma-treating synergistic effect), marginal cell B-Cell lymphoma (i.e. a marginal cell B-Cell lymphoma-treating synergistic effect), Burkitt's Lymphoma (i.e. a Burkitt's Lymphoma-treating synergistic effect), and B cell leukemia (i.e. a B cell leukemia-treating synergistic effect) treating effect.

The chemotherapeutic agent and the ROR-1 antagonist may be administered in combination either simultaneously (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of the chemotherapeutic agent and the ROR-1 antagonist.

In embodiments, the chemotherapeutic agent and the ROR-1 antagonist are administered simultaneously or sequentially. In embodiments, the chemotherapeutic agent and the ROR-1 antagonist are administered simultaneously. In embodiments, the chemotherapeutic agent and the ROR-1 antagonist are administered sequentially. During the course of treatment the chemotherapeutic agent and ROR-1 antagonist may at times be administered sequentially and at other times be administered simultaneously.

In embodiments, where the chemotherapeutic agent and the ROR-1 antagonist are administered sequentially, the ROR-1 antagonist is administered at a first time point and the chemotherapeutic agent is administered at a second time point, wherein the first time point precedes the second time point. Alternatively, in embodiments, where the chemotherapeutic agent and the ROR-1 antagonist are administered sequentially, the chemotherapeutic agent is administered at a first time point and the ROR-1 antagonist is administered at a second time point, wherein the first time point precedes the second time point.

In embodiments, the chemotherapeutic agent and the anti-ROR-1 antibody are administered simultaneously or sequentially. In embodiments, the chemotherapeutic agent and the anti-ROR-1 antibody are administered simultaneously. In embodiments, the chemotherapeutic agent and the anti-ROR-1 antibody are administered sequentially. During the course of treatment the chemotherapeutic agent and anti-ROR-1 antibody may at times be administered sequentially and at other times be administered simultaneously.

In embodiments, where the chemotherapeutic agent and the anti-ROR-1 antibody are administered sequentially, the anti-ROR-1 antibody is administered at a first time point and the chemotherapeutic agent is administered at a second time point, wherein the first time point precedes the second time point. Alternatively, in embodiments, where the chemotherapeutic agent and the anti-ROR-1 antibody are administered sequentially, the chemotherapeutic agent is administered at a first time point and the anti-ROR-1 antibody is administered at a second time point, wherein the first time point precedes the second time point.

The course of treatment is best determined on an individual basis depending on the particular characteristics of the subject and the type of treatment selected. The treatment, such as those disclosed herein, can be administered to the subject on a daily, twice daily, bi-weekly, monthly or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly).

In instances where the chemotherapeutic agent and ROR-1 antagonist are administered simultaneously, the chemotherapeutic agent and ROR-1 antagonist may be administered as a mixture. Thus, in embodiments, the chemotherapeutic agent and the ROR-1 antagonist are admixed prior to administration.

In embodiments, the chemotherapeutic agent is administered at an amount of about 5 mg/kg, 10 mg/kg, 11 mg/kg, 12 mg/kg, 13 mg/kg, 14 mg/kg or 15 mg/kg. In embodiments, the chemotherapeutic agent is administered at an amount of about 5 mg/kg. In embodiments, the chemotherapeutic agent is administered at an amount of about 6 mg/kg. In embodiments, the chemotherapeutic agent is administered at an amount of about 7 mg/kg. In embodiments, the chemotherapeutic agent is administered at an amount of about 8 mg/kg. In embodiments, the chemotherapeutic agent is administered at an amount of about 9 mg/kg. In embodiments, the chemotherapeutic agent is administered at an amount of 10 mg/kg. In embodiments, the chemotherapeutic agent is administered at an amount of about 11 mg/kg. In embodiments, the chemotherapeutic agent is administered at an amount of about 12 mg/kg. In embodiments, the chemotherapeutic agent is administered at an amount of about 13 mg/kg. In embodiments, the chemotherapeutic agent is administered at an amount of about 14 mg/kg. In embodiments, the chemotherapeutic agent is administered at an amount of about 13.4 mg/kg. In a further embodiment, the chemotherapeutic agent is paclitaxel.

In embodiments, the ROR-1 antagonist is administered at an amount of about 1 mg/kg, 2 mg/kg, 3 mg/kg, 5 mg/kg or 10 mg/kg. In embodiments, the ROR-1 antagonist is administered at an amount of about 1 mg/kg. In embodiments, the ROR-1 antagonist is administered at an amount of 1 mg/kg. In embodiments, the ROR-1 antagonist is administered at an amount of about 2 mg/kg. In embodiments, the ROR-1 antagonist is administered at an amount of 2 mg/kg. In embodiments, the ROR-1 antagonist is administered at an amount of about 3 mg/kg. In embodiments, the ROR-1 antagonist is administered at an amount of 3 mg/kg. In embodiments, the ROR-1 antagonist is administered at an amount of about 5 mg/kg. In embodiments, the ROR-1 antagonist is administered at an amount of 5 mg/kg. In embodiments, the ROR-1 antagonist is administered at an amount of about 10 mg/kg. In embodiments, the ROR-1 antagonist is administered at an amount of 10 mg/kg.

In embodiments, the chemotherapeutic agent is administered at an amount of about 13 mg/kg and the ROR-1 antagonist is administered at about 2 mg/kg. In embodiments, the chemotherapeutic agent is administered at an amount of 14 mg/kg and the ROR-1 antagonist is administered at 2 mg/kg. In embodiments, the chemotherapeutic agent is administered at an amount of 13.4 mg/kg and the ROR-1 antagonist is administered at 2 mg/kg. In embodiments, the chemotherapeutic agent is administered at an amount of about 13 mg/kg and the ROR-1 antagonist is administered at about 1 mg/kg. In embodiments, the chemotherapeutic agent is administered at an amount of 14 mg/kg and the ROR-1 antagonist is administered at 1 mg/kg. In embodiments, the chemotherapeutic agent is administered at an amount of 13.4 mg/kg and the ROR-1 antagonist is administered at 1 mg/kg.

In embodiments, the chemotherapeutic agent is administered daily over the course of at least 14 days (e.g., 15, 16, 17, 18, 19, 20, 21, 22, 23, 24, 25, 26, 27, 28, 29, 30, 31, 32, 33, 34, 35, 40, 45, or 50 days). In embodiments, the chemotherapeutic agent is administered daily over the course of at least 15 days. In embodiments, the chemotherapeutic agent is administered daily over the course of at least 16 days. In embodiments, the chemotherapeutic agent is administered daily over the course of at least 17 days. In embodiments, the chemotherapeutic agent is administered daily over the course of at least 18 days. In embodiments, the chemotherapeutic agent is administered daily over the course of at least 19 days. In embodiments, the chemotherapeutic agent administered daily over the course of at least 20 days. In embodiments, the chemotherapeutic agent is administered daily over the course of at least 21 days. In embodiments, the chemotherapeutic agent is administered daily over the course of at least 22 days. In embodiments, the chemotherapeutic agent is administered daily over the course of at least 23 days. In embodiments, the chemotherapeutic agent is administered daily over the course of at least 24 days. In embodiments, the chemotherapeutic agent administered daily over the course of at least 25 days. In embodiments, the chemotherapeutic agent is administered daily over the course of at least 26 days. In embodiments, the chemotherapeutic agent is administered daily over the course of at least 27 days. In embodiments, the chemotherapeutic agent is administered daily over the course of at least 28 days. In embodiments, the chemotherapeutic agent is administered daily over the course of at least 29 days. In embodiments, the chemotherapeutic agent is administered daily over the course of at least 30 days. In embodiments, the chemotherapeutic agent is administered daily over the course of at least 31 days. In embodiments, the chemotherapeutic agent is administered daily over the course of at least 32 days. In embodiments, the chemotherapeutic agent is administered daily over the course of at least 33 days. In embodiments, the chemotherapeutic agent is administered daily over the course of at least 34 days. In embodiments, the chemotherapeutic agent is administered daily over the course of at least 35 days. In embodiments, the chemotherapeutic agent is administered daily over the course of at least 40 days. In embodiments, the chemotherapeutic agent administered daily over the course of at least 45 days. In embodiments, the chemotherapeutic agent is administered daily over the course of at least 50 days.

In embodiments, the chemotherapeutic agent is administered daily over the course of about 28 days. In embodiments, the chemotherapeutic agent is administered daily over the course of 28 days.

In embodiments, the ROR-1 antagonist is administered once over the course of about 28 days. In embodiments, the ROR-1 antagonist is administered once over the course of 28 days.

In embodiments, the chemotherapeutic agent is administered intravenously. In embodiments, the ROR-1 antagonist is administered intravenously.

In embodiments, the subject is a mammal. In embodiments, the subject is a human.

In embodiments, the method includes prior to administering detecting a level of ROR-1 in the subject. For the detection of a level of ROR-1 in the subject any method commonly used in the art to detect a protein in a biological sample is contemplated. For the detection of a level of ROR-1 any suitable biological sample derived from the subject may be used. Without limitation, a biological sample includes a tissue-derived sample, blood-derived sample, saliva-derived sample, urine-derived sample, serum-derived sample or plasma-derived sample.

Methods for detecting and identifying a level of ROR-1 (e.g., ROR-1 protein or ROR-1 RNA) involve conventional molecular biology, microbiology, and recombinant DNA techniques within the skill of the art. Such techniques are explained fully in the literature (see, e.g., Sambrook, Fritsch & Maniatis, Molecular Cloning: A Laboratory Manual, Second Edition 1989, Cold Spring Harbor Laboratory Press, Cold Spring Harbor, N.Y.; Animal Cell Culture, R. I. Freshney, ed., 1986).

The term "detecting" as provided herein includes "detecting a level of ROR-1", "detecting a level of expression of a ROR-1 protein", or "detecting an expression level of a ROR-1 RNA" and includes methods and technologies well known in the art. For example, capture arrays for expression profiling may be used to determine an expression level of a protein or an RNA. Capture arrays employ high affinity capture reagents, such as conventional antibodies, single domains, engineered scaffolds, peptides, nucleic acid aptamers or complementary nucleic acids (e.g., RNA or DNA), to bind and detect specific target ligands in high throughput manner. Antibody arrays have the required properties of specificity and acceptable background, and some are available commercially (BD Biosciences, San Jose, CA; Clontech, Mountain View, CA; BioRad; Sigma, St. Louis, MO). Antibodies for capture arrays are made either by conventional immunization (polyclonal sera and hybridomas), or as recombinant fragments, usually expressed in *E. coli*, after selection from phage or ribosome display libraries (Cambridge Antibody Technology, Cambridge, UK; BioInvent, Lund, Sweden; Affitech, Walnut Creek, CA; Biosite, San Diego, CA). In addition to the conventional antibodies, Fab and scFv fragments, single V-domains from camelids or engineered human equivalents (Domantis, Waltham, MA) are optionally useful in arrays.

Protein analytes binding to antibody arrays are detected directly or indirectly, for example, via a secondary antibody. Direct labeling is used for comparison of different samples with different colors. Where pairs of antibodies directed at the same protein ligand are available, sandwich immunoassays provide high specificity and sensitivity and are therefore the method of choice for low abundance proteins such as cytokines; they also give the possibility of detection of protein modifications. Label-free detection methods, including mass spectrometry, surface plasmon resonance and atomic force microscopy, avoid alteration of ligand. What is required from any method is optimal sensitivity and specificity, with low background to give high signal to noise. Since analyte concentrations cover a wide range, sensitivity has to be tailored appropriately. Serial dilution of the sample or use of antibodies of different affinities are solutions to this problem. Proteins of interest are frequently those in low concentration in body fluids and extracts, requiring detection in the pg range or lower, such as cytokines or the low expression products in cells.

An alternative to an array of capture molecules is one made through molecular imprinting technology, in which peptides (e.g., from the C-terminal regions of proteins) are used as templates to generate structurally complementary, sequence-specific cavities in a polymerizable matrix; the cavities can then specifically capture (denatured) proteins that have the appropriate primary amino acid sequence (ProteinPrint™, Aspira Biosystems, Burlingame, CA).

Another methodology which is useful diagnostically and in expression profiling is the ProteinChip® array (Ciphergen, Fremont, CA), in which solid phase chromatographic surfaces bind proteins with similar characteristics of charge or hydrophobicity from mixtures such as plasma or tumor extracts, and SELDI-TOF mass spectrometry is used to detection the retained proteins.

Large-scale functional chips have been constructed by immobilizing large numbers of purified proteins and are used to assay a wide range of biochemical functions, such as protein interactions with other proteins, drug-target interactions, enzyme-substrates, etc. Generally they require an expression library, cloned into *E. coli*, yeast or similar from which the expressed proteins are then purified, e.g., via a His tag and immobilized. Cell free protein transcription/translation is a viable alternative for synthesis of proteins which do not express well in bacterial or other in vivo systems.

In embodiments, the detecting includes contacting a biological sample from the subject with an anti-ROR-1 antibody and detecting binding of the anti-ROR-1 antibody to ROR-1 in the biological sample. In embodiments, the detecting includes contacting the subject with an anti-ROR-1 antibody and detecting binding of the anti-ROR-1 antibody to ROR-1 in the subject. In embodiments, the antibody is any one of the anti-ROR-1 antibodies disclosed in U.S. Pat. No. 9,217,040, which is hereby incorporated by reference in its entirety and for all purposes.

A "standard control" as referred to herein refers to a sample that serves as a reference, usually a known reference, for comparison to a test sample. For example, a test sample can be taken from a patient suspected of having cancer and compared to samples from a known cancer patient, or a known normal (non-disease) individual. A control can also represent an average value gathered from a population of similar individuals, e.g., cancer patients or healthy individuals with a similar medical background, same age, weight, etc. A control value can also be obtained from the same individual, e.g., from an earlier-obtained sample, prior to disease, or prior to treatment. One of skill will recognize that controls can be designed for assessment of any number of parameters.

One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant. In some examples of the disclosed methods, when the expression level of ROR-1 is assessed, the level is compared with a control expression level of ROR-1. By control expression level is meant the expression level of ROR-1 from a sample or subject lacking cancer, a sample or subject at a selected stage of cancer or cancer state, or in the absence of a particular variable such as a therapeutic agent (e.g., chemotherapeutic agent). Alternatively, the control level comprises a known amount of ROR-1. Such a known amount correlates with an average level of subjects lacking cancer, at a selected stage of cancer or cancer state, or in the absence of a particular variable such as a therapeutic agent. A control level also includes the expression level of ROR-1 from one or more selected samples or subjects as described herein. For example, a control level includes an assessment of the expression level of ROR-1 in a sample from a subject that does not have cancer, is at a selected stage of cancer or cancer state, or has not received treatment for cancer. Another exemplary control level includes an assessment of the expression level of ROR-1 in samples taken from multiple subjects that do not have cancer, are at a selected stage of cancer, or have not received treatment for cancer.

When the control level includes the expression level of ROR-1 in a sample or subject in the absence of a chemotherapeutic agent, the control sample or subject is optionally the same sample or subject to be tested before or after treatment with a chemotherapeutic agent or is a selected sample or subject in the absence of the therapeutic agent. Alternatively, a control level is an average expression level calculated from a number of subjects without a particular disease. A control level also includes a known control level or value known in the art.

In embodiments, the methods further include the selection of a subject expressing an increased level of ROR-1 relative to a standard control, prior to administering a therapeutically effective amount of the chemotherapeutic agent and a therapeutically effective amount of a ROR-1 antagonist. In embodiments, the method further includes prior to the administering selecting a subject expressing an increased level of ROR-1 relative to a standard control. The selected subject may be treated for cancer (e.g., breast cancer). In some embodiments, the subject is not treated for cancer (e.g., breast cancer). The subject may be part of a plurality of subjects participating in a clinical trial. Wherein the subject is part of a clinical trial, the selecting is at least in part based on the determining of an expression level of ROR-1 as provided herein. In embodiments, the subject is receiving or has been receiving chemotherapy. In embodiments, the chemoresistant cancer is a chemoresistant breast cancer. In embodiments, the subject is receiving chemotherapy. In embodiments, the subject has received chemotherapy. In further embodiments, the standard control is a level of ROR-1 detected prior to the patient receiving chemotherapy.

In embodiments, the chemotherapeutic agent is a plant alkaloid, an antitumor antibiotic, a topoisomerase inhibitor. In embodiments, the chemotherapeutic agent is a plant alkaloid. In embodiments, the chemotherapeutic agent is an antitumor antibiotic. In embodiments, the chemotherapeutic agent is a topoisomerase inhibitor. In embodiments, the chemotherapeutic agent is paclitaxel or docetaxel. In embodiments, the chemotherapeutic agent is paclitaxel. In embodiments, the chemotherapeutic agent is docetaxel. In embodiments, the chemotherapeutic agent is doxorubicin or epirubicin. In embodiments, the chemotherapeutic agent is doxorubicin. In embodiments, the chemotherapeutic agent is epirubicin.

In embodiments, the chemotherapeutic agent is not a BTK antagonist. In embodiments, the chemotherapeutic agent is not CAL101, R406 or Ibrutinib. In embodiments, the chemotherapeutic agent is not ibrutinib.

In embodiments, the ROR-1 antagonist is an antibody or a small molecule. In embodiments, the ROR-1 antagonist is an antibody. In embodiments, the ROR-1 antagonist is a small molecule. In embodiments, the ROR-1 antagonist is an anti-ROR-1 antibody.

In one embodiment, the chemoresistant cancer is breast cancer, the chemotherapeutic agent is paclitaxel, the ROR-1 antagonist is cirmtuzumab and the selected subject has received chemotherapy.

III. Pharmaceutical Compositions

The compositions including a chemotherapeutic agent and a ROR-1 antagonist as provided herein, including embodiments thereof, are further contemplated as pharmaceutical compositions. Thus, in an aspect is provided a pharmaceutical composition comprising (i) a chemotherapeutic agent selected from the group consisting of a plant alkaloid, an antitumor antibiotic and a topoisomerase inhibitor, (ii) a ROR-1 antagonist and (iii) a pharmaceutically acceptable excipient.

In another aspect is provided a pharmaceutical composition comprising (i) a chemotherapeutic agent selected from the group consisting of a plant alkaloid, an antitumor antibiotic and a topoisomerase inhibitor, (ii) an anti-ROR-1 antibody and (iii) a pharmaceutically acceptable excipient, wherein the chemotherapeutic agent and the anti-ROR-1 antibody are present in a combined synergistic amount, wherein the combined synergistic amount is effective to treat breast cancer in a subject in need thereof.

The chemotherapeutic agent and ROR-1 antagonist included in the pharmaceutical compositions provided herein may be any one of the chemotherapeutic agent and/or ROR-1 antagonists described herein including embodiments thereof. For example, the chemotherapeutic agent may be paclitaxel and the ROR-1 antagonist may be cirmtuzumab. Likewise, pharmaceutical compositions provided herein may be formulated such that the administered amount of chemotherapeutic agent and ROR-1 antagonist is any one of the amounts as described herein. For example, the paclitaxel may be present in an amount such that administration of the composition results in a dosage of 13.4 mg/kg and cirmtuzumab may be present in an amount that results in a dosage of about 2 mg/kg.

Thus, in embodiments, the chemotherapeutic agent is a plant alkaloid. In embodiments, the chemotherapeutic agent is paclitaxel. In embodiments, the ROR-1 antagonist is an antibody or a small molecule. In embodiments, the ROR-1 antagonist is an antibody. In embodiments, the ROR-1 antagonist is a small molecule. In embodiments, the ROR-1 antagonist is an anti-ROR-1 antibody. In embodiments, the antibody includes a humanized heavy chain variable region and a humanized light chain variable region, wherein the humanized heavy chain variable region includes the sequences set forth in SEQ ID NO:1, SEQ ID NO:2, and SEQ ID NO:3; and wherein the humanized light chain variable region includes the sequences set forth in SEQ ID NO:4, SEQ ID NO:5, and SEQ ID NO:6. In embodiments, the antibody is cirmtuzumab.

The provided compositions are, inter alia, suitable for formulation and administration in vitro or in vivo. Suitable carriers and excipients and their formulations are described in Remington: The Science and Practice of Pharmacy, 21st Edition, David B. Troy, ed., Lippicott Williams & Wilkins (2005). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject.

Pharmaceutical compositions provided herein include compositions wherein the active ingredient (e.g. compositions described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, the recombinant proteins described herein will contain an amount of active ingredient effective to achieve the desired result, e.g., modulating the activity of a target molecule, and/or reducing, eliminating, or slowing the progression of disease symptoms. Determination of a therapeutically effective amount of a compound of the invention is well within the capabilities of those skilled in the art, especially in light of the detailed disclosure herein.

Provided compositions can include a single agent or more than one agent. The compositions for administration will commonly include an agent as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In some embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the active compounds or constructs in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

The formulations of compounds can be presented in unit-dose or multi-dose sealed containers, such as ampules and vials. Thus, the composition can be in unit dosage form. In such form the preparation is subdivided into unit doses containing appropriate quantities of the active component. Thus, the compositions can be administered in a variety of unit dosage forms depending upon the method of administration. For example, unit dosage forms suitable for oral administration include, but are not limited to, powder, tablets, pills, capsules and lozenges.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer and severity of such symptoms), kind of concurrent treatment, complications from the disease being treated or other health-related problems. Other therapeutic regimens or agents can be used in conjunction with the methods and compounds of the invention. Adjustment and manipulation of established dosages (e.g., frequency and duration) are well within the ability of those skilled in the art.

For any composition (e.g., the cell-penetrating conjugate provided) described herein, the therapeutically effective amount can be initially determined from cell culture assays. Target concentrations will be those concentrations of active compound(s) that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred "Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

In embodiments, the pharmaceutical composition consists of paclitaxel, cirmtuzumab, and a pharmaceutically acceptable excipient. In embodiments, the pharmaceutical composition consists of docetaxel, cirmtuzumab, and a pharmaceutically acceptable excipient. In embodiments, the pharmaceutical composition consists of doxorubicin, cirmtuzumab, and a pharmaceutically acceptable excipient. In embodiments, the pharmaceutical composition consists of epirubicin, cirmtuzumab, and a pharmaceutically acceptable excipient.

In embodiments, the pharmaceutical composition includes an amount of paclitaxel equivalent to a dose of 13.4 mg/kg and an amount of cirmtuzumab equivalent to a dose of 1 mg/kg. In embodiments, the pharmaceutical composition includes an amount of paclitaxel equivalent to a dose of 13.4 mg/kg and an amount of cirmtuzumab equivalent to a dose of 2 mg/kg. In embodiments, the pharmaceutical composition includes an amount of paclitaxel equivalent to a dose of 13.4 mg/kg and an amount of cirmtuzumab equivalent to a dose of 3 mg/kg. In embodiments, the pharmaceutical composition includes an amount of paclitaxel equivalent to a dose of 13.4 mg/kg and an amount of cirmtuzumab equivalent to a dose of 5 mg/kg. In embodiments, the pharmaceutical composition includes an amount of paclitaxel equivalent to a dose of 13.4 mg/kg and an amount of cirmtuzumab equivalent to a dose of 10 mg/kg.

In embodiments, a method of treating cancer in a subject in need thereof includes administering to the subject a therapeutically effective amount of a mitotic inhibitor and a ROR-1 antagonist. In embodiments, a method of treating cancer in a patient with chemotherapy-resistant tumors includes administering to said subject a therapeutically effective amount of a mitotic inhibitor and a ROR-1 antagonist. In embodiments, a method of treating cancer in a subject in need thereof includes administering to said subject a therapeutically effective amount of a ROR-1 antibody, where the subject expresses an elevated level of ROR-1 relative to a standard control. In embodiments, the mitotic inhibitor is paclitaxel. In embodiments, the ROR-1 antagonist is cirmtuzumab. In embodiments, the cancer is breast cancer. In embodiments, a pharmaceutical composition includes a mitotic inhibitor and a ROR-1 antibody, where the mitotic inhibitor and ROR-1 antibody are present in a combined synergistic amount, where the combined synergistic amount is effective to treat cancer in a subject in need thereof.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1: Cirmtuzumab Targets ROR1+ Breast Cancer Stem Cells that are Selectively Resistant to Cancer Chemotherapy We interrogated transcriptome data of primary-breast-cancer specimens collected from patients before and after chemotherapy. We also examined the effect of chemotherapy on breast cancer patient-derived xenografts (PDX) in immune-deficient mice and assessed whether ROR1+ breast-cancer cells have activated Rho-GTPases, Hippo-YAP, or BMI1, and/or features of breast CSCs. Finally, we tested whether the humanized anti-ROR1 antibody, cirmtuzumab, had activity against breast-cancer PDX, alone or in combination with paclitaxel.

Interrogation of breast-cancer-transcriptome data revealed that tumors with high-level ROR1 had higher-level expression of genes associated with activation of Rho-GTPase Hippo-YAP, or BMI1. Tumor-cell expression of such genes and ROR1 increased after chemotherapy. Wnt5a induced ROR1-dependent activation of Rho-GTPases, YAP/TAZ, AKT, and BMI1 in Hs578T or breast-cancer patient-derived xenografts (PDX), and increased the capacity of tumor cells to invade Matrigel, form spheroids, or survive treatment with paclitaxel; these effects could be inhibited by cirmtuzumab, an anti-ROR1 mAb, which also repressed expression of genes up-regulated in $CD44\pm/CD24^{Low}$ breast cancer stem cells (CSCs), as well as genes associated with activation of Rho-GTPases, Hippo-YAP, or BMI1. Cirmtuzumab also impaired the capacity of breast-cancer cells to engraft $Rag2^{-/-}\gamma c^{-/-}$ mice or develop metastases. Finally, the combination of cirmtuzumab and paclitaxel was more effective in eradicating breast-cancer PDX than either agent alone, indicating that cirmtuzumab may improve the treatment outcome of patients with advanced breast cancer.

Expression of ROR1 and Other Genes Before and After Chemotherapy

Figure 6A:
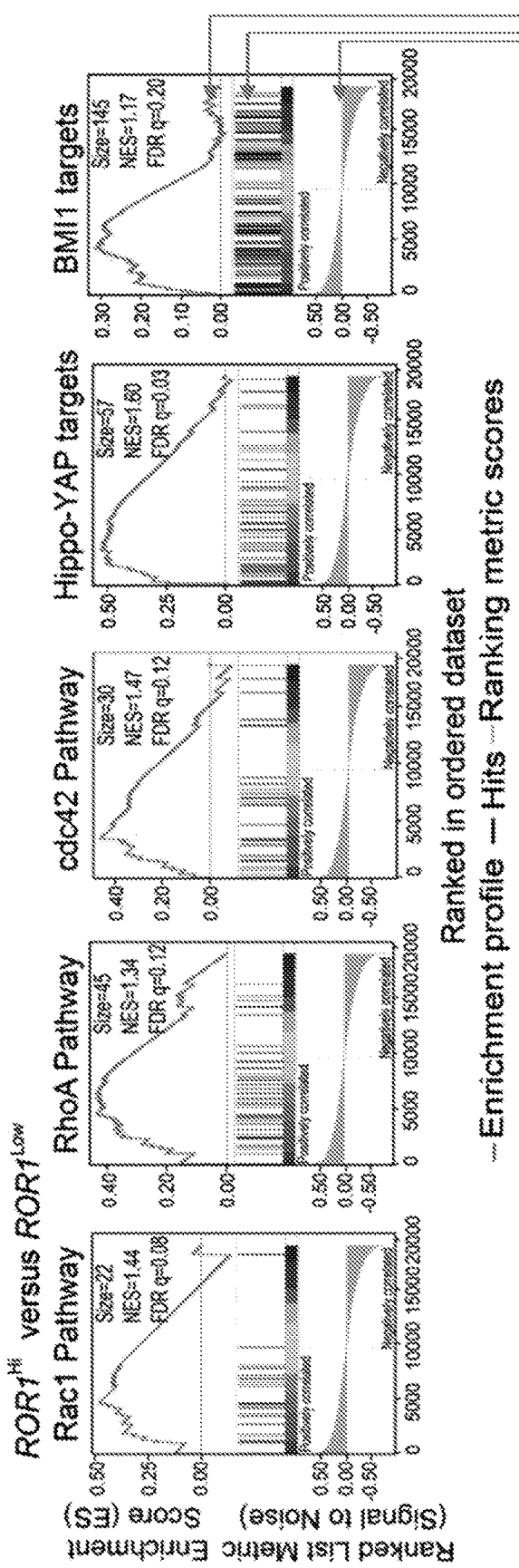
FIGS. 6A-6B. The figures show ROR1$^{Hi}$ Breast Cancers Have Higher Levels Of Genes Associated With Activation Of Rho-GTPases, Hippo-YAP, or BMI1 Than ROR1$^{Low}$ Breast Cancers.

We interrogated the PubMed Gene Expression Omnibus (GEO) database (GSE87455) on HER2-negative breast tumor biopsies prior to therapy. (Kimbung et al., 2018) We segregated the data on each specimen (N=122) into 2 subgroups based upon their relative expression of ROR1. Samples with more ROR1 transcripts than the median level were designated $ROR1^{Hi}$ (N=61), whereas tumor samples with less ROR1 were designated $ROR1^{Low}$. Gene-Set-Enrichment (GSE) analysis revealed that, relative to $ROR1^{Low}$ tumors, $ROR1^{Hi}$ tumors collectively expressed higher levels of genes associated with activation of Rho-GTPases, (Liberzon et al., 2011; Schaefer et al., 2009), Hippo-YAP, (Li et al., 2017) or BMI1, (Wiederschain et al., 2007) (FIG. 1A). Compared to $ROR1^{Low}$ tumors, $ROR1^{Hi}$ breast cancers also had higher levels of embryonic-stem-cell-associated genes with promoters bound and activated in embryonic stem-cells by Oct4 or the NOS target regulator of embryonic stem-cell identity, including a subset of NOS activation targets encoding transcription regulators (NOS TFs) (Table 1). (Ben-Porath et al., 2008) Finally, $ROR1^{Hi}$ breast-cancers had higher levels of genes that distinctively were up-regulated in $CD44+/CD24^{Low}$, or in mammosphere (MS) forming cells, relative to that of non-$CD44+/CD24^{Low}$, or all tumor cells. (Creighton et al., 2009) Similarly segregating samples described in another GEO database (GSE21974), (Stickeler et al., 2011) into $ROR1^{Hi}$ and $ROR1^{Low}$ subgroups, revealed similar associations (FIG. 6A).

The GSE87455 dataset had data on tumor tissues (N=57) obtained before (Pre) and after (Post) chemotherapy, which consisted of 4 cycles of epirubicin plus docetaxel and bevacizumab. The differences in gene-expression between matched post- and pre-treatment specimens resembled those of ROR1$^{Hi}$ verses ROR1$^{Low}$ breast cancers. Of the 34,694 genes analyzed, we identified the 1,000 most over-expressed and 1,000 most under-expressed genes in the post-treatment biopsies relative to their matched pre-treatment biopsies, or in ROR1 tumors compared to ROR1$^{Low}$ tumors. Three-hundred-sixty-five of the 1,000 most over-expressed transcripts after chemotherapy were among the 1,000 most over-expressed by ROR1$^{Hi}$ cancers relative to ROR1$^{Low}$ cancers (e.g. ALDH1A1), whereas only 3 were among the 1,000 most over-expressed by ROR1$^{Low}$ tumors relative to ROR1$^{Hi}$ tumors (p<0.0001, Fisher's exact test). Similarly, 190 of the 1,000 most under-expressed transcripts after chemotherapy also were among the 1,000 most under-expressed in ROR1$^{Hi}$ breast cancers relative to that of ROR1$^{Low}$ tumors, whereas none of these were under-expressed by ROR1$^{Low}$ tumors relative to ROR1$^{Hi}$ cancers (p<0.0001, Fisher's exact test).

Figure 1B:
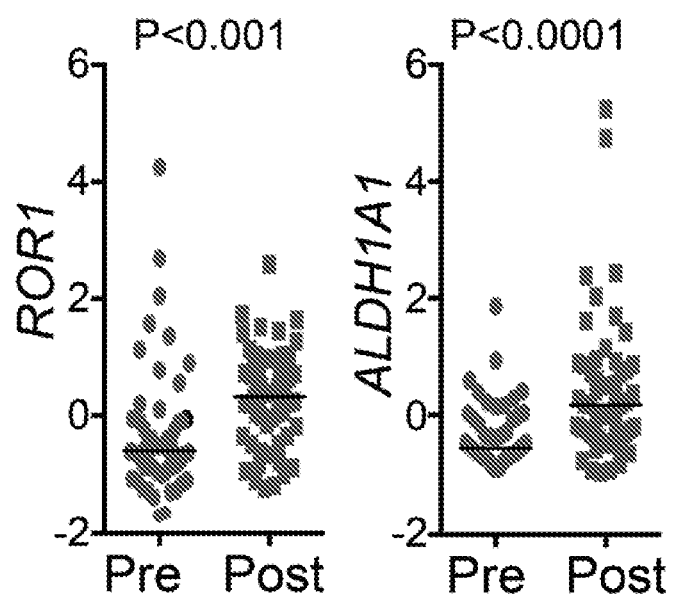
Figure 1C:
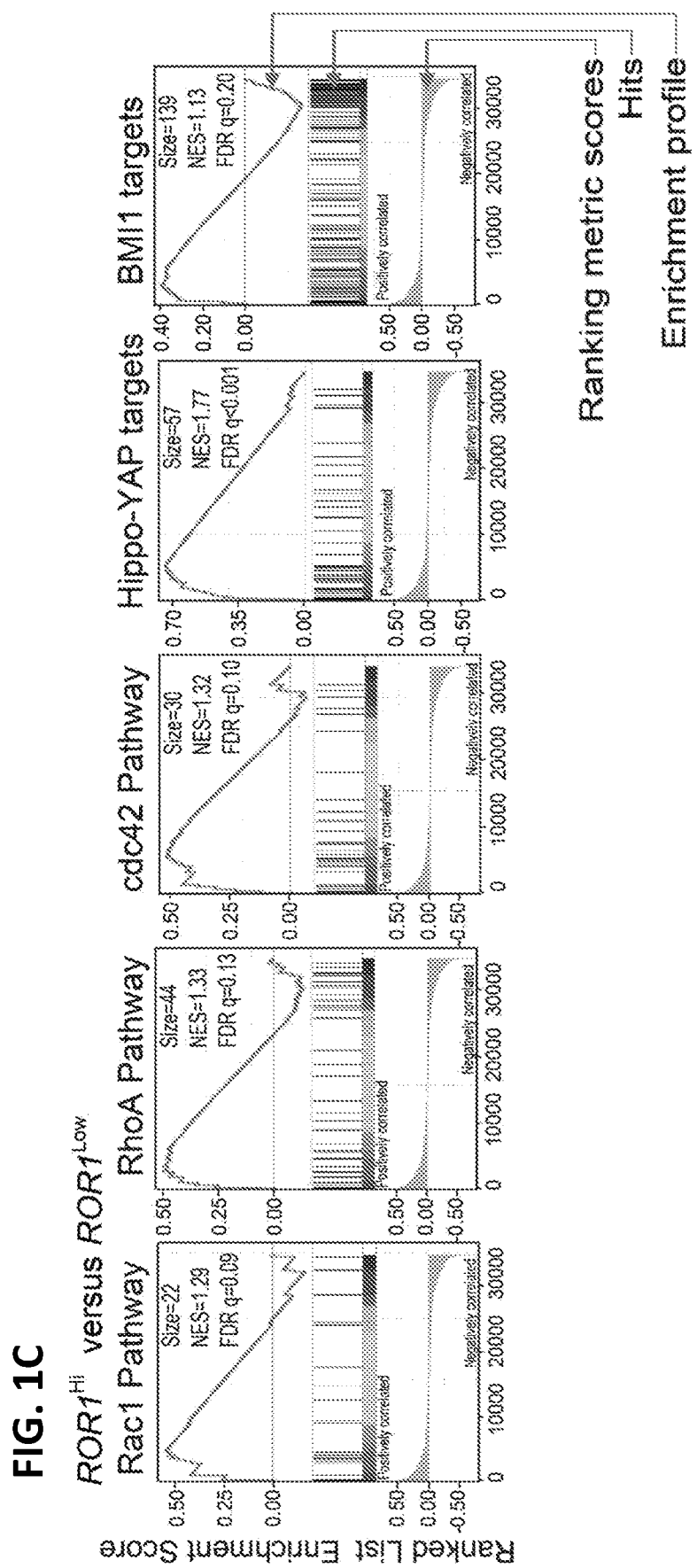
Figure 6B:
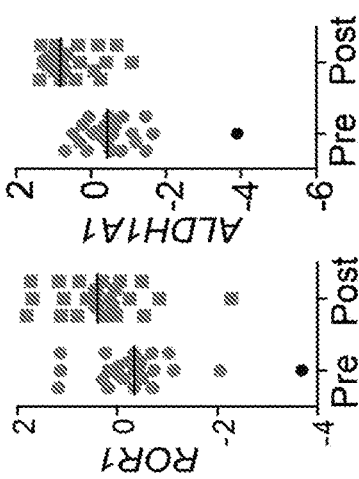

We noted that 43 (76%) of 57 post-treatment cancer biopsies described in GSE87455 expressed higher levels of ROR1, and 48 (84%) expressed higher levels of ALDH1A1, than their matched pre-treatment biopsies (FIG. 1B). Similar findings were observed for samples described in the GSE21457 (FIG. 6B). Moreover, post-treatment cancer cells had higher levels of genes associated with activation of Rho-GTPases, Hippo-YAP, or BMI1, than the pre-treatment specimens (FIG. 1C). In addition, as noted for ROR1$^{Hi}$ tumors, post-treatment breast cancer cells expressed higher levels of genes associated with embryonic stem cells or CD44$^+$/CD24$^{Low}$ CSCs (Table 1). Conversely, genes expressed at lower levels in CD44$^+$/CD24$^{Low}$ CSCs, or in MS-forming-cells, relative to that of non-CSC, or the whole-tumor population, were under-expressed in post-therapy specimens (Table 1), (Creighton et al., 2009) and over-expressed in ROR1$^{Low}$ samples relative to ROR1$^{Hi}$ tumors (Table 1). Collectively, these data imply that ROR1 is a marker for breast CSCs and/or that ROR1$^{Hi}$ tumor cells have a selective advantage with chemotherapy.

Expression of ROR1. TAZ. And BMI1 Before and After Chemotherapy

Figure 1E:
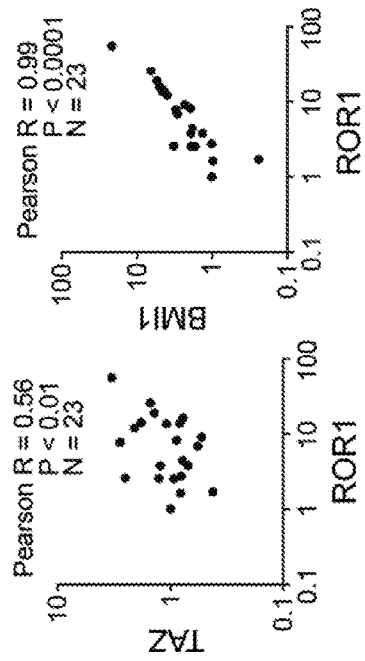
Figure 1G:
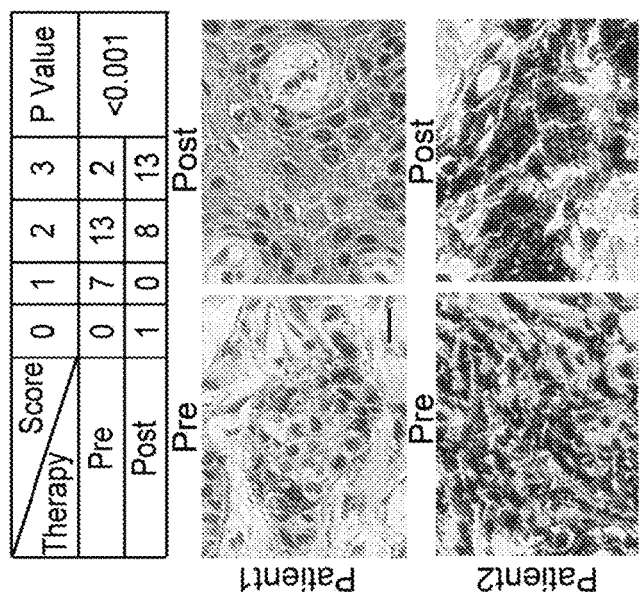
Figure 1D:
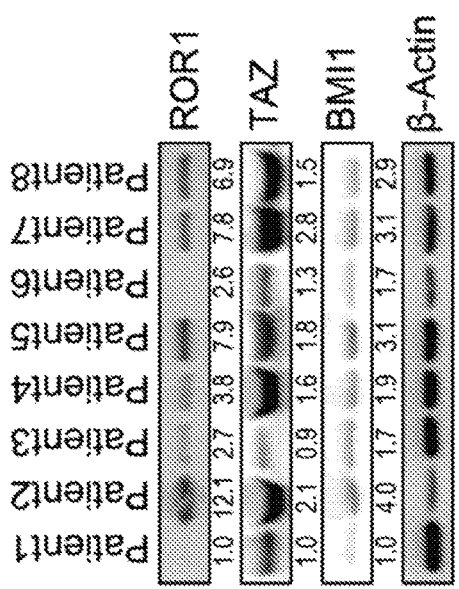

As TAZ accumulates upon activation of Hippo-YAP, (Park et al., 2015) we examined primary cancers from treatment-naïve patients (N=23) for ROR1, TAZ, and BMI1 via immunoblot. As noted, (Zhang et al., 2012a) >60% of primary breast cancers had detectable ROR1 (FIG. 1D and Table 2). Moreover, expression of ROR1 correlated with expression of TAZ (FIG. 1E, and Table 2, Pearson R=0.56, P<0.01, N=23) or BMI1 (FIGS. 1D and 1E and Table 2, Pearson R=0.99, P<0.0001, N=23).

Figure 1F:
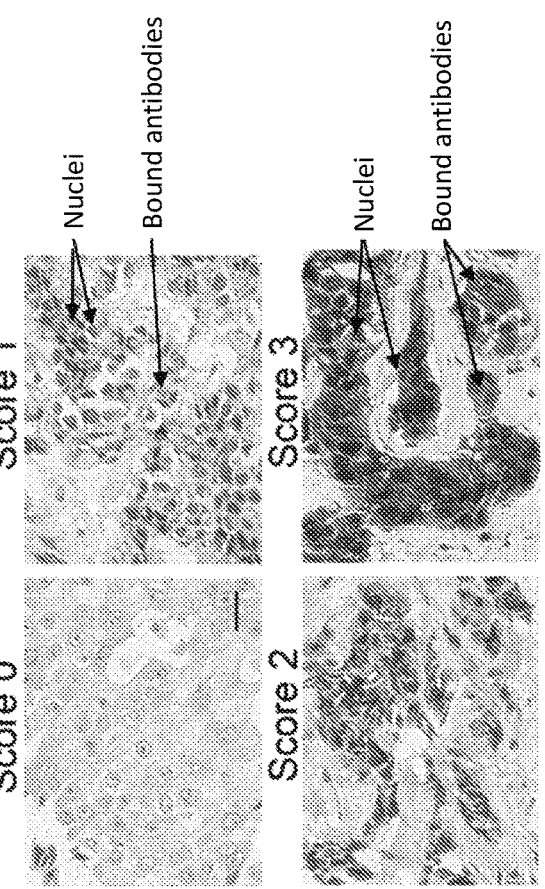

We obtained formalin-fixed, paraffin-embedded pre- and post-therapy biopsy material from patients (N=22) with invasive ductal carcinoma, who were treated with docetaxel, epirubicin, and/or cyclophosphamide, and examined for ROR1 via immunohistochemistry. Of 22-matched specimens, 14 (64%) had increased ROR1 after therapy, whereas 7 (32%) had levels of ROR1 that did not change (FIGS. 1F-1G, Table 3). Only one post-treatment specimen had lower levels of ROR1 than the pre-treatment sample (Table 3). These findings corroborate those made interrogating transcriptome data, and indicate that cancers generally become enriched for ROR1+ cells after chemotherapy.

ROR1$^+$ Breast Cancer Cells have Characteristics of Breast CSCs

Figure 7A:
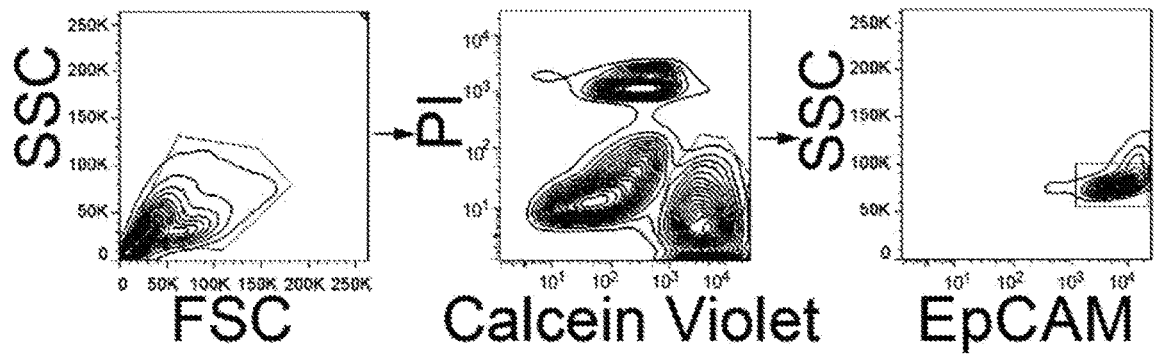
Figure 7B:
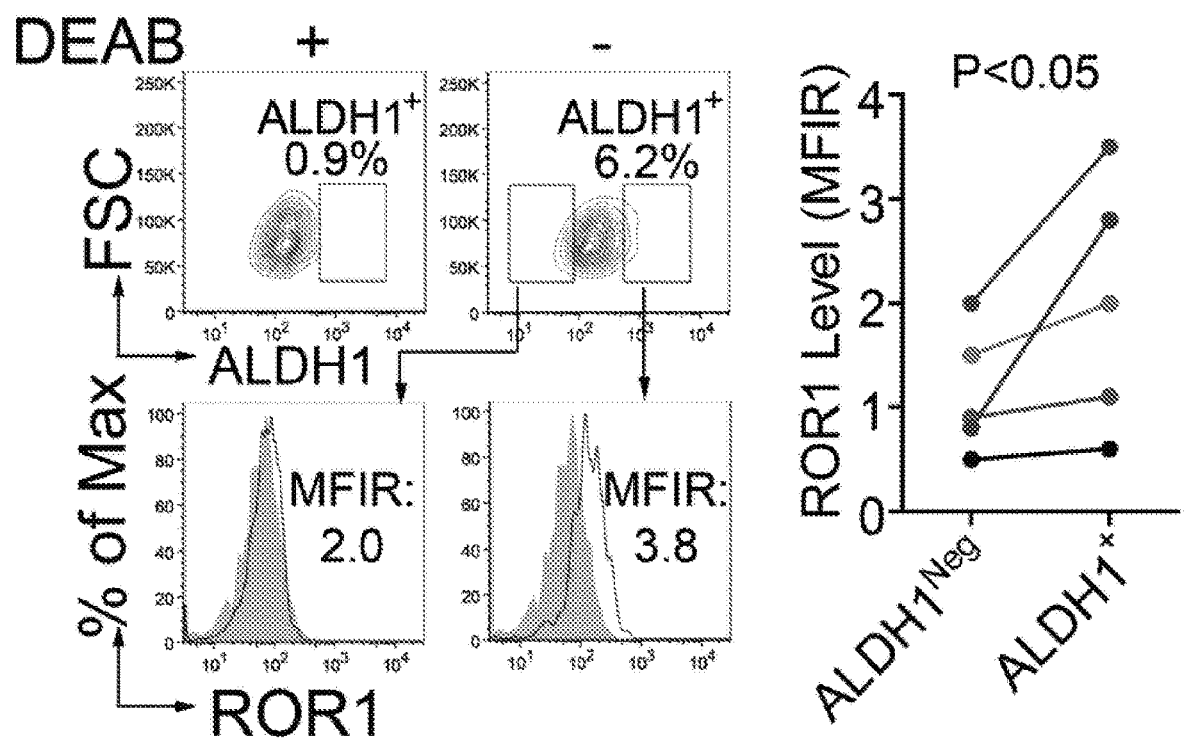
(FIG. 7B), Cells from each PDX were stained for ROR1 with 4A5 or control mAb, and for ALDO-FLUOR without (−) or with (+) the ALDH1-inhibitor, DEAB, as indicated at the top of each column of histograms. The open boxes in the each contour plot in the top row indicate the gates used for defining cells with ALDH1 activity, the proportions of which are indicated. The open boxes in the left of the contour plots depict the gates used to identify cells that assuredly lacked ALDH1 activity. In the bottom row are histograms depicting the fluorescence of cells that were negative (left) or positive (right) for ALDH1 activity. The right panel provides the staining intensity for ROR1 in ALDH1+ versus ALDH1$^{Neg}$ cells from each of the five different PDX tumors.
Figure 7C:
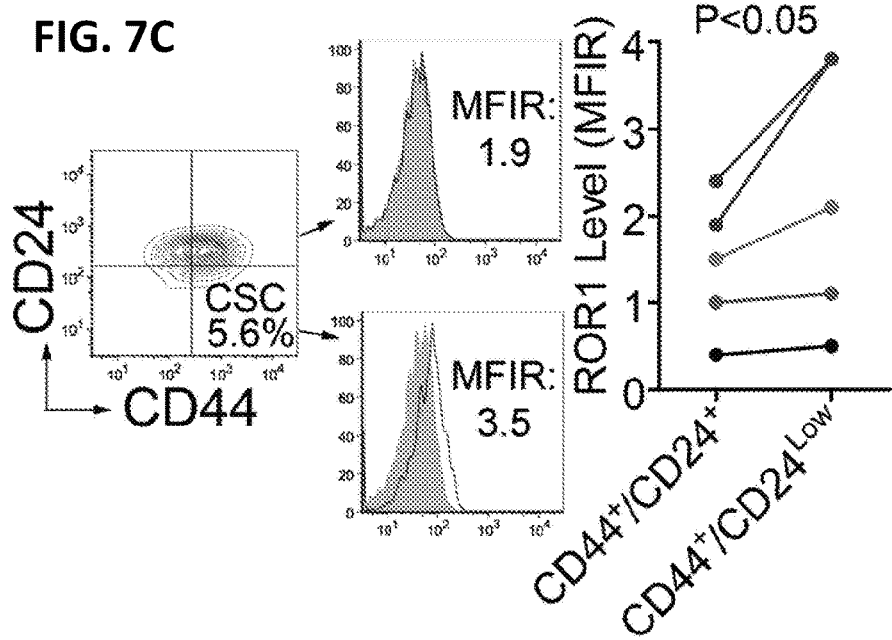
(FIG. 7C), Cells from each PDX were stained with CD44, CD24, 4A5, or a control mAb. The histograms depict the fluorescence of gated CD44+/CD24$^{Low}$ or CD44+/CD24+ cells; the shaded histograms depict the fluorescence of cells stained with an isotype-control mAb, whereas the open histograms depict the fluorescence of cells stained with 4A5. The right panel provides the ROR1 staining intensity of CD44+CD24$^{Low}$ versus CD44+CD24+ cells from each of five different PDX. The number in each plot provides the mean fluorescence intensity ratio (MFIR) for ROR1, which is derived from the mean fluorescence intensity (MFI) of cells labeled with the anti-ROR1 mAb divided by MFI of cells labeled with control antibody.
Figure 7D:
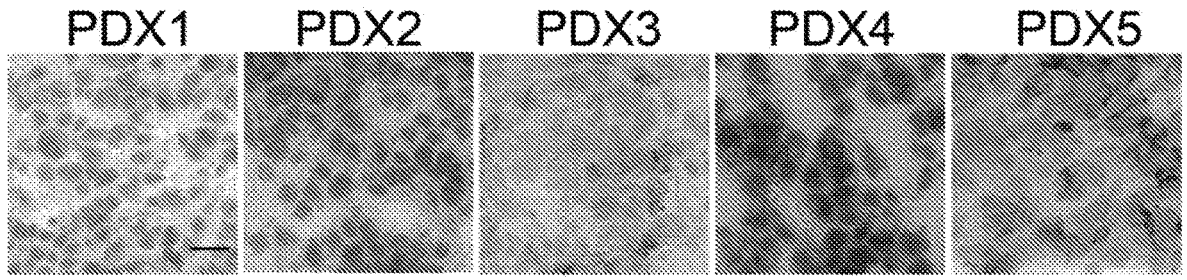
(FIG. 7D), Tissue sections of PDX1-5 were stained with 4A5 for detection of ROR1 by IHC. Scale bar: 15 µm.
Figure 7E:
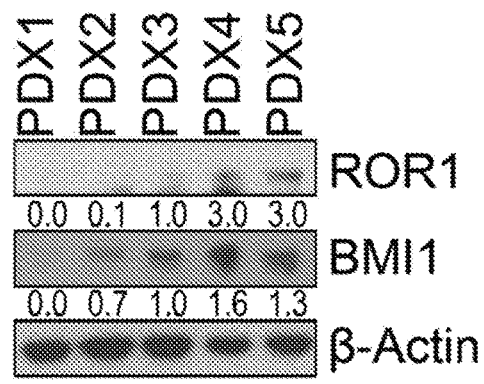
(FIG. 7E), PDX tumors were examined for ROR1 or BMI1 via immunoblot analyses.

We established breast-cancer PDX in Rag2$^{-/-}$γc$^{-/-}$ mice (Table 4). The PDX retained the heterogeneity commonly found in primary tumors, which typically have small proportions of cells with features of CSCs. For example, only 0.6% or 6.5% of the tumor cells in PDX1 or PDX4, respectively, had detectable ALDH1 enzymatic activity (Table 4). Nevertheless, such tumor cells, and tumor cells that co-expressed CD44 and low-level CD24, expressed higher levels of ROR1 than cancer cells of the same tumor that were ALDEFLUOR-negative, or that were negative for CD44 and CD24 (FIG. 7A-7C). The PDX that had the highest levels of ROR1 (PDX4 and PDX5) also had the highest levels of CSCs markers and BMI1 (FIG. 7D-7E). Furthermore, PDX with high levels of ROR1 had significantly higher levels of nuclear YAP/TAZ than cancer cells of the same PDX with low to undetectable ROR1, as assessed by confocal microscopy (FIG. 7F, P<0.05).

We found that PDX with high proportions of ROR1+ cells formed significantly greater numbers of spheroids than did the PDX with relatively few ROR1+ cells (FIG. 7G). Furthermore, the tumor cells of PDX with high-proportions of ROR1+ cells were more invasive in Matrigel than tumor cells of PDX with few ROR1+ cells (FIG. 7H).

We implanted equal numbers of tumor cells from each PDX into Rag2$^{-/-}$γc$^{-/-}$ mice and monitored engraftment. The tumors that formed using cells from PDX with high proportions of ROR1+ cells (e.g. PDX4 or PDX5) grew faster those that developed from PDX with few ROR1+ cells (e.g. PDX1 or PDX2, FIG. 2A). When the secondary PDX reached 300 mm$^3$ in size, we treated the mice with 13.4 mg/kg paclitaxel for five consecutive days and observed tumor regression (FIG. 2A). We noted that the tumors derived from PDX with high proportions of ROR1+ cells (e.g. PDX4 or PDX5) re-grew shortly after therapy, in contrast to tumors derived from PDX with few ROR1+ cells (e.g. PDX1 or PDX2, FIG. 2A).

Figure 2B:
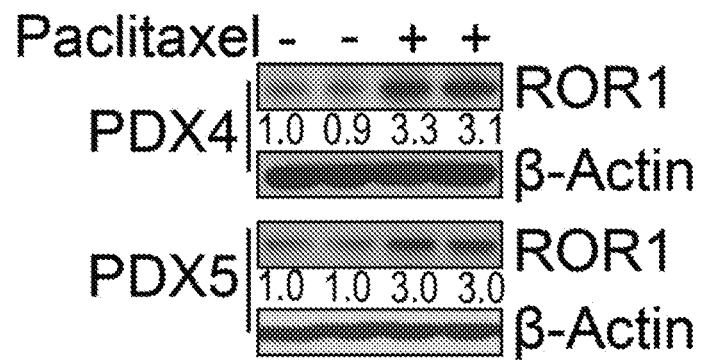
(FIG. 2B), Lysates from PDX4 or PDX5 that were isolated from untreated mice (−) or from mice that were treated with paclitaxel (+), as indicated at the top, were examined for ROR1 or 13-actin, the latter serving as a protein-loading control. Numbers below each lane are the ratios of band densities of ROR1 to 13-actin normalized to that for the PDX isolated from untreated mice.
Figure 2C:
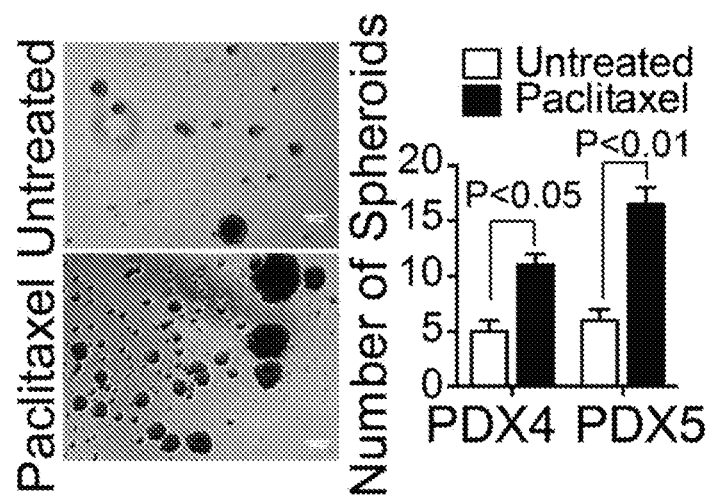
(FIG. 2C-2D), The histograms depict the average numbers of spheroids (FIG. 2C) or invading cells (FIG. 2D) from PDX4 or PDX5 extirpated from untreated mice (open bars, N=3) or mice treated paclitaxel (black bars, N=3)±SEM. Representative photomicrographs to the left of the histograms depict the spheroids or invasive cells of PDX extirpated from untreated mice, or from mice that received paclitaxel, as indicated on the left margin. Scale bar: 100 μm.
Figure 2D:
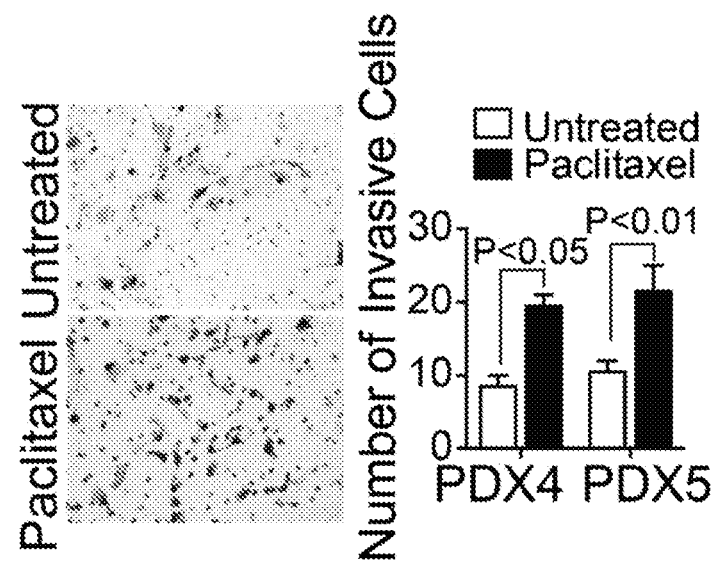
Figure 2E:
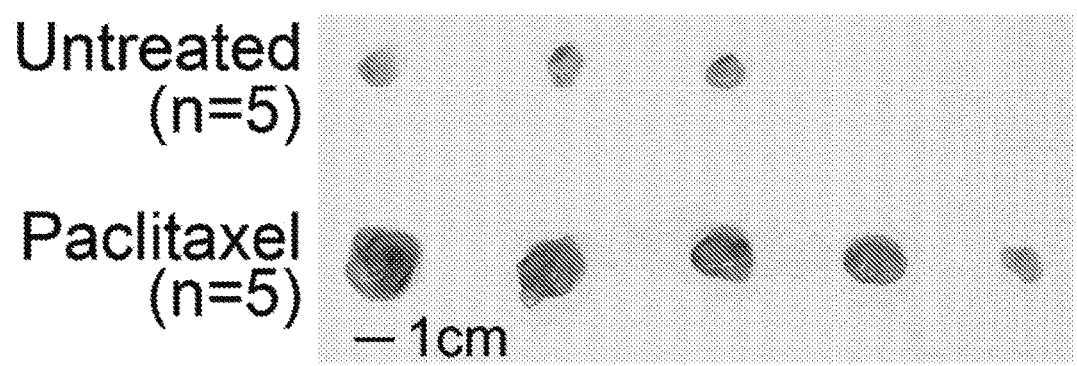
(FIG. 2E), Tumor cells were isolated from PDX4 or PDX5 from mice that did not receive treatment (Untreated) or that were treated with paclitaxel (Paclitaxel), as indicated on the left margin. Isolated tumors cells from each PDX were re-implanted into mice (N=5) and the tumor incidence was recorded. The left panel provides representative photographs for tumors isolated from untreated mice or from mice that received paclitaxel. The frequency of tumorigenic cells and the probability estimates are provided in the right panel using the Extreme Limiting Dilution Analysis (ELDA) software.
Figure 7I:
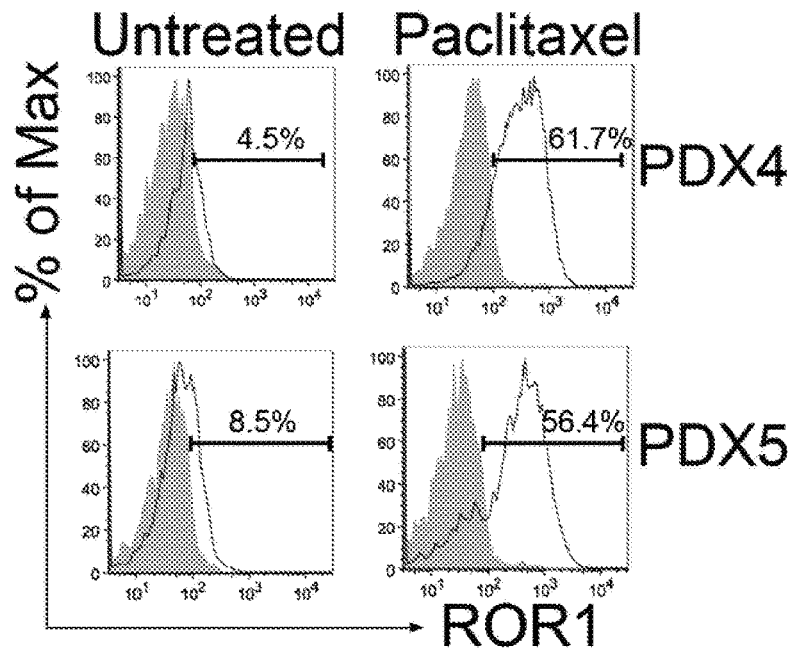
(FIG. 7I-7J) Single cell suspensions were generated from each PDX that were removed from PDX-engrafted mice that had not received treatment (Untreated), or had been treated with paclitaxel. We examined for ROR1 (FIG. 7I) or ALDH1 enzymatic activity (FIG. 7J) via flow cytometry. DEAB, an inhibitor of ALDH1 enzymatic activity, was used to identify cells that have ALDH1 activity. (I), Open histograms depict fluorescence intensity of cells stained with anti-ROR1. Shaded histograms depict fluorescence intensity of cells stained with a control antibody. The number in each histogram depicts percentage of ROR1+ cells.
Figure 7J:
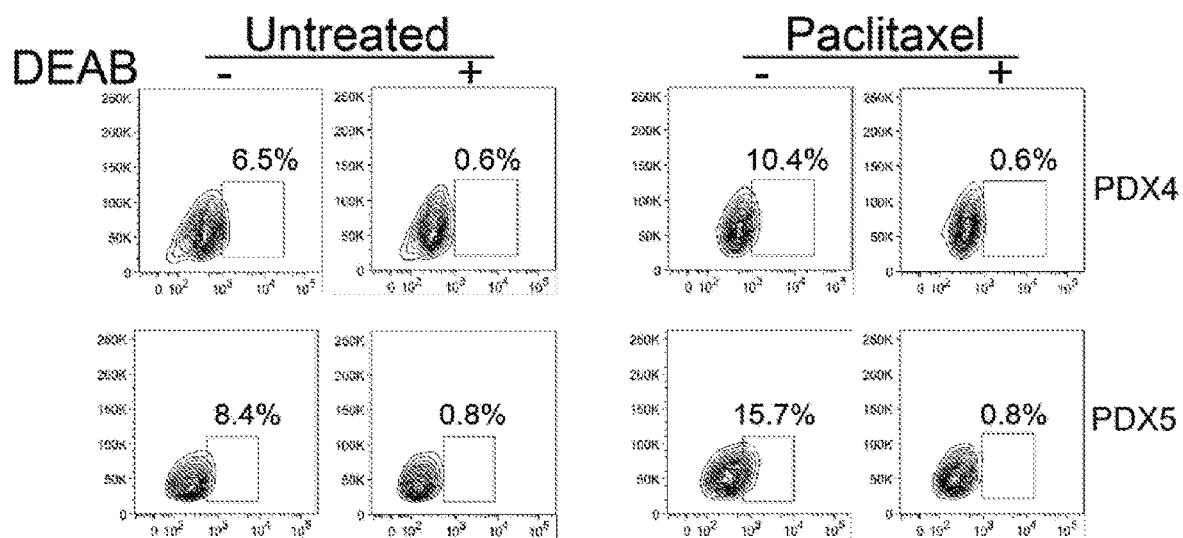

We excised the tumors derived from PDX4 or PDX5 and found that the residual tumors of mice treated with paclitaxel had higher proportions of ROR1+ cells than the matched tumors of mice that did not receive paclitaxel, or the original PDX (FIG. 2B and FIG. 7I, PDX4: 61.7%±7.0% versus 4.5%±1.1%, PDX5: 56.4%±6.4% versus 8.5%±5.8%). As noted in prior studies, (Samanta et al., 2014) the tumors of mice treated with paclitaxel also had higher proportions of ALDH1-expressing cells than the matched tumors of untreated mice or the original PDX (FIG. 7J). Finally, the tumors of mice treated with paclitaxel were enriched for cells that could form spheroids, invade Matrigel, or re-engraft Rag2$^{-/-}$γc$^{-/-}$ mice compared to matched tumors of untreated mice or the original PDX (FIG. 2C-2E).

Figure 7K:
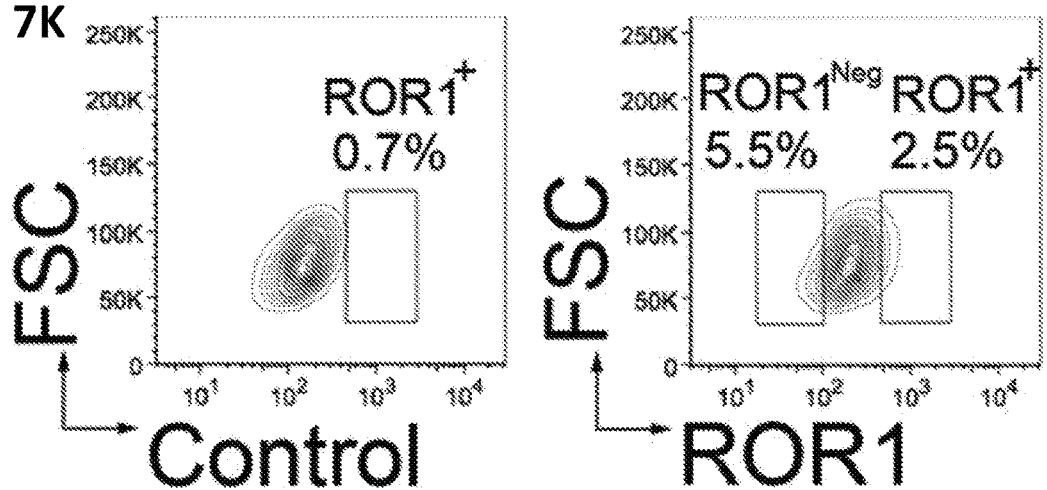
(FIG. 7K), Strategy for sorting ROR1+ versus ROR1$^{Neg}$ cells. The open boxes indicate the gates used to select ROR1$^{Neg}$ (left) or ROR1+ (right) cells.
Figure 7L:
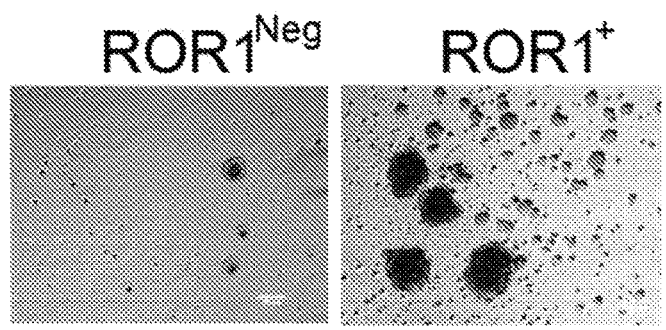
(FIG. 7L), Photomicrographs of spheroids formed from ROR1+ or ROR1$^{Neg}$ cells isolated from each of the PDX, as indicated on the top. Scale bar: 100 µm. The bar graph to the right depicts the average numbers of spheroids formed ±SEM by each of the cell preparations in three separate cultures, as indicated at the bottom of the histograms.
Figure 7L:
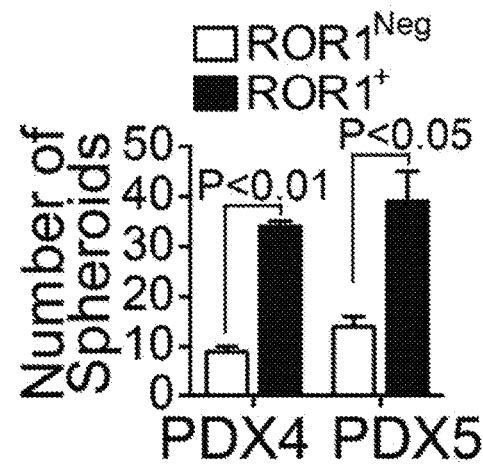
Figure 7M:
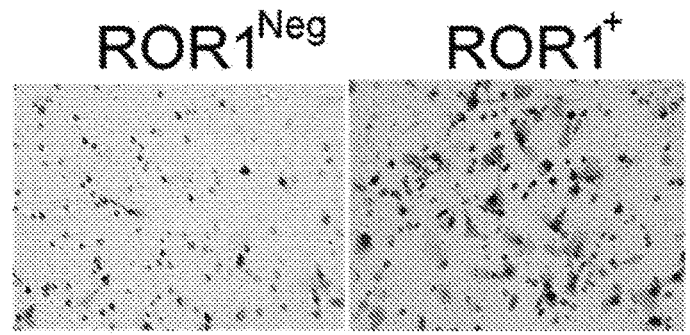
(FIG. 7M), Photomicrographs of Matrigel-invading cells from ROR1+ or ROR1$^{Neg}$ cells isolated from different PDX, as indicated on the top. Scale bar: 10 m. The bar graph to the right depicts the mean relative invasion of cells into Matrigel (±SEM) for each of the cell preparations in three independent experiments, normalized to that of the cells from PDX5.
Figure 7M:
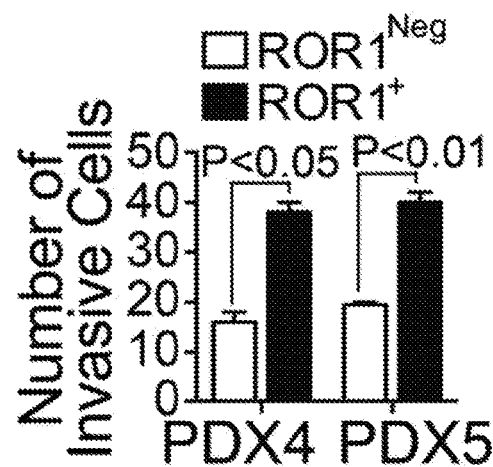

We isolated ROR1+ and ROR1$^{Neg}$ breast cancer cells from PDX4 or PDX5 via flow cytometry using 4A5 (FIG. 7K), a mAb that binds a different epitope of ROR1 than that recognized by cirmtuzumab. ROR1+ cells formed significantly greater numbers of spheroids than ROR1$^{Neg}$ cells, which formed few spheroids or none at all (FIG. 7L). Furthermore, ROR1+ cells were significantly more invasive in Matrigel than ROR1$^{Neg}$ cancer cells of the same tumor (FIG. 7M).

We performed tumorigenicity assays with limiting numbers of tumor cells from PDX4 or PDX5. Five hundred ROR1+ cells from each PDX could establish secondary PDX in most mice (FIG. 7N). In contrast, the same number of ROR1$^{Neg}$ cells did not form tumors, except in a few animals (FIG. 7N). Similarly, ALDH1+, or CD44+/CD24$^{Low}$ cells isolated from these PDX also had a significantly greater capacity to form secondary PDX than ALDH1$^{Neg}$ or CD44+/CD24+ cells of the same PDX (Table 5), as noted in prior studies. (Al-Hajj et al., 2003; Ginestier et al., 2007)

Cirmtuzumab Inhibits Wnt5a-Induced ROR1-Dependent Activation of Rho-GTPases, Hippo-YAP, and BMI1

Figure 3A:
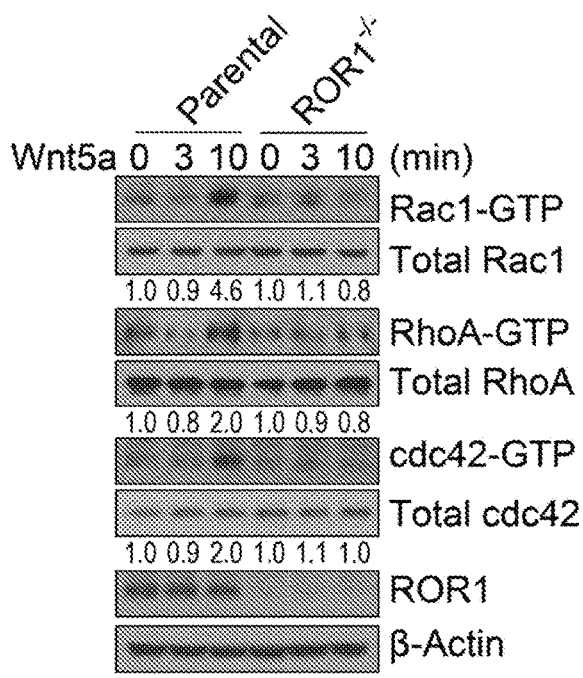
FIGS. 3A-3P. The figures show Wnt5a Induces ROR1-Dependent Activation Of Rho-GTPases, YAP/TAZ, And BMI1.
Figure 3B:
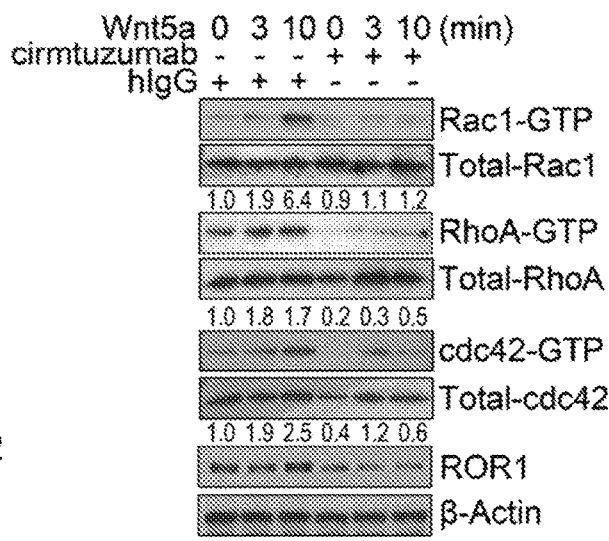
Figure 3C:
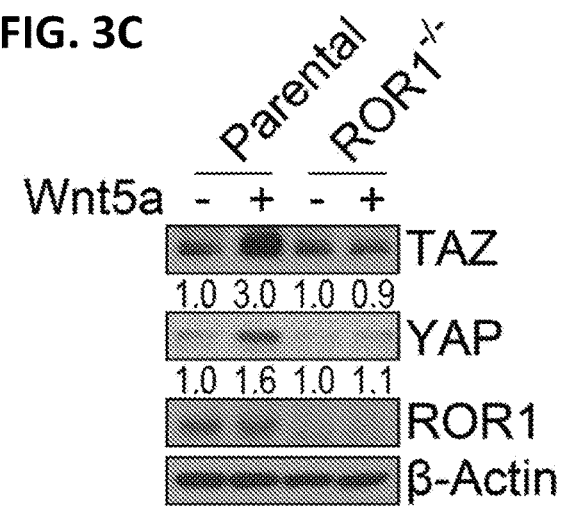
(FIG. 3C), Immunoblot analyses for proteins indicated on the right margin, using lysates from parental or ROR1−/− Hs578T that were treated without (−) or with (+) Wnt5a, as indicated on the top. The numbers below each lane are as in 3A.

We extinguished expression of ROR1 via CRISPR/Cas9 in the basal-type breast-cancer cell-line Hs578T (FIG. 3A). Exogenous Wnt5a could induce activation of Rac1, RhoA, and cdc42 within 10 minutes in wild-type Hs578T cells (wt-Hs578T), but not in ROR1−/−Hs578T cells lacking ROR1 (ROR1−/− Hs578T) (FIG. 3A). Moreover, treatment with cirmtuzumab, but not a human IgG (hIgG) of irrelevant specificity, inhibited the capacity of exogenous Wnt5a to induce activation of Rac1, RhoA, or cdc42 in wt-Hs578T cells (FIG. 3B). Treatment with Wnt5a also enhanced expression and nuclear localization of YAP/TAZ in wt-Hs578T cells, but not in ROR1−/− Hs578T (FIGS. 3C and 3D).

Figure 3F:
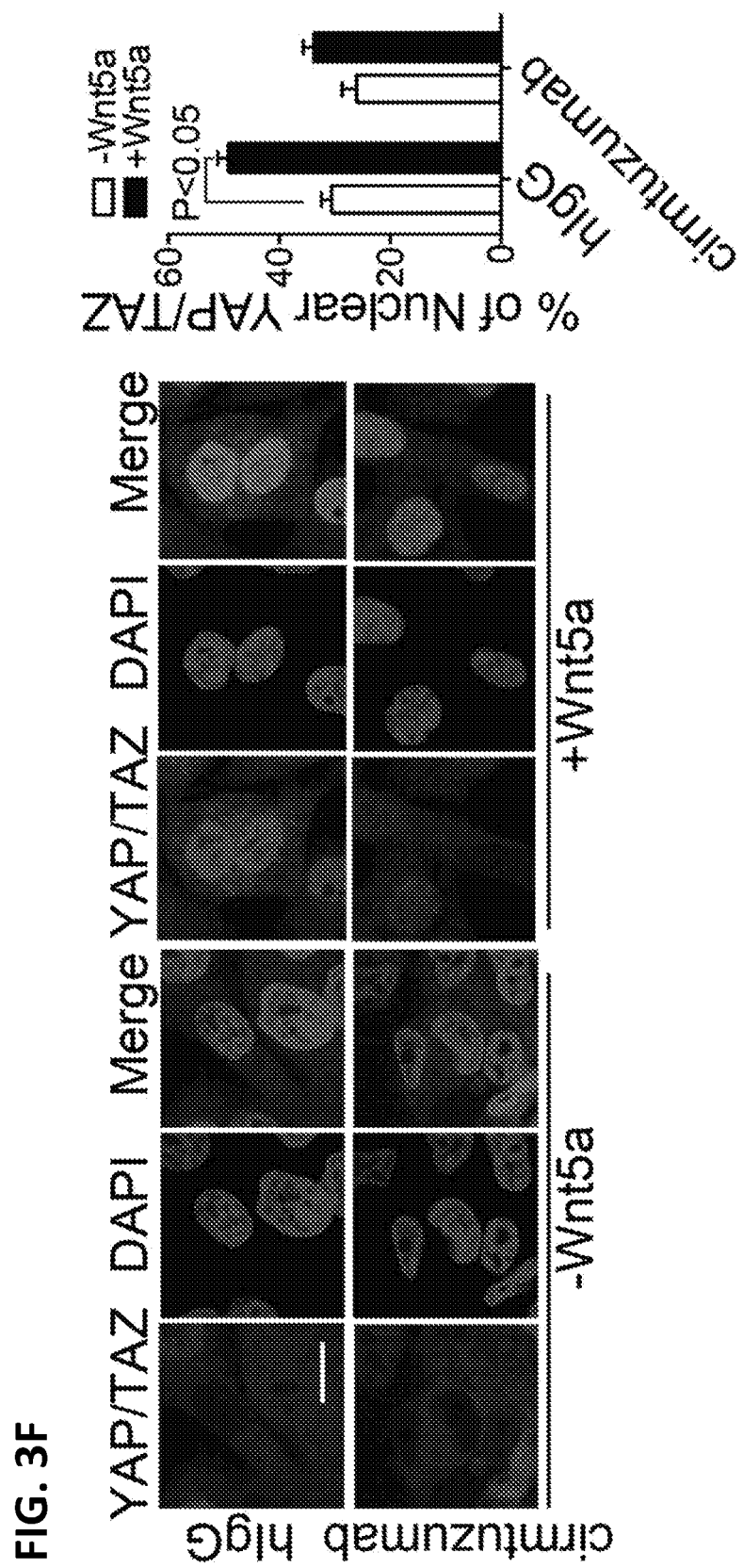
(FIG. 3F), Photomicrographs of Hs578T that were cultured overnight with cirmtuzumab or hIgG (as indicted on the left), then treated without or with Wnt5a for 4 hours (as indicated at the bottom), then stained for YAP/TAZ and DAPI (as indicated at the top), and then examined using confocal microscopy. Scale bar: 20 μm. The histogram to the right of the photomicrographs provides the average percentages of YAP/TAZ located within the nuclei of the cells in each field (N=10, ±SEM).

Treatment with cirmtuzumab also inhibited the capacity of exogenous Wnt5a to induce expression or nuclear localization of YAP/TAZ in wt-Hs578T (FIGS. 3E and 3F).

Figure 3G:
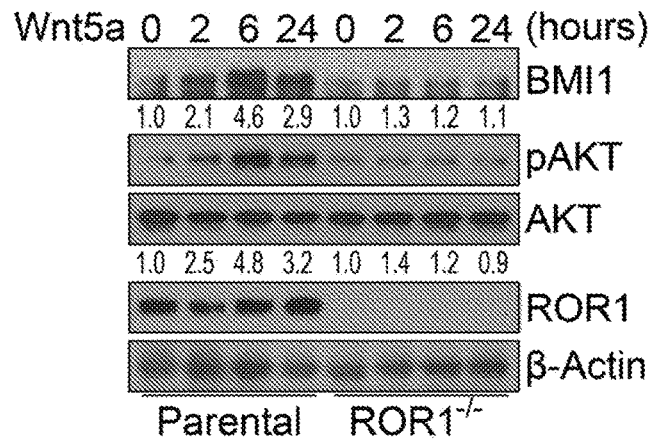
(FIG. 3G), Immunoblot analyses for proteins indicated on the right, using lysates of parental or ROR1−/− Hs578T (as indicated on the bottom), that were treated with Wnt5a for the times indicated at the top. The numbers below each lane are the ratios of band densities of BMI1 versus 13-Actin, pAKT versus total AKT, or ROR1 versus 13-Actin normalized to that of the sample collected at time 0.

Treatment with exogenous Wnt5a for two hours could enhance expression of the BMI1 protein, but not BMI1 mRNA, in wt-Hs578T cells, but not ROR1$^{−/−}$ Hs578T cells (FIG. 3G and FIG. 8A), suggesting that Wnt5a up-regulates BMI1 in a post-transcriptional manner. Consistent with this effect of Wnt5a being dependent upon ROR1, we noted that cirmtuzumab could inhibit the capacity of Wnt5a to enhance expression of BMI1 in wt-Hs578T (FIG. 3G).

Figure 3H:
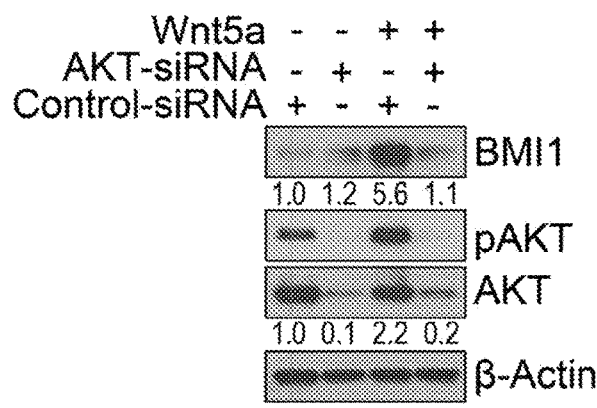
(FIG. 3H), Immunoblot analyses for proteins indicated on the right, using lysates of Hs578T that had been treated with control siRNA or AKT-specific siRNA (AKT-siRNA), as indicated on the top. The numbers below each lane are as in 3G.
Figure 3I:
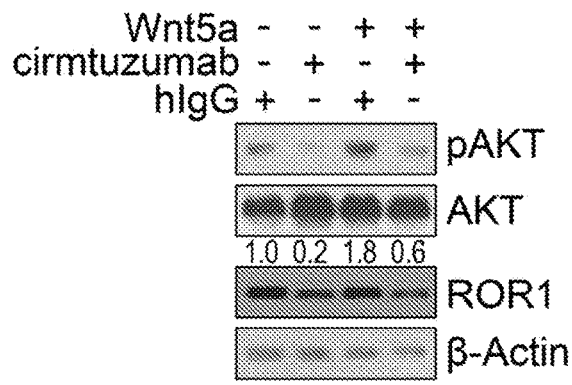
(FIG. 3I), Imunoblot analyses for proteins as indicated on the right margin, using lysates of Hs578T that had been treated overnight with hIgG or cirmtuzumab, and then treated without or with Wnt5a, as indicated at the top. The numbers below each lane are as in 3G.
Figure 3J:
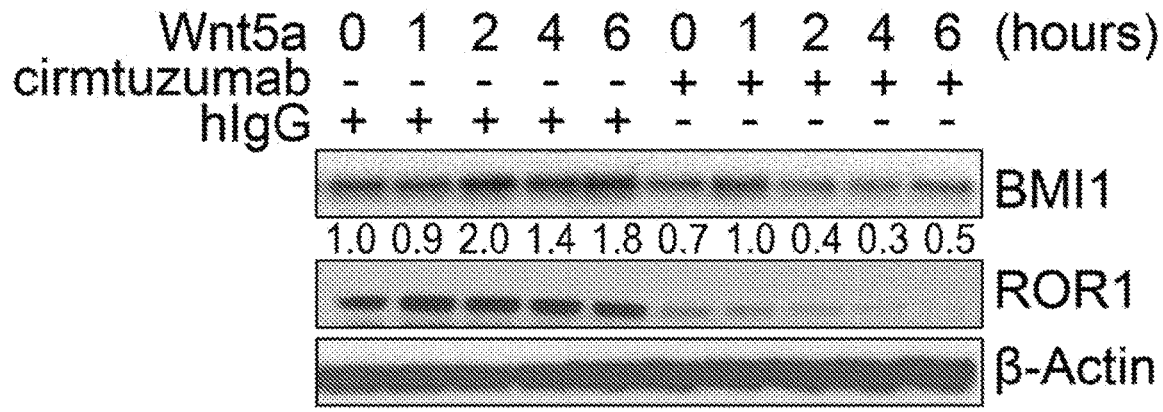
(FIG. 3J), Imunoblot analyses for proteins as indicated on the right margin, using lysates of Hs578T that had been treated overnight with hIgG or cirmtuzumab, and then treated with Wnt5a for the times indicated at the top. The numbers below each lane are as in 3G.

We examined whether treatment of Hs578T with Wnt5a could induce phosphorylation of AKT, which prior studies found could inhibit proteasomal degradation of BMI1 to promote its accumulation. (Kim et al., 2011) Wnt5a induced AKT-phosphorylation in wt-Hs578T cells, but not in ROR1$^{−/−}$ Hs578T cells (FIG. 3G). On the other hand, treatment of wt-Hs578T with small interfering RNA specific for AKT, or a small molecule inhibitor of AKT (MK-2206), impaired the capacity of Wnt5a to induce activation of AKT, and also inhibited the capacity of Wnt5a to enhance expression of BMI1 (FIG. 3H and FIG. 8B). Treatment with cirmtuzumab also inhibited the capacity of Wnt5a to induce activation of AKT or expression of BMI1 (FIG. 3I-3J), suggesting that these Wnt5a effects were dependent upon ROR1-signaling.

Figure 3K:
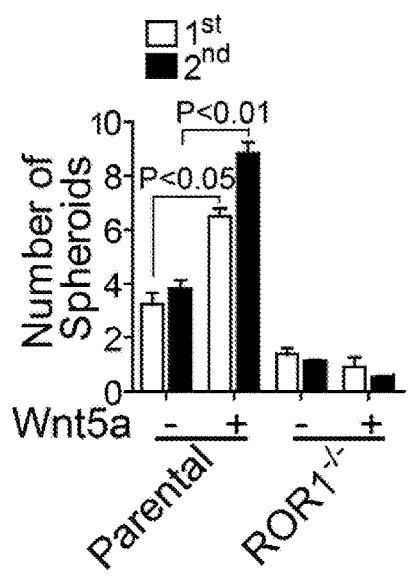
(FIG. 3K-3L), The histograms depict the average numbers of spheroids (FIG. 3K) or invasive cells (FIG. 3L) from Parental or ROR1−/− Hs578T that were treated without or with Wnt5a in triplicate ±SEM.
Figure 3L:
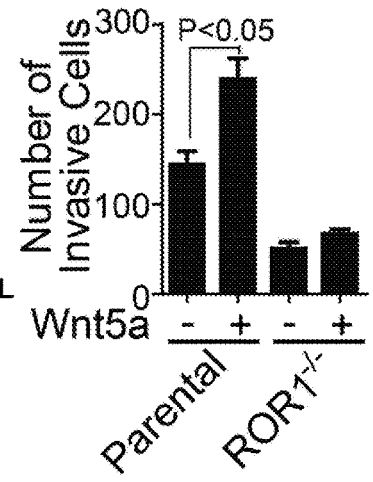
Figure 3M:
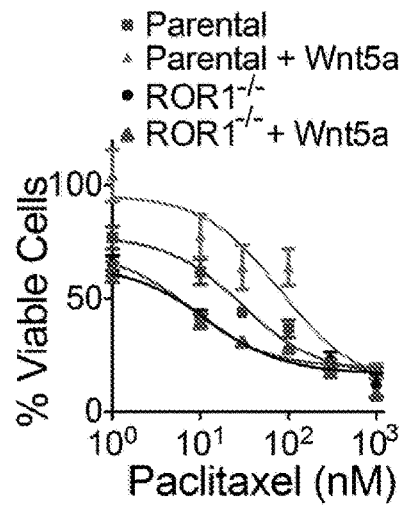
(FIG. 3M), Percent viable cells of parental or ROR1−/− Hs578T that were cultured in medium supplemented without or with Wnt5a (as indicated in the legend) and then treated with paclitaxel, at the concentrations indicated below. Data points represent the mean percentages of viable cells in triplicate wells ±SEM.

Functionally, ROR-1 Hs578T cells formed significantly fewer spheroids than wt-Hs578T cells (FIG. 3K). Also, treatment with exogenous Wnt5a could enhance invasion of wt-Hs578T cells, but not ROR1$^{−/−}$ Hs578T (FIG. 3L). Finally, ROR1$^{−/−}$ Hs578T cells were more sensitive to treatment with paclitaxel than wt-Hs578T cells. Moreover, exogenous Wnt5a could enhance the resistance of wt-Hs578T to paclitaxel, but not ROR1$^{−/−}$ Hs578T (FIG. 3M).

Figure 3N:
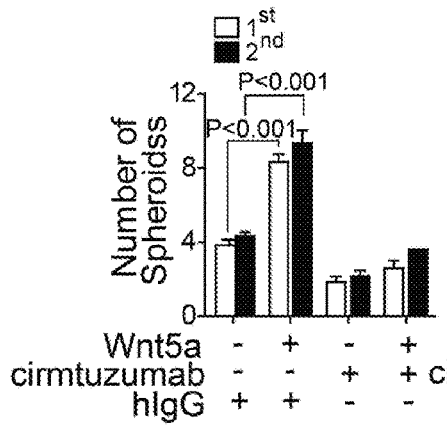
(FIG. 3N-3O), The bar graph depicts the average numbers of spheroids (FIG. 3N) or invasive cells (FIG. 3O) from Hs578T cells that were incubated with either hIgG or cirmtuzumab overnight and then treated with or without Wnt5a in three separate culture wells ±SEM. Open bars indicate the number of spheroids detected during the first passage (1st), whereas the closed bars provide those of the second passage (2nd), in three separate culture wells ±SEM.
Figure 3O:
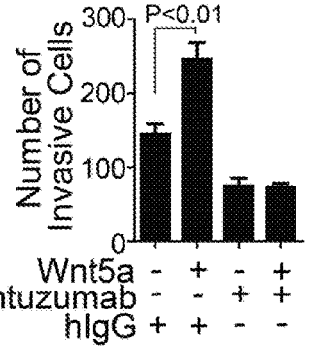
Figure 3P:
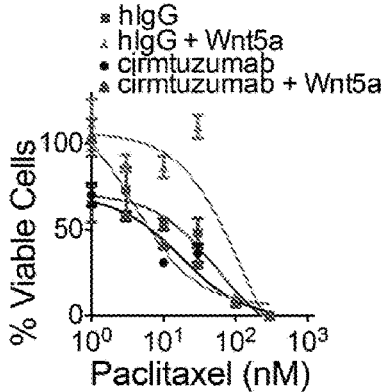

Cirmtuzumab inhibited the capacity of exogenous Wnt5a to enhance wt-Hs578T to form spheroids (FIG. 3N) or invade Matrigel (FIG. 3O). Furthermore, treatment with cirmtuzumab, but not nonspecific hIgG, enhanced the sensitivity of wt-Hs578T to paclitaxel, and inhibited the capacity of Wnt5a to enhance the resistance of wt-Hs578T to paclitaxel (FIG. 3P).

Cirmtuzumab Inhibits Re-Engraftment of Breast Cancer PDX

Figure 9A:
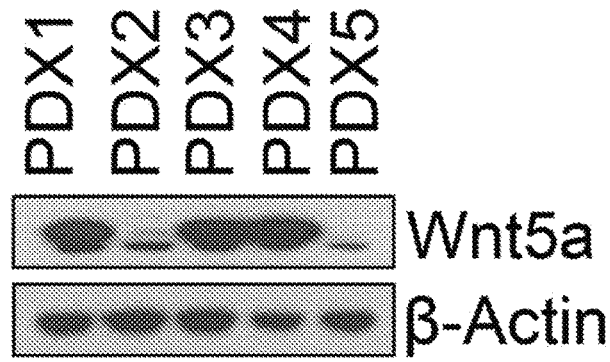
FIGS. 9A-9F. The figures show Treatment With Cirmtuzumab Could Inhibit YAP/TAZ Activity And BMI1 Expression In Vitro And Repress Tumor Growth In Vivo.
Figure 9B:
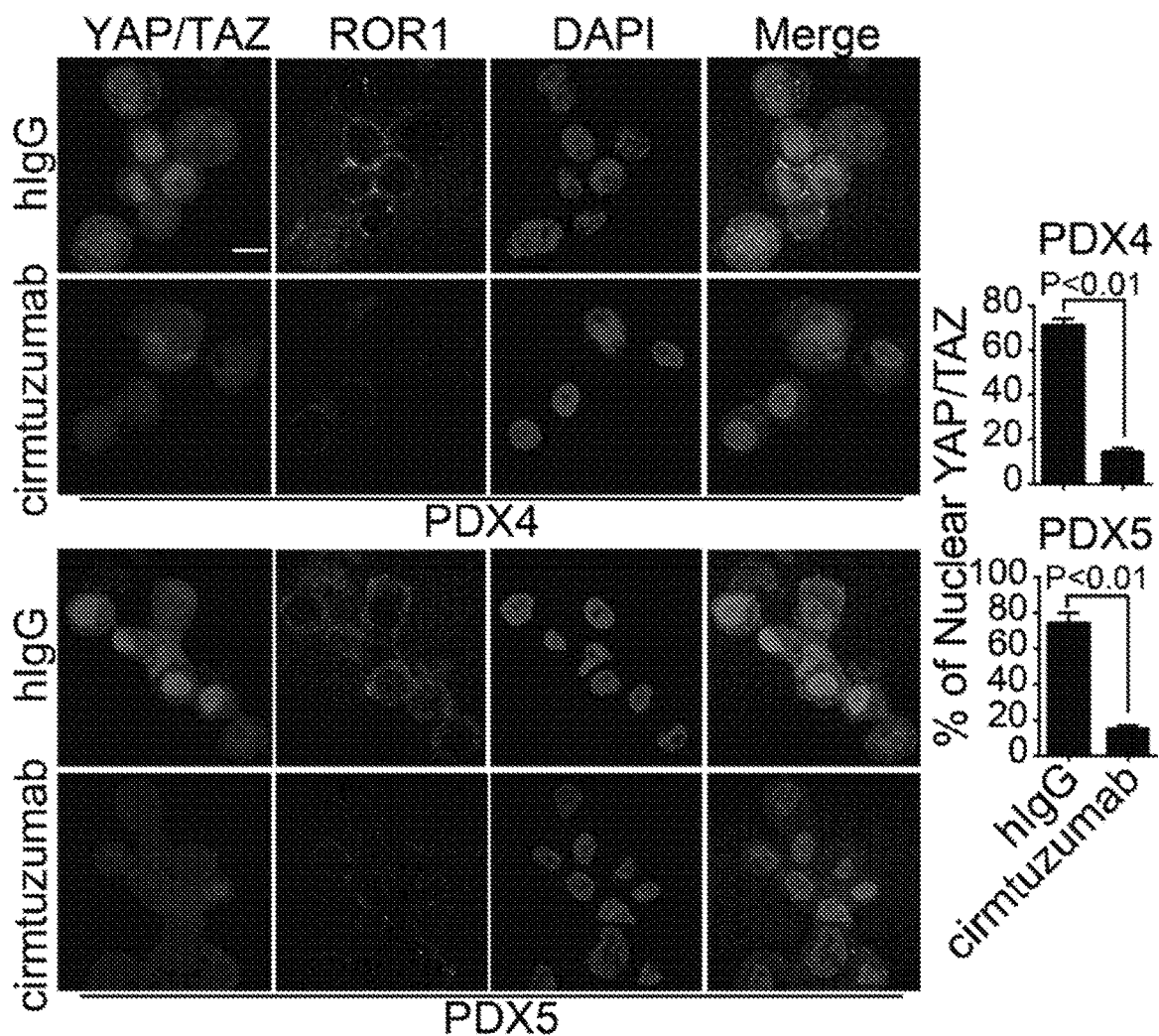

We examined the activity of cirmtuzumab on primary breast cancer cells that expressed variable levels of Wnt5a (FIG. 9A). Isolated tumor cells from each PDX were treated with cirmtuzumab at 50 g/ml for 4 hours prior to confocal microscopy. This revealed that primary breast cancer cells treated with cirmtuzumab had significantly less nuclear YAP/TAZ than tumor cells from the same PDX that were treated with a control hIgG (FIG. 9B).

Figure 4A:
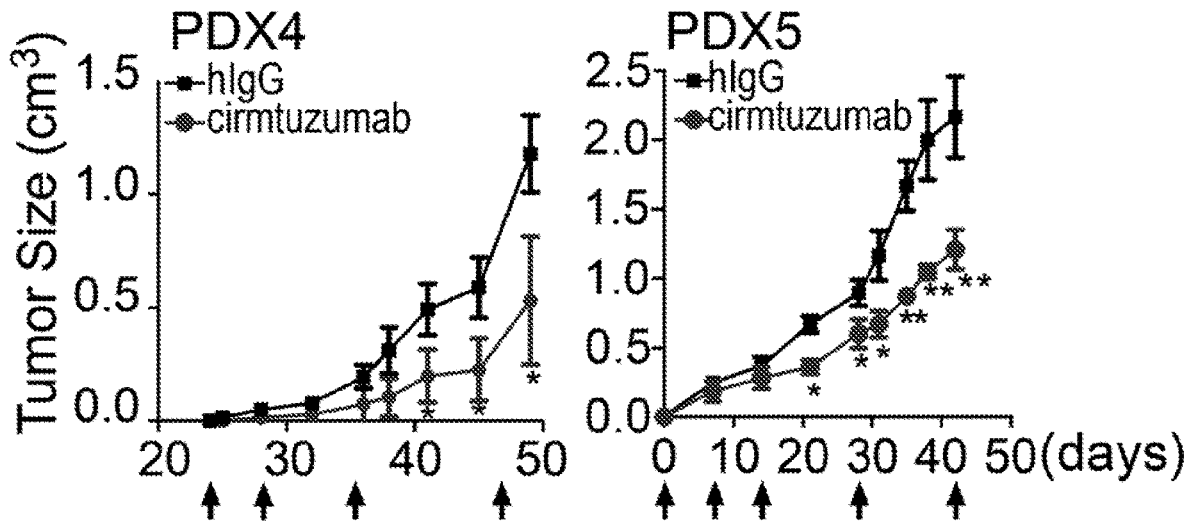
FIGS. 4A-4G. The figures show Cirmtuzumab Represses Activation Of Hippo-YAP and BMI1, And Inhibits Engraftment, Self-renewal, And Metastasis Of Breast Cancer PDX.
Figure 4B:
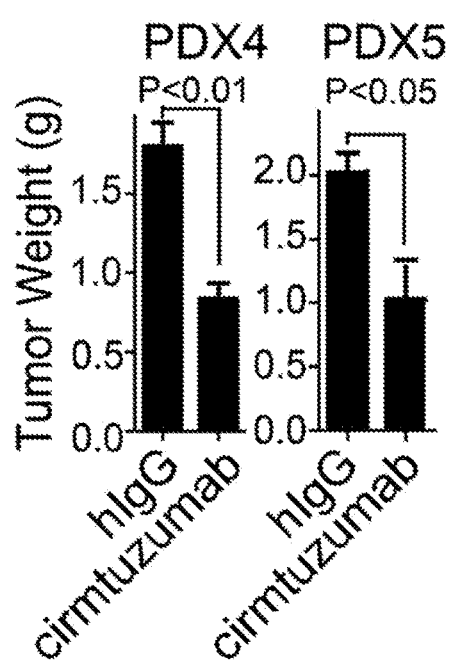
Figure 4C:
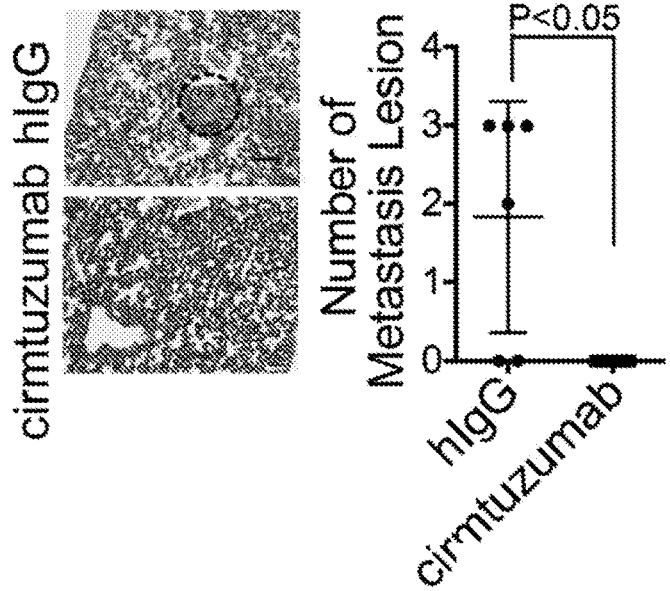
Figure 9C:
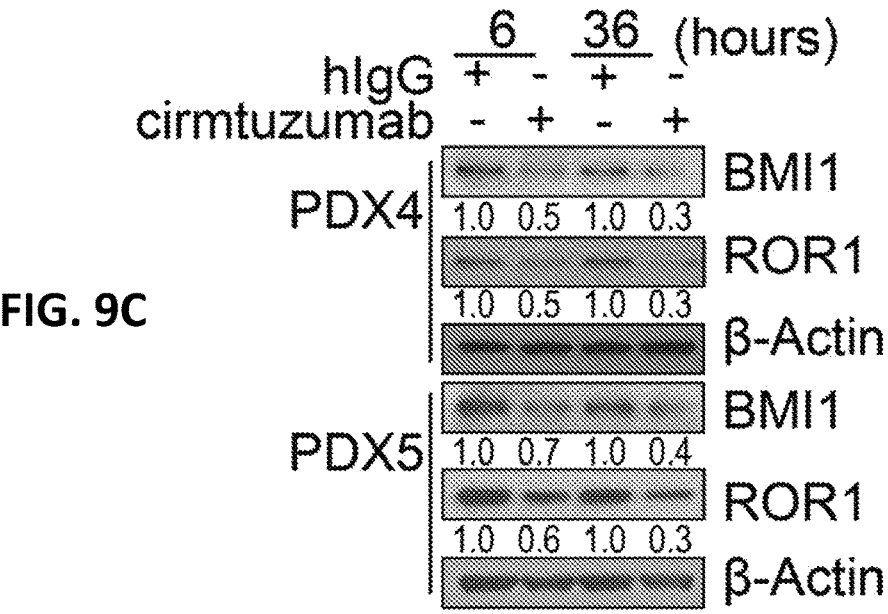
Figure 9D:
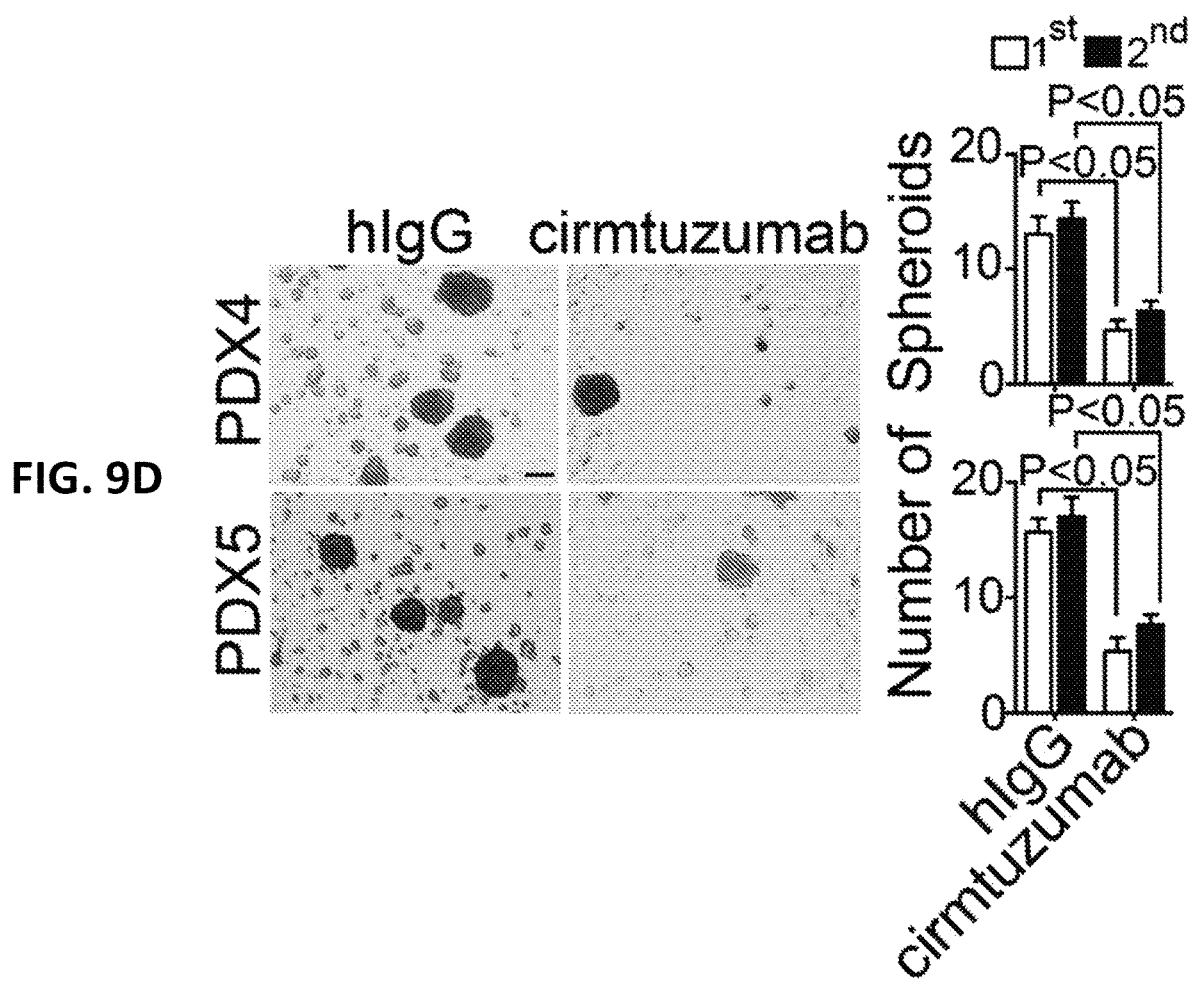
Figure 9E:
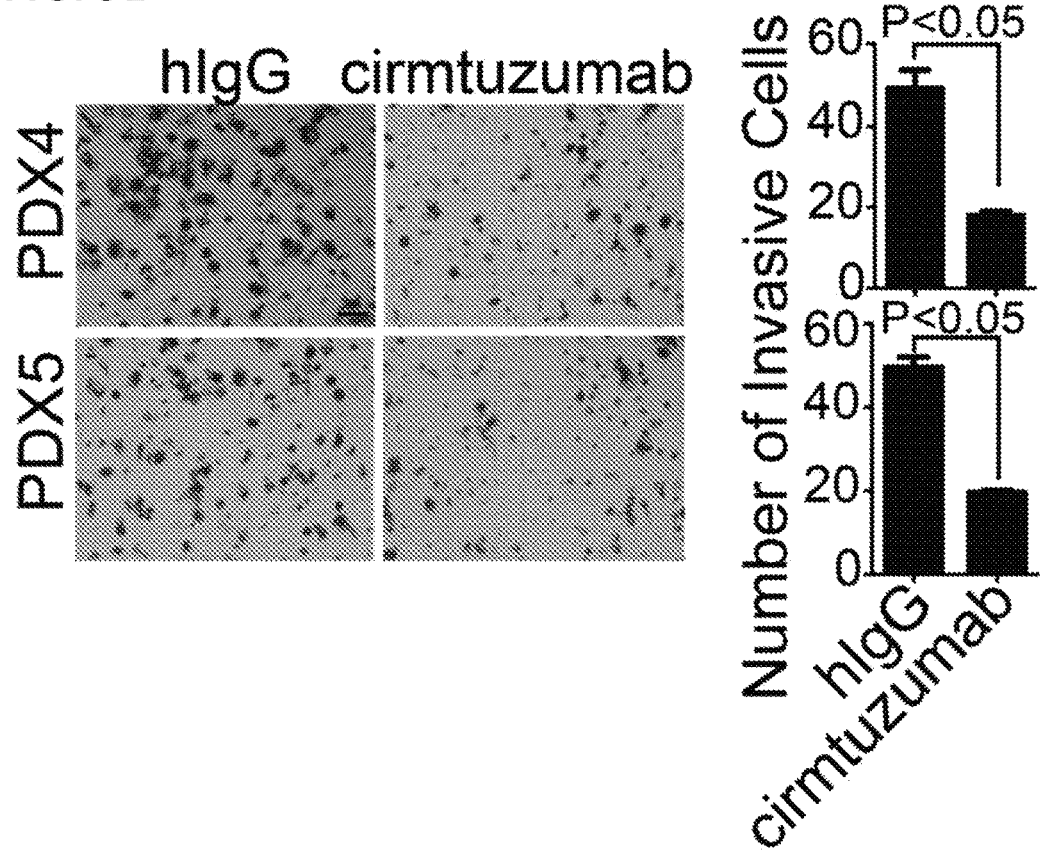
Figure 9F:
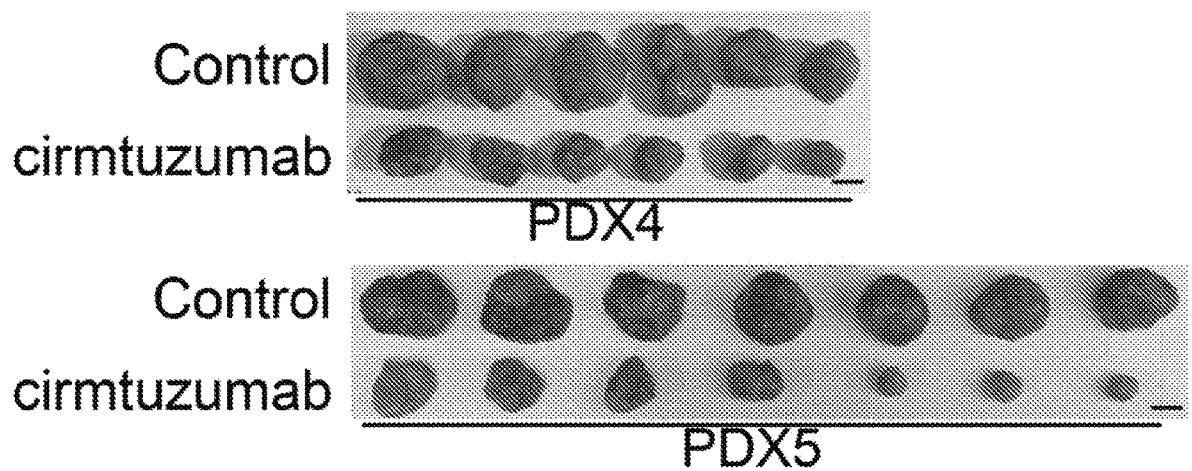

A time course study revealed that cirmtuzumab, but not a non-specific hIgG, could reduce expression of BMI1 within 6 hours (FIG. 9C). Cirmtuzumab also inhibited the capacity of breast cancer PDX to form spheroids or invade Matrigel (FIG. 9D-9E). Biweekly intravenous infusions of cirmtuzumab (at 10 mg/kg) significantly suppressed the development and growth of PDX tumors (FIG. 4A-4B and FIG. 9F). Moreover, the differences noted in the numbers of pulmonary metastases between cirmtuzumab-treated (N=0/mouse) versus control-treated (N=2/mouse) animals were statistically significant (P<0.05, Student's t-Test).

Figure 4D:
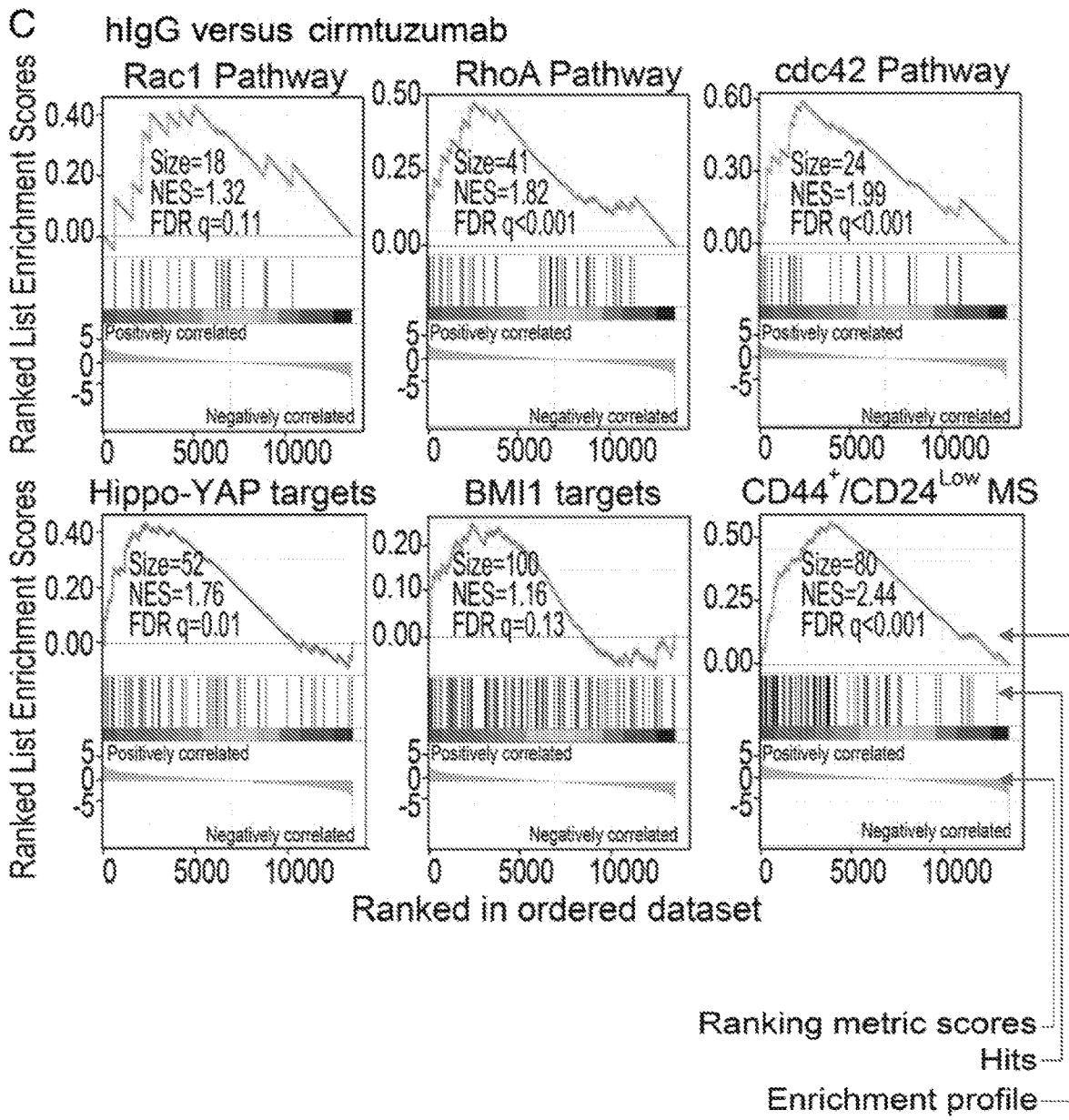
Figure 4E:
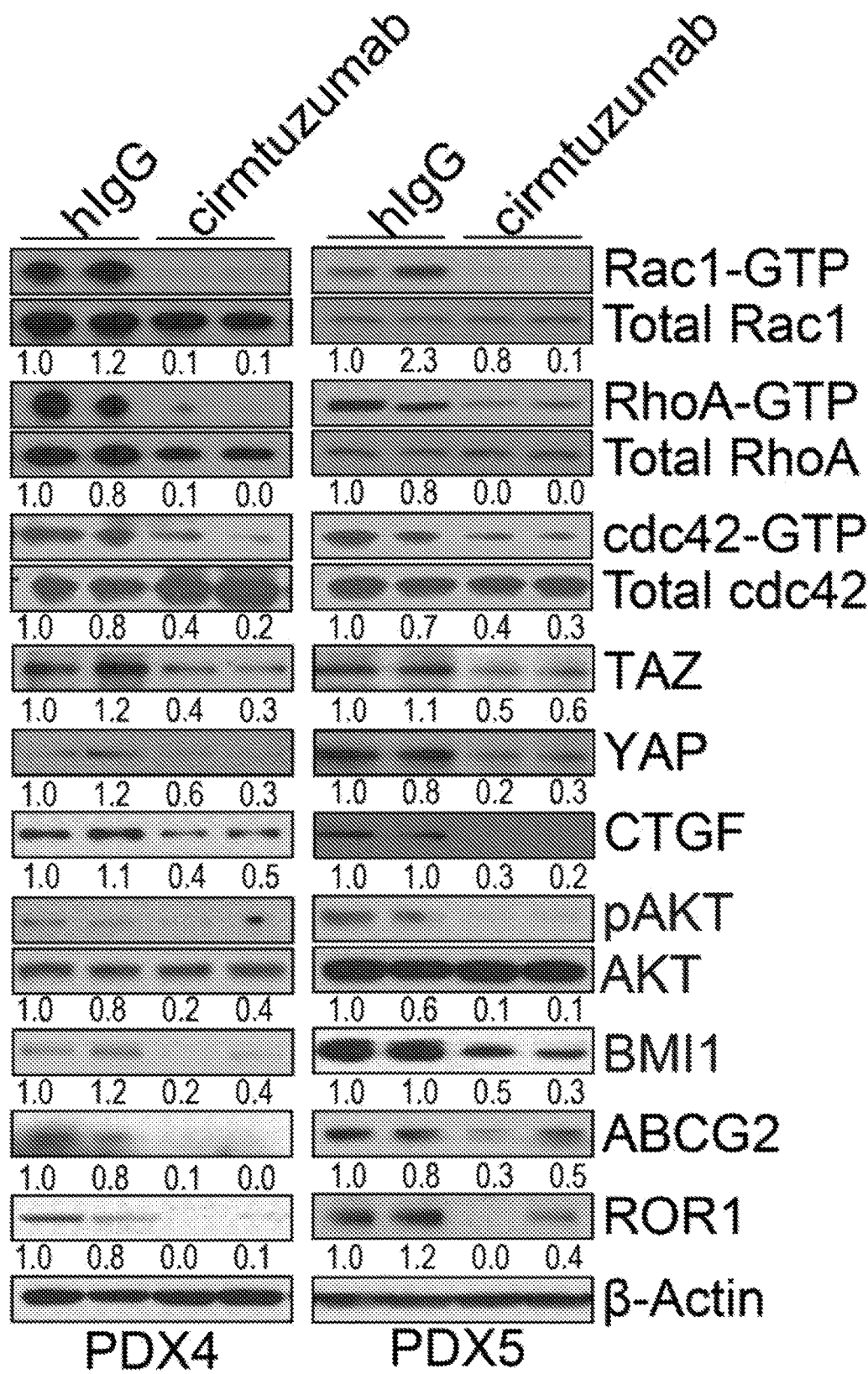

We examined the transcriptomes of tumors excised from cirmtuzumab-treated mice (N=4) versus those excised from control-Ig-treated mice (N=4) and performed GSE analysis on the RNA-SEQ data (GSE108632). Tumor cells isolated from PDX of cirmtuzumab-treated mice had significantly lower expression of genes associated with activation of Rho-GTPases, Hippo-YAP, or BMI1, or CD44+/CD24$^{Low}$ tumor cells, than tumor cells of PDX from control-treated mice (FIG. 4D). The PDX of cirmtuzumab-treated mice also had lower levels of ROR1 by immunoblot analyses, reduced levels genes associated with Rho-GTPase activation, and lower levels of genes targeted by Hippo-YAP (e.g. CTGF) or BMI1 (e.g. ABCG2) than PDX of control-treated mice (FIG. 4E). Tumors of cirmtuzumab-treated mice also had significantly lower proportions of cells bearing markers of CSCs (e.g. CD44+/CD24$^{Low}$ population), and lower expression of genes ordinarily expressed at high levels by CD44+/CD24$^{Low}$ tumor cells (FIG. 4F), than tumors of control hIgG-treated mice.

Figures 4F, 4G:
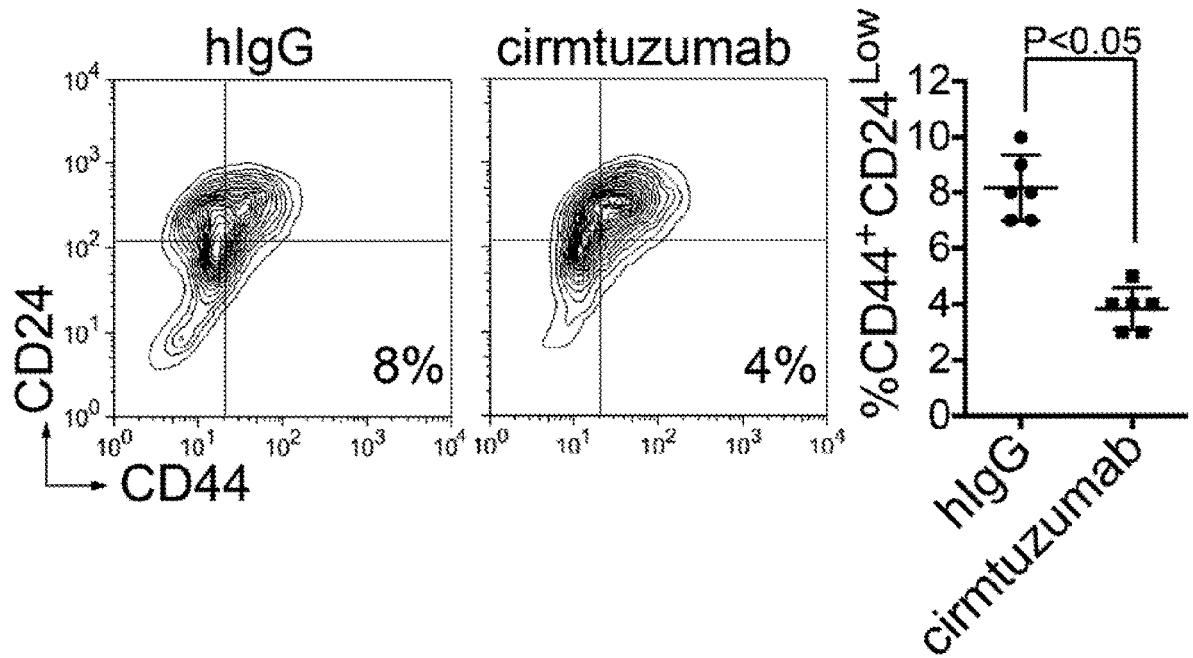

We isolated tumor cells of PDX from mice treated with cirmtuzumab or control-hIgG and examined their relative capacity to form secondary PDX in Rag2$^{−/−}$γc$^{−/−}$ mice. Tumor cells of PDX from cirmtuzumab-treated mice were significantly less effective in engrafting mice than tumor cells of the same PDX from control-treated animals (FIG. 4G). Collectively, these data indicate that treatment with cirmtuzumab can inhibit the growth and self-renewal of breast CSCs.

Paclitaxel and Cirmtuzumab Achieve Greater Tumor Clearance than Either Alone

Figure 10:
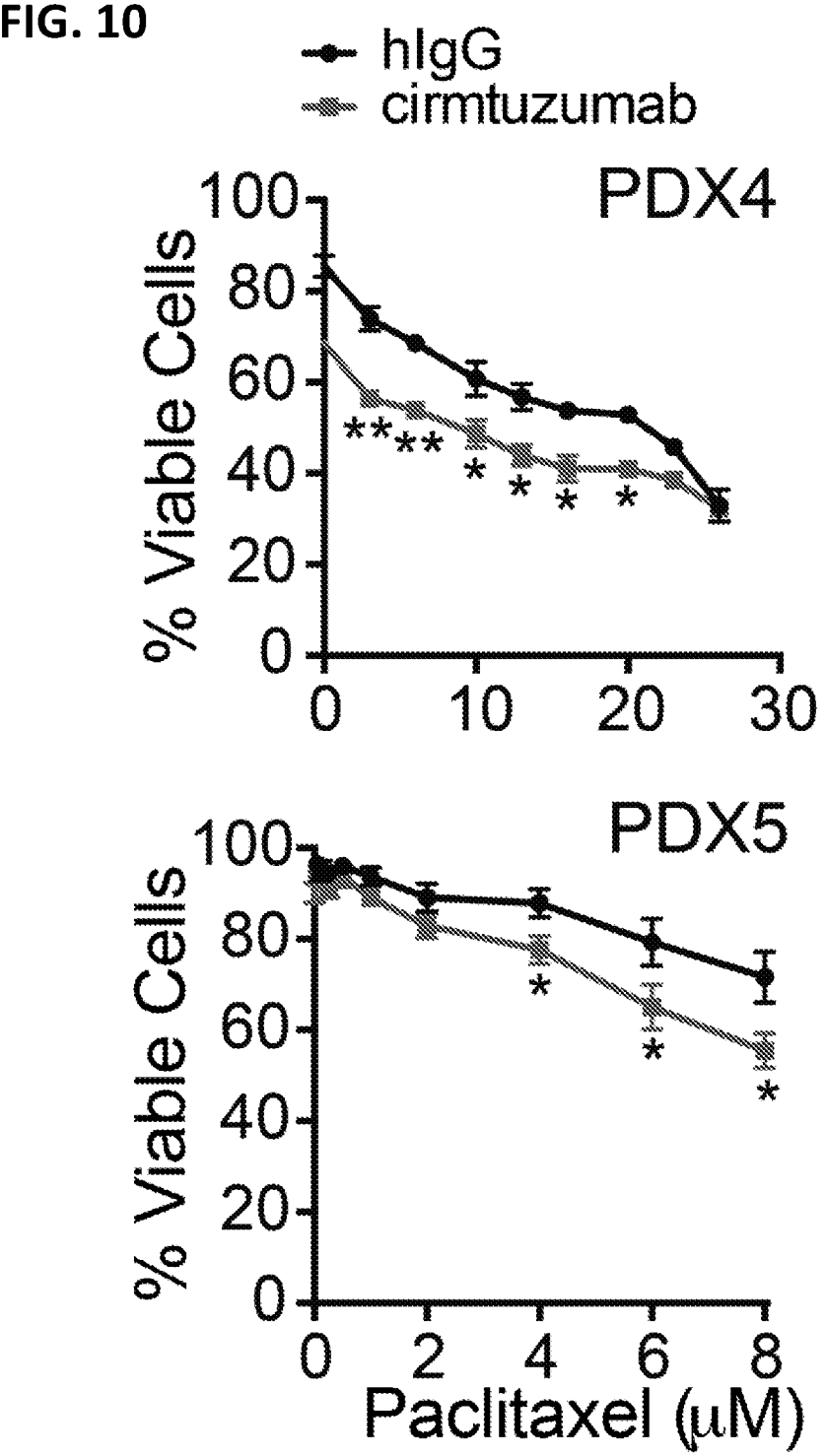
FIG. 10. This figure shows Treatments With Cirmtuzumab Enhanced The Sensitivity Of Breast Cancer Cells To Paclitaxel. Single cell suspension of PDX4 or PDX5 samples were treated with cirmtuzumab or control antibody with or without increasing concentration of paclitaxel for 24 hours. Data are shown as the mean (±SEM) percentage of viable cells of triplicated samples from each of the treatments as determined by flow cytometry analysis. An asterisk indicates P<0.05 and ** indicates P<0.01 as determined by Student's t-Test.
Figure 11:
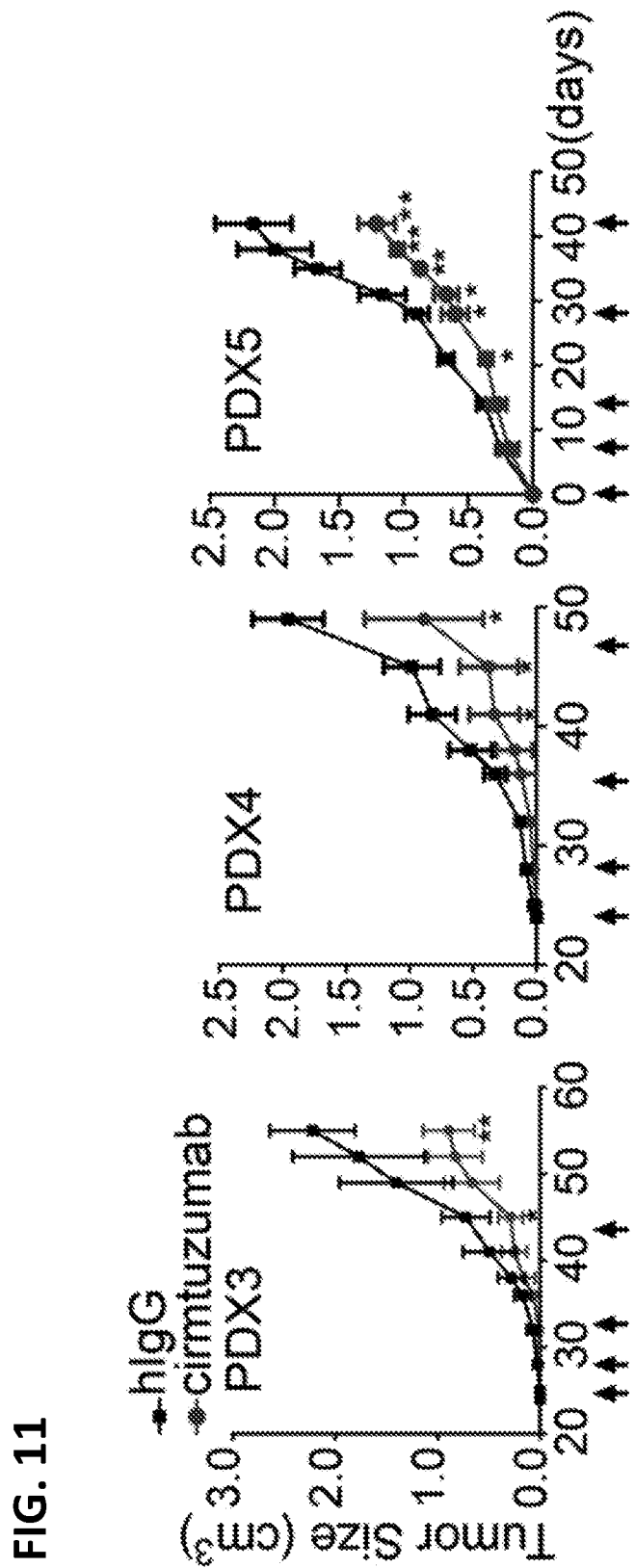
FIG. 11. This figure shows a line graph depicting the mean tumor growth of each of PDX3, PDX4, and PDX5 over time (±SEM, n=6-8) for animals that did not receive treatment (square data points) or that were treated with cirmtuzumab (round data points) on the days indicated by the arrows. One asterisk indicates P<0.05, and two asterisks indicate P<0.01 using Student's t Test.
Figure 18:
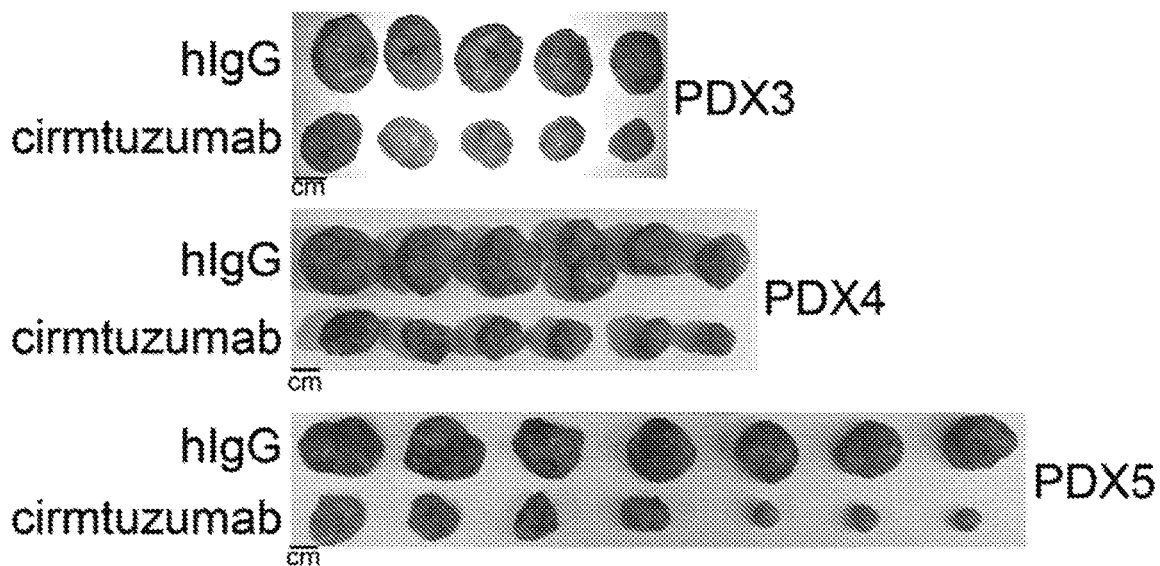
FIG. 18. 2 (PDX5) or 48 (PDX4) days, after 1×10$^6$ cells from each PDX sample in 50 μl were mixed with equal volumes of Matrigel and then injected into the mammary pad of female Rag2−/−γc−/− mice. Tumor growth was monitored over time for 42 or 48 days. Scale bar: 1 cm.
Figure 19:
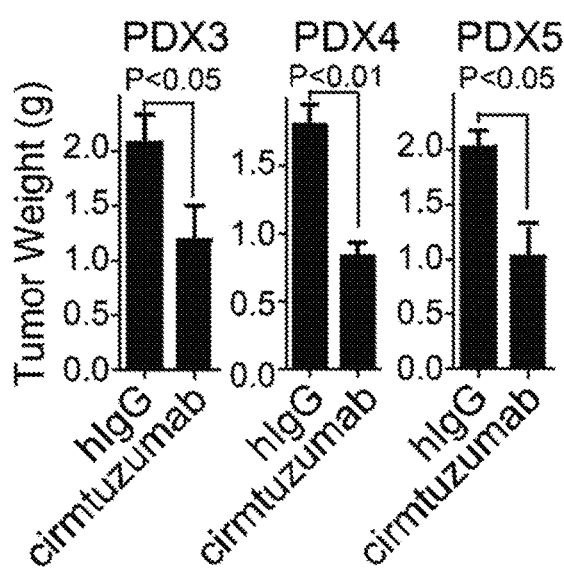
FIG. 19. This figure shows a bar graph providing average weight of tumors extirpated from the mice in each group described in FIG. 18. (±SEM, N=5-8).
Figure 20:
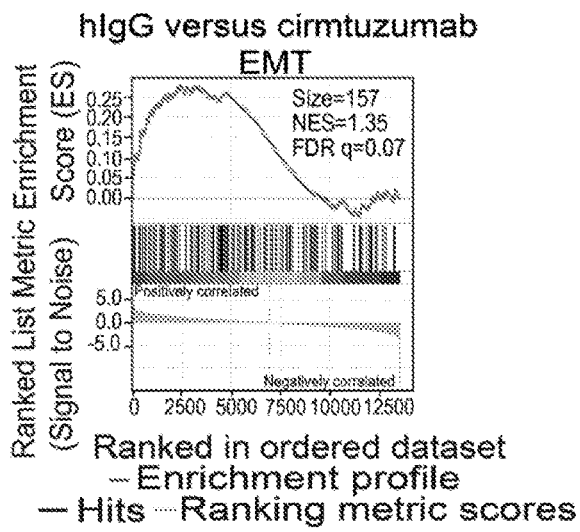
FIG. 20. This figure shows enrichment plots of genes associated with EMT in PDX derived from PDX4 in mice treated with control hIgG versus cirmtuzumab, as assessed via RNAseq (GSE108632).

We treated equivalent numbers of tumor cells from PDX4 or PDX5 with cirmtuzumab or control hIgG at 50 μg/ml overnight and then cultured the cells in separate wells in triplicate with increasing concentrations of paclitaxel. Treatment with cirmtuzumab significantly enhanced the sensitivity of the breast cancer cells to the cytotoxic effects of paclitaxel (e.g. IC50 of PDX4: 1±1 μm with cirmtuzumab versus 23±1 μm with non-specific hIgG, P<0.001, Student t-Test, FIG. 10).

Figure 5A:
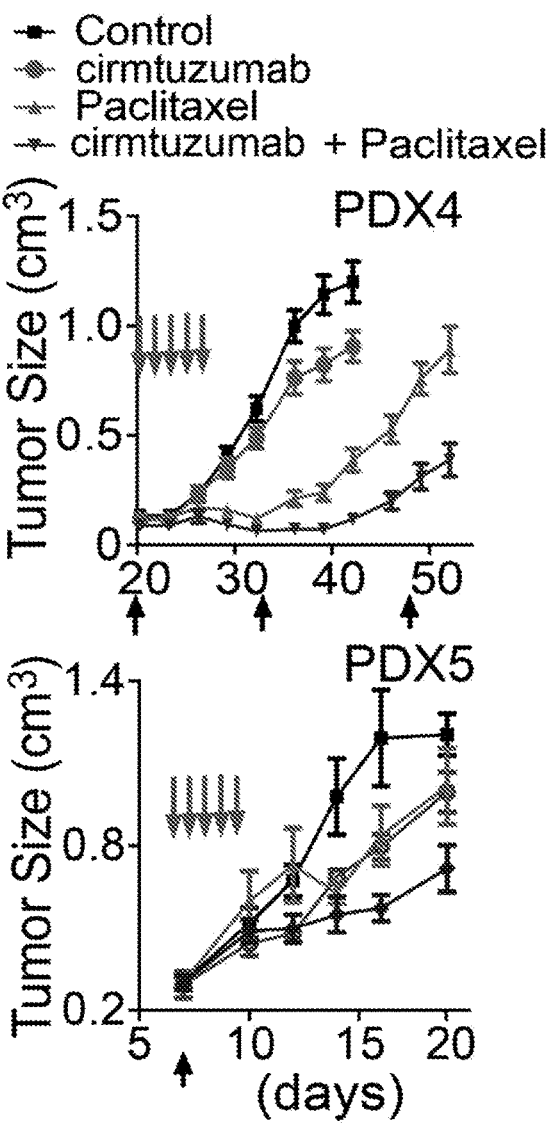
FIGS. 5A-5C. The figures show Cirmtuzumab And Paclitaxel Have Complementary Activities Against Breast-cancer PDX.
Figure 5B:
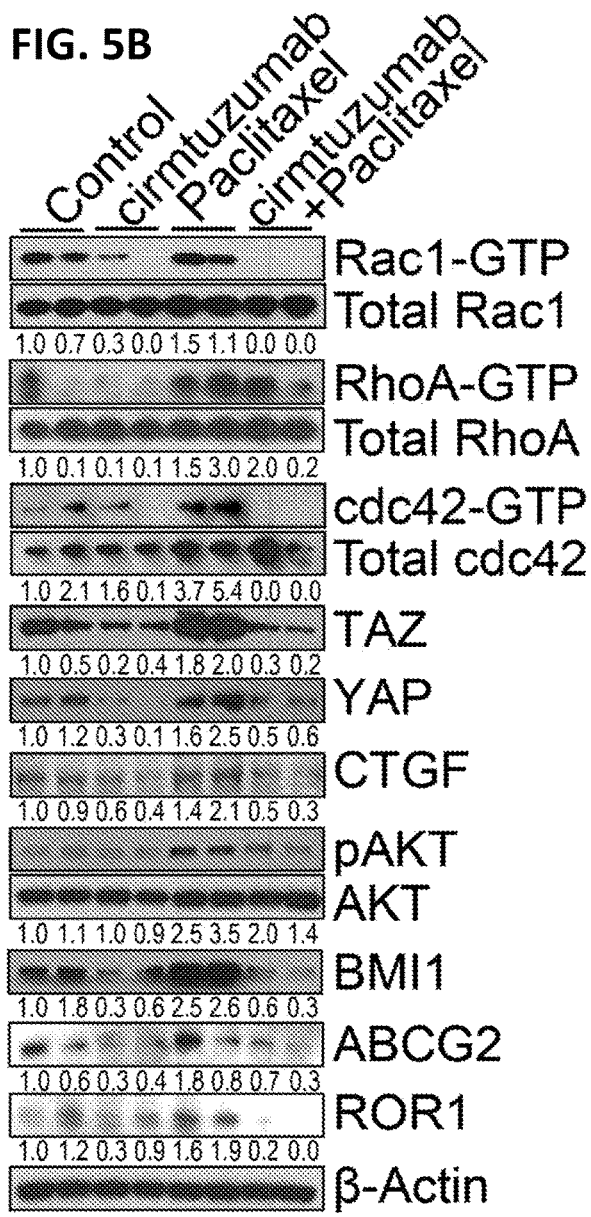

We treated PDX4- or PDX5-bearing mice with cirmtuzumab (10 mg/kg), paclitaxel (13.4 mg/kg), (Desai et al., 2006) or the combination of cirmtuzumab and paclitaxel. Treatment with cirmtuzumab and paclitaxel was significantly more effective in reducing tumor volumes than treatment with either cirmtuzumab or paclitaxel alone (FIG. 5A), each of which inhibited tumor growth relative to that of control-treated animals. The tumor cells isolated from PDX of mice treated with cirmtuzumab and paclitaxel had reduced levels of ROR1, reduced activation of Rho-GTPases and AKT, reduced levels of YAP/TAZ, and lower-level expression of Hippo-YAP target genes (e.g. CTGF), lower levels of BMI1, and lower expression-levels of BMI1-target genes (e.g. ABCG2), than did the tumor cells treated with paclitaxel alone (FIG. 5B). These data demonstrate that the combination of cirmtuzumab and paclitaxel had complementary anti-tumor activity.

Figure 5C:
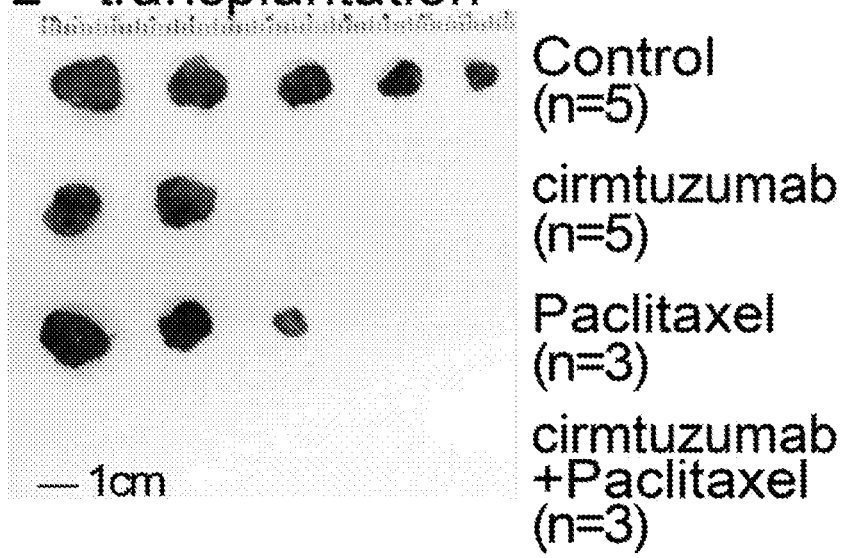

We isolated tumor cells of PDX that relapsed after therapy and examined their capacity to re-engraft immune-deficient mice. We found that the tumor cells of PDX from mice treated with single-agent paclitaxel readily developed secondary PDX. However, the tumor cells recovered from mice treated with cirmtuzumab were less effective in developing secondary PDX than even the tumor cells recovered from control-IgG-treated animals. On the other hand, none of the mice engrafted with tumor cells isolated from mice treated with cirmtuzumab and paclitaxel developed detectable tumors (FIG. 5C).

Tumor recurrence following treatment with chemotherapy may be driven by a subpopulation of CSCs, which are relatively resistant to standard chemotherapy and have self-renewing and/or tumor-initiating capacities. (Brooks et al., 2015; Wahl and Spike, 2017) Consistent with this notion, we observed that the residual breast cancer cells after conventional chemotherapy had higher expression of CSCs markers, and genes associated with CSCs (e.g. Hippo-YAP or BMI1 target genes) than matched tumor specimens obtained prior to chemotherapy. Prior studies noted that PDX isolated from paclitaxel-treated animals were enriched for cells that had features of breast CSC. (Bhola et al., 2013; Samanta et al., 2014) We found that breast cancers also were enriched for ROR1+ cells after chemotherapy, implying that ROR1 is a marker for CSC, which appear to be selected and/or induced with chemotherapy. (Wahl and Spike, 2017)

That ROR1 may serve as a marker for breast CSC cells also was indicated in the analyses of gene expression data of breast-cancer biopsies patients prior to therapy. We found that ROR1Hi breast cancers expressed higher levels of ALDH1A1 and other genes associated with CSCs than did ROR1$^{Low}$ breast cancers. Moreover, sorted ROR1+ cancer cells of the same tumor expressed higher levels of CSC-associated genes than ROR1$^{Neg}$ cells of the same tumor. Furthermore, ROR1+ tumor cells had a greater capacity to form spheroids, invade Matrigel, and engraft immunodeficient mice, than ROR1$^{Neg}$ tumor cells from the same tumor. Collectively, these studies indicate that ROR1 is a marker for breast CSCs.

ROR1 is not merely a marker for CSCs, but also apparently plays a functional role in the maintenance of CSCs. We found that expression of genes associated with activation of Rho-GTPases were increased in breast cancer cells that expressed ROR1 and that Wnt5a could enhance Rho-GTPase activation in a ROR1-dependent manner. Prior studies found that Rho GTPase-signaling is altered in human breast tumors, and elevated expression and activation of Rho-GTPases correlates with tumor progression, metastasis, and poor prognosis. (Fritz et al., 1999; McHenry and Vargo-Gogola, 2010) Furthermore, activation of Rac1 may promote the survival of breast cancer cells in response to hyper-fractionated radiation treatment. (Hein et al., 2016)

ROR1 also contributes to activation of the Hippo-YAP pathway. YAP/TAZ are important mediators of the Hippo-YAP pathway, which can promote stemness in embryonic or induced-pluripotent stem cells, as well as promote tumorigenesis by increasing cancer-cell migration and invasiveness, resistance to chemotherapy, and capacity to form distant metastases. (Bartucci et al., 2015; Chan et al., 2008; Hiemer et al., 2014; Mo et al., 2014; Moroishi et al., 2015; Tamm et al., 2011) Prior studies found that Rho-GTPase signaling may direct the Hippo-YAP pathway to sustain human embryonic stem cell survival and self-renewal. (Ohgushi et al., 2015) Moreover, co-expression of ROR1 with either FZD2 or FZD5 induced significant YAP dephosphorylation and TAZ accumulation, leading to activation of Hippo-YAP signaling in HEK293A cells. (Park et al., 2015) Similarly, we found that ROR1 was associated with expression and nuclear localization of TAZ in primary breast cancer cells and that Wnt5a could enhance nuclear accumulation of YAP/TAZ in a ROR1-dependent manner.

The level of BMI1 in primary breast cancer specimens also correlated with the level of ROR1. Wnt5a could induce ROR1-dependent increases in breast-cancer-cell-expression of BMI1 within 2 hours. The rapid induction of BMI1 suggests that Wnt5a/ROR1 signaling enhances the post-transcriptional stability of BMI1, which appears dependent upon activation of AKT. Activated AKT can phosphorylate BMI1 at 3 highly-conserved serine residues, leading to reduced BMI1 protein turnover. (Murga et al., 2002; Nacerddine et al., 2012; Voncken et al., 2005) Consistent with this notion, we found that silencing AKT inhibited the capacity of Wnt5a to induce BMI1 in ROR1+ breast cancer cells.

Because postpartum expression of ROR1 appears virtually restricted to cancer cells, (Zhang et al., 2012a) ROR1 is an attractive target for anti-cancer therapy. Cirmtuzumab is a humanized mAb specific for ROR1 that is undergoing clinical evaluation in patients with CLL. (Choi et al., 2015) Prior studies found that cirmtuzumab could inhibit proliferation and migration of ROR1+CLL cells in response to Wnt5a. (Yu et al., 2016) Here we demonstrate that cirmtuzumab also could inhibit activation of Rho-GTPases, repress expression of genes targeted by Hippo-YAP or BMI1, or genes up-regulated in CD44+/CD24$^{Low}$ breast CSCs, revealing that cirmtuzumab may inhibit the signaling required for the maintenance and migration of CSC. Consistent with this notion, we found that cirmtuzumab could suppress the capacity of ROR1+ breast tumor cells to engraft immune-deficient mice or form distant metastases. Furthermore, we found that cirmtuzumab could enhance the sensitivity of ROR1+ tumor cells to treatment with paclitaxel in vitro, possibly due to its capacity to inhibit activation of YAP/TAZ or BMI1 target genes, which prior studies demonstrated could contribute to drug-resistance. (Kreso et al., 2014; Wu et al., 2011)

Functional differences between CSC and non-CSC cells may influence response to therapy and the proclivity to relapse after therapy. (Wahl and Spike, 2017; Wang et al., 2015) This might account for why combined treatment with cirmtuzumab and paclitaxel in vivo had greater activity against established PDX than either therapy alone. Accordingly, combination therapy with one directed at CSCs (e.g. cirmtuzumab) and one directed at non-CSC (e.g. paclitaxel) may have synergistic therapeutic activity, potentially providing for improved treatment outcome and survival of patients with breast cancer.

Experimental Model and Subject Details

Breast cancer specimens. The fresh frozen breast tissues examined for expression of ROR1, TAZ, or BMI1 were obtained from the Peking University Shenzhen Hospital in China, upon approval of hospital authorities and patients, who provided signed informed consent. All protocols were approved by the Peking University Shenzhen Hospital of Shenzhen Medical Ethics Committee. Forty-four match formalin-fixed paraffin-embedded (FFPE) tumor tissues derived from 22 patients newly diagnosed with invasive ductal carcinoma at Sun Yat-set University Cancer Center, China, from September 2005 to January 2015. All the patients had a core needle biopsy or excisional biopsy before neoadjuvant chemotherapy. After chemotherapy, all the patients underwent surgical treatment. We examined matched formalin-fixed paraffin-embedded tissues from each patient before and after neoadjuvant chemotherapy. The pre-operative chemotherapy consisted of docetaxel, and/or doxorubicin, and/or cyclophosphamide. All protocols were approved by Medical Ethics Committee of Sun Yat-set University Cancer Center. Primary breast tumor specimens used to generate patient-derived xenografts were collected from patients, who provided written informed consent as per a protocol approved by the Institutional Review Board of UC San Diego (HRPP #090401), in accordance with the Declaration of Helsinki.

Patient-Derived xenografts. Four-to-eight-week-old female Rag2−/−γc−/− mice were used in this study following the care and use of laboratory animal guidelines of National Institutes of Health (NIH). The UC San Diego Medical Experimental Animal Care Committee approved the study protocol. The mice were housed in laminar-flow cabinets under specific pathogen-free conditions and fed ad libitum. The PDX were established using mechanically minced fresh breast cancer specimens. Early passage (P1-P5) of primary tumor tissues from these PDX models were mechanically minced, enzymatically and mechanically dissociated using GentleMACS Dissociator (Miltenyi Biotec), in accordance to the manufacturer's instruction. Erythrocytes were removed via density gradient centrifugation in Percoll™ Plus (GE Healthcare Life Sciences, CC-17-5442-01).

Tumorigenicity Assay. Cells were suspended in Mammary-Epithelial Growth Medium (MEGM), mixed with Matrigel (BD Biosciences, San Diego, CA) at a 1:1 ratio, and then transplanted into the mammary pads of Rag2−/−γc−/− mice. We monitored the mice weekly for the development of tumors. We extirpated the tumor to examine the tumor cells for expression of ROR1 at 10 days after treatment with 13.4 mg/kg paclitaxel via intravenously injection for consecutive 5 days. To examine for metastases, we harvested the lungs of 6 mice from each treatment group at 42 or 48 days post-transplantation and fixed the tissue with 10%-formalin, prior to embedding in paraffin. Each paraffin block was cut into 200-μm sections. Tumor foci were scored in a blinded fashion by a board-certified pathologist. To test whether cirmtuzumab alone or in combination with paclitaxel impaired engraftment of primary breast tumor cells, 1×105 single cells isolated from PDX4 or PDX5 were injected into the mammary pads of 4- to 6-week-old Rag2−/−γc−/− mice. When tumor size reached 300 mm3, 13.4 mg/kg paclitaxel was injected intravenously for consecutive 5 days or/and 10 mg/kg of cirmtuzumab was injected intravenously at day 0, day 7 and then biweekly.

Control groups were injected with hIgG instead of cirmtuzumab. The tumor volume (v) was determined using the formula v=(length)×(width)2×0.4.

RNA-Seq. sample preparation and sequencing. Total RNA was prepared from tumor tissues excised from mice that had been treated with either control hIgG or cirmtuzumab, using the Trizol RNA-extraction protocol, followed with purification using a RNeasy column (Qiagen kit). Total RNA was assessed for quality using an Agilent Tapestation. Samples had RNA Integrity Numbers (RIN) ranging from 9.2 to 9.9. RNA libraries were generated from 1 μg of RNA using Illumina's TruSeq Stranded mRNA Sample Prep Kit following the manufacturer's instructions, modifying the shear time to 5 minutes. RNA libraries were multiplexed and sequenced with 50 basepair (bp) single end reads (SR50) to a depth of approximately 40 million reads per sample on an Illumina HiSeq4000. We applied standard RNA-seq analytical pipeline to the eight samples. Briefly, adapters were removed and reads were trimmed of bases with low quality scores in late sequencing cycles using Cutadapt, which removes adapter sequences from high-throughput sequencing reads. (Marcel, 2011). We then mapped the reads to human genome build 38, using the STAR aligner (v2.5.2b). (Dobin et al., 2013) RSEM (v1.3.0) (Li and Dewey, 2011) was used to obtain the raw gene counts from the read alignments and Ensembl gene models (v83). (Yates et al., 2016) We used package DEseq2 (Love et al., 2014) to normalize the read count data and package limma (Ritchie et al., 2015) assess for differential expression. The data were deposited in a GEO database (GSE108632).

Gene set enrichment analyses. We used the GSEA software (Subramanian et al., 2005) to conduct gene-set-enrichment analyses (GSEA) on the primary microarray data available in the GEO database under accession numbers GSE87455 (Kimbung et al., 2018) and GSE21974. (Stickeler et al., 2011) We also performed GSEA of RNA-Seq data generated from PDX samples isolated from either cirmtuzumab-treated mice or control mice. Gene expression data obtained from 50 breast cancer samples obtained before (n=25) or after (n=25) chemotherapy treatment (Tx) GSE21974 or from 122 breast cancer samples from GSE87455 dataset were ranked by their relative expression of ROR1. Of these cases, tumors with a ROR1 expression value above the medium for all samples was designated as ROR1Hi, whereas tumors with ROR1 expression value below the medium value were designated as ROR1Low. We ranked genes by their association with the breast cancer groups (ROR1Hi versus ROR1Low) using a GSEA signal-to-noise ratio ranking metric. We focused GSEA on 3 pathways: Rac1 in BIOCARTA database, cdc42 in Pathway Interaction Database (Liberzon et al., 2011; Schaefer et al., 2009), and RhoA in Ingenuity Pathway database (IPA®, QIAGEN Redwood City, at website qiagen.com/ingenuity). Each gene set was considered significant when the alse discovery rate (FDR) was less than 25%. (Subramanian et al., 2005) For each gene set tested, we determined the gene-set size (SIZE), the enrichment score (ES), the normalized ES (NES), the nominal p value (NOM p-val), and the FDR q value (FDR q-val). The FDR q value was adjusted for gene set size and multiple hypothesis testing.

Spheroid formation assay. 300-10000 viable, single cells were plated on Ultra Low Attachment 6-well or 96-well plates (Corning Incorporated Life Sciences, Corning, NY) and cultured in MEGM™ mammary epithelial cell growth medium (Lonza, MD) with or without recombinant Wnt5a (R&D system) at 100 ng/ml for 1-3 weeks. Spheroids with sizes greater than 100 μm were counted using an inverted microscope (Nikon, Melville, NY).

Flow cytometry analysis. Single-cell suspensions were treated with Fc-blocking (Miltenyi Biotec), and then stained with Fluorescein-conjugated anti-CD44, phycoerythrin (PE)-conjugated anti-CD24, (Pharmingen), Alexa-647-conjugated 4A5, (Fukuda et al., 2008) PE-conjugated anti-EpCAM (BD Biosciences). ALDH1 activity was detected according to method described previously. (Zhang et al., 2014) Data were acquired using a FACS-Calibur or FACS-Aria (Becton Dickinson) and were analyzed using the FlowJo software (Tree Star). Forward light scatter (FSC) and side-light scatter (SSC) gating was used to exclude cell debris. Furthermore, we excluded cells that stained with propidium iodide (PI, Sigma) and gated on cells that stained with Calcein Violet (Life Technology) for viable cell analysis. Finally, gating on cells that bound to a mAb specific for human EpCAM allowed us to examine for breast cancer epithelial cells.

Cell-invasion assay. $5\times10^4$ viable single cells from primary tumors were suspended in MEBM growth medium (Lonza, MD), plated in invasion chambers (8-μm pore size, BD Biosciences), and cultured with or without cirmtuzumab (50 μg/ml) overnight. The lower chambers were filled with serum-free, conditioned medium collected from NIH3T3 cells. Invasion assay for cell lines were performed as described. (Cui et al., 2013) The cells on the apical side of each insert were scrapped off. Invasive cells were fixed with 4% paraformaldehyde and stained by Diff-Quick staining kits (IMEB Inc, San Marcos, CA) and visualized with an inverted microscope (Nikon).

Immunohistochemistry staining. For immunohistochemistry staining, primary tumors or lung organs excised from mouse xenografts were fixed in formalin. Lung tissue sections were prepared and stained with Hematoxylin & Eosin (H&E), Hematoxylin, and/or anti-ROR1 antibody (4A5), as described. (Zhang et al., 2012a) Images were collected using a Delta Vision microscope. The level of ROR1 was scored on the following scale: A score of 0 indicates that none of the cancer cells in the sample stained with the anti-ROR1 mAb; a score of 1 indicates low-level binding of the mAb to the tumor cells or low-to-moderate-level binding of the mAb to less than 50% of tumor cells; a score of 2 indicates moderate-level staining on more than 50% of tumor cells or high-level staining of the tumor cells on less than 50% of tumor cells; a score of 3 indicates high-level staining of the tumor cells on more than 50% of tumor cells. All staining was evaluated by board-certificated pathologist.

Immunofluorescence staining. Cells were cultured on coverslips to appropriate density or spun onto slides by use of a cytocentrifuge after various treatments. Cells were fixed with 4% paraformaldehyde and permeabilized with 0.1% Triton X-100 in PBS. After the cells were washed twice with PBS, they were blocked with 1% BSA in PBS for 30 minutes. Control antibodies or rabbit anti-YAP/TAZ and mouse 4A5 was added in blocking buffer and incubated for one and half hour. After washing the cells with PBS, they were incubated with Alexa Fluor 594-conjugated anti-rabbit secondary antibodies or Alexa Fluor 488-conjugated anti-mouse secondary antibodies for 1.5 h. The cells were then washed again and then mounted onto slides using ProLong Gold Antifade Reagent with DAPI (Life Technologies). The images were obtained and analyzed by using Olympus FV1000 confocal microscopy. The percentage of the nuclear localized YAP/TAZ was analyzed by Intensity measurement of Image J software. Nuclear localized YAP/TAZ is calculated by subtracting the YAP/TAZ signal intensity in the cytosol from the YAP/TAZ signal intensity of the total cell. The percentage of nuclear YAP/TAZ is calculated by dividing the nuclear-localized YAP/TAZ signal by YAP/TAZ signal for the entire cell.

BrdU Incorporation ELISA. 300-10,000 cells were plated in 96-well plate with or without different treatments and cultured for three days. BrdU cell proliferation ELISA (enzyme-linked immunosorbent assays, Roche) was performed according to manufacturer's instructions. Briefly, BrdU was added to the media and the cells were cultured overnight. Then cells were fixed, permeabilized in the wells of 96-well plates and incubated with peroxidase-conjugated antibodies specific for BrdU for two hours. Tetramethylbenzidine (TMB) substrate was used for peroxidase detection. The numbers of viable cells was calculated using a standard curve derived from different numbers of the same cells measured by the BrdU cell proliferation ELISA. The percent of viable cells was calculated by number of viable cells with different treatment groups normalized to number of viable cells without treatment.

Immunoblot analyses. Cells used for examination for proteins via immunoblot analysis were treated with control antibody or cirmtuzumab (50 μg/ml) for overnight and then were cultured in medium supplemented with or without recombinant Wnt5a (100 ng/ml). Treated cells or tissues were lysed in buffer containing 1% NP40, 0.1% SDS, 0.5% sodium deoxylate, supplemented with protease inhibitors (Pierce). Size-separated proteins were transferred to membranes, which were then incubated with primary antibodies specific for ROR1, YAP/TAZ, BMI-1, ABCG2, pAKT AKT, β-Actin (Cell Signaling Technology), Rac1, RhoA, cdc42 (Cytoskeleton), CTGF (Abcam), or Wnt5a (R&D system). After washing away unbound antibody, the membranes were incubated with secondary antibodies that were conjugated with horseradish peroxidase. Blots were then prepared for enhanced chemiluminescence and autoradiography. The protein concentration was determined using a bicinchoninic acid protein assay (Pierce).

Assays for activated RhoA, Rac1, and Cdc42. RhoA and Rac1 activation assay reagents were purchased from Cytoskeleton and used according to the manufacturer's instructions. Briefly, GTP-bound active RhoA, Rac1 or cdc42 was pulled down with Rhotekin-RBD or PAK-PBD beads, respectively, and then subjected to immunoblot analysis. Immunoblots of whole-cell lysates were used to assess for total RhoA, Rac1 or cdc42. The integrated optical density (IOD) of bands was evaluated by densitometry and analyzed using Gel-Pro Analyzer 4.0 software (Media Cybernetics).

Quantitative PCR. Total RNA was extracted using Trizol (Life Technologies). A 10-μg volume of total RNA was incubated with 10 U RNase-free DNase I (Life Technologies) at 37° C. for 30 minutes. RNA was further purified with an RNeasy Mini Kit (QIAGEN). The purified total RNA (2 μg) converted to cDNA using 200 U Superscript III Reverse Transcriptase (Life Technologies). Taq 2× Master Mix (NEB) was used for PCR according to the manufacturer's protocol.

CRISPR Knock out ROR1. SpCas9 and chimeric guide RNA expression plasmid PX330 (Addgene) were used to generate stable ROR1 knockout cell line according to the protocol described previously. (Zhang et al., 2012a) CRISPR targeting sequence (CCAGTGCGTGGCAACAAACGGCA) (SEQ ID NO:5) of ROR1 were designed with CRISPR Design tool (at website crispr.mit.edu). Cells transfected with ROR1 CRISPR plasmids were stained for ROR1 using 4A5-Alex647 and the ROR1-negative cells isolated and placed into culture. This process was repeated 3 successive times to isolate a population of ROR1 knock-out cells.

Silencing of human AKT. AKT siRNA was purchased from cell signaling. All siRNA transfections were performed in DMEM serum-free medium using lipofectaimine RNAiMAX (Invitrogen) according to the manufacturer's instruction, and then subjected to different assays.

Statistical analysis. Unless indicated otherwise, data were presented as the mean f standard error of the mean (SEM). Differences between two groups were determined by unpaired 2-tailed Student's t-Test. Differences between multiple groups were determined by Dunnett's multiple comparison test. All P values of less than 0.05 were considered significant. Analysis for significance was performed with GraphPad Prism 6.0 (GraphPad Software Inc.).

Tables

TABLE 1

Table 1 below shows Gene Set Enrichment (GSE) Analysis
Of 10 Stem-Cell Gene-Expression Signatures
On The ROR1$^{Hi}$ (N = 61) Versus ROR1$^{Low}$ (N = 61) Samples and
The ROR1$^{Low}$ (N = 61) Versus ROR1$^{Hi}$ (N = 61)
Samples From Breast Cancer Patients Prior To Chemotherapy or On
Breast Cancer Biopsies From Patients Who Received Neoadjuvant
Chemotherapy (N = 57) Versus Matched Pre-treatment Samples (N = 57)
in GSE87455 Database. An asterisk indicates that the gene set include ROR1.

| | | ES | | | NES | | | |
|---|---|---|---|---|---|---|---|---|
| Gene Sets | Size | ROR1$^{Hi}$ vs ROR1$^{Low}$ | ROR1$^{Low}$ vs ROR1$^{Hi}$ | Post vs Pre | ROR1$^{Hi}$ vs ROR1$^{Low}$ | ROR1$^{Low}$ vs ROR1$^{Hi}$ | Post vs Pre | Reference |
| CD44$^+$/CD24$^{Low}$ MS UP | 106 | 0.63 | −0.63 | 0.29 | 1.67 | −1.69 | 1.61 | (Creighton et al., 2009) |
| CD44$^+$/CD24$^{Low}$ MS Down | 233 | −0.59 | 0.59 | −0.36 | −1.56 | 1.54 | −1.73 | |
| Es exp 1 | 359 | 0.31 | −0.31 | −0.30 | 0.82 | −0.83 | −1.57 | (Ben-Porath et al., 2008) |
| Es exp 2 | 35 | −0.27 | 0.27 | −0.34 | −0.71 | 0.71 | −1.76 | |
| Nanog targets$^+$ | 913 | 0.31 | −0.31 | −0.21 | 1.01 | −1.01 | −1.57 | |
| Oct4 targets* | 274 | 0.37 | −0.37 | 0.16 | 1.19 | −1.19 | 1.23 | |
| Sox2 targets* | 678 | −0.33 | 0.33 | −0.23 | −1.05 | 1.05 | −1.62 | |
| NOS targets* | 168 | 0.43 | −0.43 | 0.18 | 1.34 | −1.33 | 1.27 | |
| NOS TFs | 37 | 0.55 | −0.55 | 0.19 | 1.40 | −1.42 | 1.01 | |
| Myc targets 1 | 227 | 0.34 | −0.34 | −0.22 | 1.03 | −1.03 | −1.46 | |
| Myc targets 2 | 755 | −0.42 | 0.42 | −0.29 | −1.28 | 1.28 | −1.91 | |

| | | NOM p-val | | | FDR q-val | | | |
|---|---|---|---|---|---|---|---|---|
| Gene Sets | Size | ROR1$^{Hi}$ vs ROR1$^{Low}$ | ROR1$^{Low}$ vs ROR1$^{Hi}$ | Post vs Pre | ROR1$^{Hi}$ vs ROR1$^{Low}$ | ROR1$^{Low}$ vs ROR1$^{Hi}$ | Post vs Pre | Reference |
| CD44$^+$/CD24$^{Low}$ MS UP | 106 | 0.00 | 0.00 | 0.04 | 0.01 | 0.01 | 0.07 | (Creighton et al., 2009) |
| CD44$^+$/CD24$^{Low}$ MS Down | 233 | 0.00 | 0.00 | 0.02 | 0.02 | 0.02 | 0.02 | |
| Es exp 1 | 359 | 0.72 | 0.73 | 0.06 | 0.85 | 0.85 | 0.03 | (Ben-Porath et al., 2008) |
| Es exp 2 | 35 | 0.87 | 0.88 | 0.04 | 0.97 | 0.97 | 0.03 | |
| Nanog targets$^+$ | 913 | 0.41 | 0.39 | 0.00 | 0.43 | 0.43 | 0.04 | |
| Oct4 targets* | 274 | 0.05 | 0.06 | 0.09 | 0.22 | 0.21 | 0.20 | |
| Sox2 targets* | 678 | 0.25 | 0.26 | 0.00 | 0.41 | 0.38 | 0.03 | |
| NOS targets* | 168 | 0.01 | 0.02 | 0.09 | 0.13 | 0.09 | 0.24 | |
| NOS TFs | 37 | 0.06 | 0.04 | 0.45 | 0.10 | 0.06 | 0.39 | |
| Myc targets 1 | 227 | 0.38 | 0.40 | 0.04 | 0.43 | 0.47 | 0.05 | |
| Myc targets 2 | 755 | 0.04 | 0.02 | 0.00 | 0.14 | 0.11 | 0.02 | |

TABLE 2

Table 2 below shows estrogen receptor and ROR1 expression status of tumors from breast cancer patients. ND indicates not defined.

| Patient ID | ER and HER2/NEU status | ROR1 status |
|---|---|---|
| 1 | N.D | − |
| 2 | HER2$^+$ | + |
| 3 | ER$^+$ | + |
| 4 | ER$^+$ | + |
| 5 | ER$^+$ | + |
| 6 | ER$^+$ | − |
| 7 | ER$^-$/PR$^-$/HER2$^-$ | + |
| 8 | N.D | − |
| 9 | ER$^+$ | + |
| 10 | ER$^+$ | − |
| 11 | ER$^+$ | − |
| 12 | ER$^+$ | + |
| 13 | HER2$^+$ | + |
| 14 | ER$^+$ | + |
| 15 | HER2$^+$ | + |
| 16 | ER$^+$ | + |
| 17 | ER$^+$ | + |
| 18 | ER$^+$ | − |
| 19 | ER$^+$ | − |
| 20 | ER$^+$ | − |
| 21 | ER$^-$/PR$^-$HER2$^-$ | + |
| 22 | ER$^+$ | + |
| 23 | ND | + |

TABLE 3

Table 3 below shows clinical and pathologic characteristics of tumors from patients who received neoadjuvant therapy. CR indicates complete remission, PR indicates partial remission, and ND indicates not defined.

| Patient Number | ER/PR/HER2 Status | Treatment | Response | ROR1 Pre | Staining Post |
|---|---|---|---|---|---|
| 1 | ER−/PR−/HER2+ | Docetaxel/Epirubicin | PR | 1 | 2 |
| 2 | ER−/PR−/HER2− | Docetaxel/Epirubicin | PR | 2 | 3 |
| 3 | ER−/PR−/HER2+ | Docetaxel/Epirubicin/Cyclophosphamide | PR | 3 | 3 |
| 4 | ER−/PR−/HER2+ | Docetaxel/Epirubicin | PR | 1 | 3 |
| 5 | N.D | Docetaxel/Epirubicin/Cyclophosphamide | CR | 2 | 2 |
| 6 | N.D | Docetaxel/Epirubicin/Cyclophosphamide | PR | 2 | 2 |
| 7 | ER+/PR−/HER2− | Docetaxel/Epirubicin/Cyclophosphamide | PR | 2 | 2 |
| 8 | ER−/PR−/HER2− | Docetaxel/Epirubicin/Cyclophosphamide | CR | 2 | 3 |
| 9 | ER+/PR+/HER2− | Docetaxel/Epirubicin | PR | 1 | 3 |
| 10 | ER−/PR−/HER2− | Docetaxel/Epirubicin/Cyclophosphamide | PR | 2 | 3 |
| 11 | ER+/PR−/HER2− | Docetaxel/Epirubicin | PR | 1 | 2 |
| 12 | ER+/PR+/HER2− | Epirubicin/Cyclophosphamide | PR | 2 | 2 |
| 13 | ER+/PR−/HER2− | Docetaxel/Epirubicin | PR | 2 | 3 |
| 14 | ER+/PR−/HER2+ | Docetaxel/Epirubicin/Cyclophosphamide | CR | 3 | 3 |
| 15 | ER+/PR+/HER2− | Docetaxel/Epirubicin | PR | 2 | 3 |
| 16 | ER+/PR+/HER2− | Docetaxel/Dpirubicin/Cyclophosphamide | PR | 1 | 3 |
| 17 | N.D | Docetaxel/Doxorubicin/Cyclophosphamide | PR | 1 | 0 |
| 18 | ER−/PR+/HER2− | Docetaxel/Epirubicin | PR | 2 | 3 |
| 19 | N.D | Docetaxel/Epirubicin/Cyclophosphamide | PR | 2 | 3 |
| 20 | ER+/PR+/HER2− | Docetaxel/Epirubicin/Cyclophosphamide | PR | 2 | 2 |
| 21 | ER−/PR−/HER2+ | Docetaxel/Epirubicin | PR | 1 | 2 |
| 22 | ER+/PR+/HER2− | Docetaxel/Epirubicin/Cyclophosphamide | PR | 2 | 3 |

TABLE 4

Table 4 below shows clinical, pathologic characteristics and proportion of CSCs markers expression of tumors used to generate each PDX.

| PDX ID | ER/PR/HER2 status | Histology | P53 mutation status | Prior treatment | Expression of CSCs Markers | | |
|---|---|---|---|---|---|---|---|
| | | | | | ALDH1+ | CD44+ | CD44+/CD24$^{Low}$ |
| PDX1 | ER−/PR−/HER2+ | Ductal Carcinoma Primary Tumor | N/A | Taxane/Platinum/Trastuzumab | 0.6% | 1.8% | 0.1% |
| PDX2 | ER−/PR−/HER2− | Ductal Carcinoma Primary Tumor | no mutations | None | 2.9% | 63.1% | 48.8% |
| PDX3 | ER−/PR−/HER2− | Mixed Ductal and Lobular Carcinoma Primary Tumor | P53 mutation | Anthracycline/Taxane | 3.5% | 76.1% | 5.6% |
| PDX4 | ER−/PR−/HER2− | Ductal Carcinoma Primary Tumor | P53 mutation | Taxane | 6.5% | 23.9% | 2.3% |
| PDX5 | ER+/PR−/HER2− | Ductal Carcinoma Axillary Lymph Node | P53 mutation | N/A | 8.4% | 85.0% | 6.2% |

TABLE 5

Table 5 below shows tumor incidence in animals implanted with different subpopulations of cells isolated from breast cancer PDX.

| Subpopulation | Cell Number 500 | Cell Number 100 | Frequency of Tumorigenic Cell | P Value |
|---|---|---|---|---|
| CD44$^+$/CD24$^{Low}$ | 3/4 | 2/4 | 1/265 | 0.002 |
| CD44$^+$/CD24$^+$ | 0/4 | 0/4 | 1/Inf | |
| ALDH1$^+$ | 2/5 | 1/5 | 1/800 | 0.04 |
| ALDH1$^{Neg}$ | 0/4 | 0/4 | 1/Inf | |

TABLE 6

| Tissue ID | Treatment | Cell Number 10$^4$ | Cell Number 10$^3$ | Frequency of Tumorigenic Cell | P Value |
|---|---|---|---|---|---|
| PDX4 | Untreated | 3/5 | 0/5 | 1/12683 | 0.0002 |
|  | Paclitaxel | 5/5 | 4/5 | 1/622 | |
| PDX5 | Untreated | 4/5 | 0/5 | 1/7697 | 0.002 |
|  | Paclitaxel | 5/5 | 4/5 | 1/622 | |

TABLE 7

| Treatment | | Cell Number 1 × 10$^5$ | 1 × 10$^4$ | 1 × 10$^3$ | Frequency of Tumorigenic Cell | P Value |
|---|---|---|---|---|---|---|
| PDX4 | hIgG | 10/10 | 10/10 | 0/5 | 1/3285 | 8.61e-13 |
|  | cirmtuzumab | 2/10 | 1/10 | 0/5 | 1/247052 | |
| PDX5 | hIgG | N.D | 5/5 | 2/4 | 1/1420 | 0.001 |
|  | cirmtuzumab | N.D | 1/5 | 1/3 | 1/23572 | |

TABLE 8

| Treatment | PDX4 1 × 10$^5$ | PDX4 1 × 10$^4$ | PDX5 1 × 10$^5$ | PDX5 1 × 10$^4$ |
|---|---|---|---|---|
| Control | 5/5 | 5/5 | 5/5 | 5/5 |
| cirmtuzumab | 2/5 | 1/5 | 3/5 | 2/5 |
| Paclitaxel | 5/5 | 5/5 | 4/5 | 3/3 |
| cirmtuzumab + Paclitaxel | 0/5 | 0/4 | 0/5 | 0/3 |

TABLE 9

| Tissue ID | | Cell Number 5000 | 500 | 100 | Frequency of Tumorigenic Cell | P Value |
|---|---|---|---|---|---|---|
| PDX4 | ROR1$^+$ | 6/6 | 4/6 | N.D | 1/455 | <0.001 |
|  | ROR1$^{Neg}$ | 3/6 | 2/6 | N.D | 1/4740 | |
| PDX5 | ROR1$^+$ | N.D | 8/9 | 1/10 | 1/329 | <0.001 |
|  | ROR1$^{Neg}$ | N.D | 1/9 | 0/10 | 1/5247 | |

TABLE 10

Table 10 below shows tumor incidence in animals implanted with ROR1Hi or ROR1Low cells isolated from each of the various breast cancer PDX. Frequency of tumorigenic cells and probability estimates were computed using ELDA software. N.D indicates not done.

| Tissue ID | | Cell Number 5000 | 500 | 100 | Frequency of Tumorigenic Cell | PValue |
|---|---|---|---|---|---|---|
| PDX3 | ROR1$^{Low}$ | 0/4 | 0/9 | 0/10 | 1/2913 | <0.01 |
|  | ROR1$^{Hi}$ | 2/5 | 5/10 | 1/10 | Inf | |
| PDX4 | ROR1$^{Low}$ | 3/6 | 2/6 | N.D | 1/455 | <0.001 |
|  | ROR1$^{Hi}$ | 6/6 | 4/6 | N.D | 1/4740 | |
| PDX5 | ROR1$^{Low}$ | N.D | 1/9 | 0/10 | 1/329 | <0.001 |
|  | ROR1$^{Hi}$ | N.D | 8/9 | 1/10 | 1/5247 | |

TABLE 11

Table 11 below shows Gene Set Enrichment (GSE) Analysis for genes associated with CD44+/CD24Low MS, ETM, activation of Rac1/RhoA/cdc42, Hippo-YAP, BMI1 for the ROR1Low and ROR1Hi sample groups (N = 25) or on breast cancer biopsies from patients who received neoadjuvant chemotherapy (N = 25) Versus Matched Pre-treatment Samples (N = 25) in the GSE21974 database. SIZE is the number of genes included in the analysis. NES (normalized enrichment score) accounts for the difference in gene-set size and can be used to compare the analysis results across gene sets. NOM p-val (nominal p value) is the statistical significance of the enrichment score not adjusted for gene set size or multiple gene sets testing, FDR q-val (false discovery rate q value) is the estimated probability that a gene set with a given NES represents a false positive. Each gene set is considered significant when the false discovery rate (FDR) is less than 0.25.

| Gene Sets | Size | ES $ROR1^{Hi}$ vs $ROR1^{Low}$ | ES Post vs Pre | NES $ROR1^{Hi}$ vs $ROR1^{Low}$ | NES Post vs Pre | NOM p-val $ROR1^{Hi}$ vs $ROR1^{Low}$ | NOM p-val Post vs Pre | FDR q-val $ROR1^{Hi}$ vs $ROR1^{Low}$ | FDR q-val Post vs Pre |
|---|---|---|---|---|---|---|---|---|---|
| $CD44^+/CD24^{Low}$ MS | 99 | 0.46 | 0.52 | 1.61 | 2.16 | 0.03 | 0.00 | 0.07 | 0.00 |
| EMT | 220 | 0.52 | 0.31 | 1.78 | 1.47 | 0.00 | 0.00 | 0.00 | 0.03 |
| Rac1 Pathway | 22 | 0.48 | 0.52 | 1.44 | 1.61 | 0.05 | 0.01 | 0.08 | 0.01 |
| RhoA Pathway | 45 | 0.44 | 0.41 | 1.34 | 1.52 | 0.12 | 0.03 | 0.12 | 0.02 |
| cdc42 | 30 | 0.46 | 0.35 | 1.47 | 1.19 | 0.05 | 0.22 | 0.12 | 0.16 |
| Hippo-Yap | 57 | 0.53 | 0.36 | 1.60 | 1.33 | 0.04 | 0.07 | 0.03 | 0.07 |
| BMI1 | 143 | 0.32 | 0.42 | 1.17 | 1.90 | 0.20 | 0.00 | 0.20 | 0.00 |

REFERENCES

Al-Hajj, M., Wicha, M. S., Benito-Hernandez, A., Morrison, S. J., and Clarke, M. F. (2003). Prospective identification of tumorigenic breast cancer cells. Proc Natl Acad Sci USA 100, 3983-3988.

Bartucci, M., Dattilo, R., Moriconi, C., Pagliuca, A., Mottolese, M., Federici, G., Benedetto, A. D., Todaro, M., Stassi, G., Sperati, F., et al. (2015). TAZ is required for metastatic activity and chemoresistance of breast cancer stem cells. Oncogene 34, 681-690.

Ben-Porath, I., Thomson, M. W., Carey, V. J., Ge, R., Bell, G. W., Regev, A., and Weinberg, R. A. (2008). An embryonic stem cell-like gene expression signature in poorly differentiated aggressive human tumors. Nature genetics 40, 499-507.

Bhola, N. E., Balko, J. M., Dugger, T. C., Kuba, M. G., Sanchez, V., Sanders, M., Stanford, J., Cook, R. S., and Arteaga, C. L. (2013). TGF-beta inhibition enhances chemotherapy action against triple-negative breast cancer. J Clin Invest 123, 1348-1358.

Brooks, M. D., Burness, M. L., and Wicha, M. S. (2015). Therapeutic Implications of Cellular Heterogeneity and Plasticity in Breast Cancer. Cell Stem Cell 17, 260-271.

Chan, S. W., Lim, C. J., Guo, K., Ng, C. P., Lee, I., Hunziker, W., Zeng, Q., and Hong, W. (2008). A role for TAZ in migration, invasion, and tumorigenesis of breast cancer cells. Cancer research 68, 2592-2598.

Chien, H. P., Ueng, S. H., Chen, S. C., Chang, Y. S., Lin, Y. C., Lo, Y. F., Chang, H. K., Chuang, W. Y., Huang, Y. T., Cheung, Y. C., et al. (2016). Expression of ROR1 has prognostic significance in triple negative breast cancer. Virchows Archiv: an international journal of pathology 468, 589-595.

Choi, M. Y., Widhopf, G. F., 2nd, Wu, C. C., Cui, B., Lao, F., Sadarangani, A., Cavagnaro, J., Prussak, C., Carson, D. A., Jamieson, C., et al. (2015). Pre-clinical Specificity and Safety of UC-961, a First-In-Class Monoclonal Antibody Targeting ROR1. Clinical lymphoma, myeloma & leukemia 15 Suppl, S167-169.

Cordenonsi, M., Zanconato, F., Azzolin, L., Forcato, M., Rosato, A., Frasson, C., Inui, M., Montagner, M., Parenti, A. R., Poletti, A., et al. (2011). The Hippo transducer TAZ confers cancer stem cell-related traits on breast cancer cells. Cell 147, 759-772.

Creighton, C. J., Li, X., Landis, M., Dixon, J. M., Neumeister, V. M., S]olund, A., Rimm, D. L., Wong, H., Rodriguez, A., Herschkowitz, J. I., et al. (2009). Residual breast cancers after conventional therapy display mesenchymal as well as tumor-initiating features. Proc Natl Acad Sci USA 106, 13820-13825.

Cui, B., Zhang, S., Chen, L., Yu, J., Widhopf, G. F., 2nd, Fecteau, J. F., Rassenti, L. Z., and Kipps, T. J. (2013). Targeting ROR1 inhibits epithelial-mesenchymal transition and metastasis. Cancer Res 73, 3649-3660.

Desai, N., Trieu, V., Yao, Z., Louie, L., Ci, S., Yang, A., Tao, C., De, T., Beals, B., Dykes, D., et al. (2006). Increased antitumor activity, intratumor paclitaxel concentrations, and endothelial cell transport of cremophor-free, albumin-bound paclitaxel, ABI-007, compared with cremophor-based paclitaxel. Clinical cancer research: an official journal of the American Association for Cancer Research 12, 1317-1324.

Dobin, A., Davis, C. A., Schlesinger, F., Drenkow, J., Zaleski, C., Jha, S., Batut, P., Chaisson, M., and Gingeras, T. R. (2013). STAR: ultrafast universal RNA-seq aligner. Bioinformatics 29, 15-21.

Early Breast Cancer Trialists' Collaborative, G., Peto, R., Davies, C., Godwin, J., Gray, R., Pan, H. C., Clarke, M., Cutter, D., Darby, S., McGale, P., et a!. (2012). Comparisons between different polychemotherapy regimens for early breast cancer: meta-analyses of long-term outcome among 100,000 women in 123 randomised trials. Lancet 379, 432-444.

Fritz, G., Just, I., and Kaina, B. (1999). Rho GTPases are over-expressed in human tumors. International journal of cancer 81, 682-687.

Fukuda, T., Chen, L., Endo, T., Tang, L., Lu, D., Castro, J. E., Widhopf, G. F., 2nd, Rassenti, L. Z., Cantwell, M. J., Prussak, C. E., et a!. (2008). Antisera induced by infusions of autologous Ad-CD154-leukemia B cells identify ROR1 as an oncofetal antigen and receptor for Wnt5a. Proc Natl Acad Sci USA 105, 3047-3052.

Ginestier, C., Hur, M. H., Charafe-Jauffret, E., Monville, F., Dutcher, J., Brown, M., Jacquemier, J., Viens, P., Kleer, C.

G., Liu, S., et a!. (2007). ALDH1 is a marker of normal and malignant human mammary stem cells and a predictor of poor clinical outcome. Cell Stem Cell 1, 555-567.

Hein, A. L., Post, C. M., Sheinin, Y. M., Lakshmanan, I., Natarajan, A., Enke, C. A., Batra, S. K., Ouellette, M. M., and Yan, Y. (2016). RAC1 GTPase promotes the survival of breast cancer cells in response to hyper-fractionated radiation treatment. Oncogene 35, 6319-6329.

Hiemer, S. E., Szymaniak, A. D., and Varelas, X. (2014). The transcriptional regulators TAZ and YAP direct transforming growth factor beta-induced tumorigenic phenotypes in breast cancer cells. J Biol Chem 289, 13461-13474.

Kaur, S., Elkahloun, A. G., Singh, S. P., Chen, Q. R., Meerzaman, D. M., Song, T., Manu, N., Wu, W., Mannan, P., Garfield, S. H., et a!. (2016). A function-blocking CD47 antibody suppresses stem cell and EGF signaling in triple-negative breast cancer. Oncotarget.

Kim, J., Hwangbo, J., and Wong, P. K. (2011). p38 MAPK-Mediated Bmi-1 down-regulation and defective proliferation in ATM-deficient neural stem cells can be restored by Akt activation. PLoS One 6, e16615.

Kimbung, S., Markholm, I., Bjohle, J., Lekberg, T., von Wachenfeldt, A., Azavedo, E., Saracco, A., Hellstrom, M., Veerla, S., Paquet, E., et a!. (2018). Assessment of early response biomarkers in relation to long-term survival in patients with HER2-negative breast cancer receiving neoadjuvant chemotherapy plus bevacizumab: Results from the Phase II PROMIX trial. Int J Cancer 142, 618-628.

Kreso, A., van Galen, P., Pedley, N. M., Lima-Fernandes, E., Frelin, C., Davis, T., Cao, L., Baiazitov, R., Du, W., Sydorenko, N., et a!. (2014). Self-renewal as a therapeutic target in human colorectal cancer. Nature medicine 20, 29-36.

Li, B., and Dewey, C. N. (2011). RSEM: accurate transcript quantification from RNA-Seq data with or without a reference genome. BMC bioinformatics 12, 323.

Li, C., Wang, S., Xing, Z., Lin, A., Liang, K., Song, J., Hu, Q., Yao, J., Chen, Z., Park, P. K., et a!. (2017). A ROR1-HER3-lncRNA signalling axis modulates the Hippo-YAP pathway to regulate bone metastasis. Nature cell biology 19, 106-119.

Liberzon, A., Subramanian, A., Pinchback, R., Thorvaldsdottir, H., Tamayo, P., and Mesirov, J. P. (2011). Molecular signatures database (MSigDB) 3.0. Bioinformatics 27, 1739-1740.

Love, M. I., Huber, W., and Anders, S. (2014). Moderated estimation of fold change and dispersion for RNA-seq data with DESeq2. Genome biology 15, 550.

Marcel, M. (2011). Cutadapt removes adapter sequences from high-throughput sequencing reads. EMBnet J 17, 10-12.

Maugeri-Sacca, M., and De Maria, R. (2016). Hippo pathway and breast cancer stem cells. Critical reviews in oncology/hematology 99, 115-122.

McHenry, P. R., and Vargo-Gogola, T. (2010). Pleiotropic functions of Rho GTPase signaling: a Trojan horse or Achilles' heel for breast cancer treatment? Current drug targets 11, 1043-1058.

Mo, J. S., Park, H. W., and Guan, K. L. (2014). The Hippo signaling pathway in stem cell biology and cancer. EMBO reports 15, 642-656.

Moroishi, T., Hansen, C. G., and Guan, K. L. (2015). The emerging roles of YAP and TAZ in cancer. Nature reviews Cancer 15, 73-79.

Murga, C., Zohar, M., Teramoto, H., and Gutkind, J. S. (2002). Rac1 and RhoG promote cell survival by the activation of PI3K and Akt, independently of their ability to stimulate JNK and NF-kappaB. Oncogene 21, 207-216.

Nacerddine, K., Beaudry, J. B., Ginjala, V., Westerman, B., Mattiroli, F., Song, J. Y., van der Poel, H., Ponz, O. B., Pritchard, C., Cornelissen-Steijger, P., et a!. (2012). Akt-mediated phosphorylation of Bmi1 modulates its oncogenic potential, E3 ligase activity, and DNA damage repair activity in mouse prostate cancer. J Clin Invest 122, 1920-1932.

Ohgushi, M., Minaguchi, M., and Sasai, Y. (2015). Rho-Signaling-Directed YAP/TAZ Activity Underlies the Long-Term Survival and Expansion of Human Embryonic Stem Cells. Cell Stem Cell 17, 448-461.

Paranjape, A. N., Balaji, S. A., Mandal, T., Krushik, E. V., Nagaraj, P., Mukherjee, G., and Rangarajan, A. (2014). Bmi1 regulates self-renewal and epithelial to mesenchymal transition in breast cancer cells through Nanog. BMC Cancer 14, 785.

Park, H. W., Kim, Y. C., Yu, B., Moroishi, T., Mo, J. S., Plouffe, S. W., Meng, Z., Lin, K. C., Yu, F. X., Alexander, C. M., et a!. (2015). Alternative Wnt Signaling Activates YAP/TAZ. Cell 162, 780-794.

Ritchie, M. E., Phipson, B., Wu, D., Hu, Y., Law, C. W., Shi, W., and Smyth, G. K. (2015). limma powers differential expression analyses for RNA-sequencing and microarray studies. Nucleic acids research 43, e47.

Samanta, D., Gilkes, D. M., Chaturvedi, P., Xiang, L., and Semenza, G. L. (2014). Hypoxia-inducible factors are required for chemotherapy resistance of breast cancer stem cells. Proc Natl Acad Sci USA 111, E5429-5438.

Schaefer, C. F., Anthony, K., Krupa, S., Buchoff, J., Day, M., Hannay, T., and Buetow, K. H. (2009). PID: the Pathway Interaction Database. Nucleic Acids Res 37, D674-679.

Stickeler, E., Pils, D., Klar, M., Orlowsk-Volk, M., Zur Hausen, A., Jager, M., Watermann, D., Gitsch, G., Zeillinger, R., and Tempfer, C. B. (2011). Basal-like molecular subtype and HER4 up-regulation and response to neoadjuvant chemotherapy in breast cancer. Oncol Rep 26, 1037-1045.

Su, J., Wu, S., Tang, W., Qian, H., Zhou, H., and Guo, T. (2015). Reduced SLC27A2 induces cisplatin resistance in lung cancer stem cells by negatively regulating Bmi1-ABCG2 signaling. Molecular carcinogenesis.

Tamayo, P., Mootha, V. K., Mukherjee, S., Ebert, B. L., Gillette, M. A., Paulovich, A., Pomeroy, S. L., Golub, T. R., Lander, E. S., et a!. (2005). Gene set enrichment analysis: a knowledge-based approach for interpreting genome-wide expression profiles. Proc Natl Acad Sci USA 102, 15545-15550.

Tamm, C., Bower, N., and Anneren, C. (2011). Regulation of mouse embryonic stem cell self-renewal by a Yes-YAP-TEAD2 signaling pathway downstream of LIF. Journal of cell science 124, 1136-1144.

Voncken, J. W., Niessen, H., Neufeld, B., Rennefahrt, U., Dahlmans, V., Kubben, N., Holzer, B., Ludwig, S., and Rapp, U. R. (2005). MAPKAP kinase 3pK phosphorylates and regulates chromatin association of the polycomb group protein Bmi1. The Journal of biological chemistry 280, 5178-5187.

Wahl, G. M., and Spike, B. T. (2017). Cell state plasticity, stem cells, EMT, and the generation of intra-tumoral heterogeneity. NPJ Breast Cancer 3, 14.

Wang, A., Chen, L., Li, C., and Zhu, Y. (2015). Heterogeneity in cancer stem cells. Cancer letters 357, 63-68.

Wang, Y., Zhe, H., Ding, Z., Gao, P., Zhang, N., and Li, G. (2012). Cancer stem cell marker Bmi-1 expression is associated with basal-like phenotype and poor survival in breast cancer. World J Surg 36, 1189-1194.

Wiederschain, D., Chen, L., Johnson, B., Bettano, K., Jackson, D., Taraszka, J., Wang, Y. K., Jones, M. D., Morrissey, M., Deeds, J., et a!. (2007). Contribution of polycomb homologues Bmi-1 and Mel-18 to medulloblastoma pathogenesis. Molecular and cellular biology 27, 4968-4979.

Wu, X., Liu, X., Sengupta, J., Bu, Y., Yi, F., Wang, C., Shi, Y., Zhu, Y., Jiao, Q., and Song, F. (2011). Silencing of Bmi-1 gene by RNA interference enhances sensitivity to doxorubicin in breast cancer cells. Indian journal of experimental biology 49, 105-112.

Yates, A., Akanni, W., Amode, M. R., Barrell, D., Billis, K., Carvalho-Silva, D., Cummins, C., Clapham, P., Fitzgerald, S., Gil, L., et a!. (2016). Ensembl 2016. Nucleic acids research 44, D710-716.

Yu, J., Chen, L., Cui, B., Widhopf, G. F., 2nd, Shen, Z., Wu, R., Zhang, L., Zhang, S., Briggs, S. P., and Kipps, T. J. (2015). Wnt5a induces ROR1/ROR2 heterooligomerization to enhance leukemia chemotaxis and proliferation. J Clin Invest.

Yu, J., Chen, L., Cui, B., Widhopf, G. F., 2nd, Shen, Z., Wu, R., Zhang, L., Zhang, S., Briggs, S. P., and Kipps, T. J. (2016). Wnt5a induces ROR1/ROR2 heterooligomerization to enhance leukemia chemotaxis and proliferation. J Clin Invest 126, 585-598.

Zhang, S., Chen, L., Cui, B., Chuang, H. Y., Yu, J., Wang-Rodriguez, J., Tang, L., Chen, G., Basak, G. W., and Kipps, T. J. (2012a). ROR1 is expressed in human breast cancer and associated with enhanced tumor-cell growth. PLoS One 7, e31127.

Zhang, S., Chen, L., Wang-Rodriguez, J., Zhang, L., Cui, B., Frankel, W., Wu, R., and Kipps, T. J. (2012b). The onco-embryonic antigen ROR1 is expressed by a variety of human cancers. The American journal of pathology 181, 1903-1910.

Zhang, S., Cui, B., Lai, H., Liu, G., Ghia, E. M., Widhopf, G. F., 2nd, Zhang, Z., Wu, C. C., Chen, L., Wu, R., et a!. (2014). Ovarian cancer stem cells express ROR1, which can be targeted for anti-cancer-stem-cell therapy. Proc Natl Acad Sci USA 111, 17266-17271.

Informal Sequence Listing 99961.1 CDR H1 (SEQ ID NO:1): GYAFTAYN
99961.1 CDR H2 (SEQ ID NO:2): FDPYDGGS
99961.1 CDR H3 (SEQ ID NO:3): GWYYFDY
99961.1 CDR L1 (SEQ ID NO:4): KSISKY
99961.1 CDR L2 (SEQ ID NO:5): SGS
99961.1 CDR L3 (SEQ ID NO:6): QQHDESPY
D10 CDR H1 (SEQ ID NO:7): GFSLTSYG
D10 CDR H2 (SEQ ID NO:8): IWAGGFT
D10 CDR H3 (SEQ ID NO:9): RGSSYSMDY
D10 CDR L1 (SEQ ID NO:10): SNVSY
D10 CDR L2 (SEQ ID NO: 11): EIS
D10 CDR L3 (SEQ ID NO:12): QQWNYPLIT
GAPDH forward primer (SEQ ID NO:13): 5'-GAAGGTGAAGGTCGGAGTC-3'
GAPDH reverse primer (SEQ ID NO:14): 5'-GAAGATGGTGATGGGATTTC-3'
BMI1 forward primer (SEQ ID NO:15): 5'-CGTGTATTGTTCGTTACCTGGA-3'
BMI1 reverse primer (SEQ ID NO:16): 5'-TTCAGTAGTGGTCTGGTCTTGT-3'
CRISPR targeting sequence of ROR1 (SEQ ID NO:17): CCAGTGCGTGGCAACAAACGGCA

P EMBODIMENTS

P Embodiment 1. A method of treating cancer in a subject in need thereof, said method comprising administering to said subject a therapeutically effective amount of a mitotic inhibitor and a ROR-1 antagonist.

P Embodiment 2. A method of treating cancer in a patient with chemotherapy-resistant tumors, said method comprising administering to said subject a therapeutically effective amount of a mitotic inhibitor and a ROR-1 antagonist.

P Embodiment 3. A method of treating cancer in a subject in need thereof, said method comprising administering to said subject a therapeutically effective amount of a ROR-1 antibody, wherein said subject expresses an elevated level of ROR-1 relative to a standard control and wherein said subject has or is receiving chemotherapy.

P Embodiment 4. The method according to P embodiments 1-3, wherein said mitotic inhibitor is paclitaxel.

P Embodiment 5. The method according to P embodiments 1-3, wherein said ROR-1 antagonist is cirmtuzumab.

P Embodiment 6. The method according to P embodiments 1-3 wherein said cancer is breast cancer.

P Embodiment 7. A pharmaceutical composition comprising a pharmaceutically effective amount of a mitotic inhibitor and a ROR-1 antibody.

P Embodiment 8. The pharmaceutical composition of P embodiment 7, wherein said mitotic inhibitor and said ROR-1 antibody are present in a combined synergistic amount and wherein said combined synergistic amount is effective to treat cancer in a subject in need thereof.

EMBODIMENTS

Embodiment 1. A method of treating a chemoresistant cancer in a subject in need thereof, said method comprising administering to said subject a therapeutically effective amount of a chemotherapeutic agent and a therapeutically effective amount of a tyrosine kinase-like orphan receptor 1 (ROR-1) antagonist, thereby treating a chemoresistant cancer in said subject.

Embodiment 2. The method of embodiment 1, comprising prior to said administering detecting a level of ROR-1 in said subject.

Embodiment 3. The method of embodiment 1 or 2, wherein said subject is receiving or has received chemotherapy.

Embodiment 4. The method of any one of embodiments 1-3, wherein said chemoresistant cancer is a chemoresistant breast cancer.

Embodiment 5. The method of any one of embodiments 1-4, further comprising prior to said administering selecting a subject expressing an increased level of ROR-1 relative to a standard control.

Embodiment 6. The method of any one of embodiments 1-5, wherein said chemotherapeutic agent is a plant alkaloid, an antitumor antibiotic or a topoisomerase inhibitor.

Embodiment 7. The method of any one of embodiments 1-6, wherein said chemotherapeutic agent is paclitaxel or docetaxel.

Embodiment 8. The method of any one of embodiments 1-6, wherein said chemotherapeutic agent is doxorubicin or epirubicin.

Embodiment 9. The method of any one of embodiments 1-8, wherein said ROR-1 antagonist is an antibody or a small molecule.

Embodiment 10. The method of any one of embodiments 1-9, wherein said ROR-1 antagonist is an anti-ROR-1 antibody.

Embodiment 11. The method of embodiment 10, wherein said antibody comprises a humanized heavy chain variable region and a humanized light chain variable region, wherein said humanized heavy chain variable region comprises the sequences set forth in SEQ ID NO:1, SEQ ID NO:2, and SEQ ID NO:3; and wherein said humanized light chain variable region comprises the sequences set forth in SEQ ID NO:4, SEQ ID NO:5, and SEQ ID NO:6.

Embodiment 12. The method of embodiment 10 or 11, wherein said antibody is cirmtuzumab.

Embodiment 13. The method of embodiment 10, wherein said antibody comprises a humanized heavy chain variable region and a humanized light chain variable region, wherein said humanized heavy chain variable region comprises the sequences set forth in SEQ ID NO:7, SEQ ID NO:8, and SEQ ID NO:9; and wherein said humanized light chain variable region comprises the sequences set forth in SEQ ID NO:10, SEQ ID NO:11, and SEQ ID NO:12.

Embodiment 14. The method of any one of embodiments 1-13, wherein said chemotherapeutic agent and said ROR-1 antagonist are administered in a combined synergistic amount.

Embodiment 15. The method of any one of embodiments 1-14, wherein said chemotherapeutic agent and said Embodiment 16. The method of any one of embodiments 1-15, wherein said ROR-1 antagonist is administered at a first time point and said chemotherapeutic agent is administered at a second time point, wherein said first time point precedes said second time point.

Embodiment 17. The method of any one of embodiments 1-16, wherein said chemotherapeutic agent and said ROR-1 antagonist are admixed prior to administration.

Embodiment 18. The method of any one of embodiments 1-17, wherein said chemotherapeutic agent is paclitaxel.

Embodiment 19. The method of any one of embodiments 1-18, wherein said chemotherapeutic agent is administered at an amount of about 5 mg/kg, 10 mg/kg, 11 mg/kg, 12 mg/kg, 13 mg/kg, 14 mg/kg or 15 mg/kg.

Embodiment 20. The method of any one of embodiments 1-19, wherein said chemotherapeutic agent is administered at an amount of about 13 mg/kg.

Embodiment 21. The method of any one of embodiments 1-20, wherein said chemotherapeutic agent is administered at an amount of 13.4 mg/kg.

Embodiment 22. The method of any one of embodiments 1-21, wherein said ROR-1 antagonist is administered at an amount of about 1 mg/kg, 2 mg/kg, 3 mg/kg, 5 mg/kg or 10 mg/kg.

Embodiment 23. The method of any one of embodiments 1-22, wherein said ROR-1 antagonist is administered at an amount of about 2 mg/kg.

Embodiment 24. The method of any one of embodiments 1-23, wherein said chemotherapeutic agent is administered at an amount of 13.4 mg/kg and said ROR-1 antagonist is administered at about 2 mg/kg.

Embodiment 25. The method of any one of embodiments 1-24, wherein said chemotherapeutic agent is administered daily over the course of at least 14 days.

Embodiment 26. The method of any one of embodiments 1-25, wherein said chemotherapeutic agent is administered daily over the course of about 28 days.

Embodiment 27. The method of any one of embodiments 1-26, wherein said ROR-1 antagonist is administered once over the course of about 28 days.

Embodiment 28. The method of any one of embodiments 1-27, wherein said chemotherapeutic agent is administered intravenously.

Embodiment 29. The method of any one of embodiments 1-28, wherein said ROR-1 antagonist is administered intravenously.

Embodiment 30. The method of any one of embodiments 1-29, wherein said subject is a mammal.

Embodiment 31. The method of any one of embodiments 1-30, wherein said subject is a human.

Embodiment 32. A method of treating breast cancer in a subject in need thereof, said method comprising administering to said subject a therapeutically effective amount of a chemotherapeutic agent and a therapeutically effective amount of a tyrosine kinase-like orphan receptor 1 (ROR-1) antagonist, thereby treating a chemoresistant breast cancer in said subject.

Embodiment 33. A pharmaceutical composition comprising (i) a chemotherapeutic agent selected from the group consisting of plant alkaloid, an antitumor antibiotic and a topoisomerase inhibitor, (ii) a ROR-1 antagonist and (iii) a pharmaceutically acceptable excipient.

Embodiment 34. A pharmaceutical composition comprising (i) a chemotherapeutic agent selected from the group consisting of a plant alkaloid, an antitumor antibiotic and a topoisomerase inhibitor, (ii) an anti-ROR-1 antibody and (iii) a pharmaceutically acceptable excipient, wherein said chemotherapeutic agent and said anti-ROR-1 antibody are present in a combined synergistic amount, wherein said combined synergistic amount is effective to treat breast cancer in a subject in need thereof.

Embodiment 35. The pharmaceutical composition of embodiment 33 or 34, wherein said chemotherapeutic agent is a plant alkaloid.

Embodiment 36. The pharmaceutical composition of any one of embodiments 33-35, wherein said chemotherapeutic agent paclitaxel.

Embodiment 37. The pharmaceutical composition of any one of embodiments 33-36, wherein said ROR-1 antagonist is an antibody or a small molecule.

Embodiment 38. The pharmaceutical composition of any one of embodiments 33-37, wherein said ROR-1 antagonist is an anti-ROR-1 antibody.

Embodiment 39. The pharmaceutical composition of embodiment 38, wherein said antibody comprises a humanized heavy chain variable region and a humanized light chain variable region, wherein said humanized heavy chain variable region comprises the sequences set forth in SEQ ID NO:1, SEQ ID NO:2, and SEQ ID NO:3; and wherein said humanized light chain variable region comprises the sequences set forth in SEQ ID NO:4, SEQ ID NO:5, and SEQ ID NO:6.

Embodiment 40. The pharmaceutical composition of embodiment 38, wherein said antibody is cirmtuzumab.

What is claimed is:

1. A method of treating a chemoresistant cancer in a subject in need thereof, said method comprising administering to said subject a therapeutically effective amount of paclitaxel or docetaxel and a therapeutically effective amount of a tyrosine kinase-like orphan receptor 1 (ROR-1) antagonist antibody, thereby treating the chemoresistant cancer in said subject, wherein the chemoresistant cancer is paclitaxel resistant or docetaxel resistant and is Her2 negative, wherein said subject is receiving or has received chemotherapy, and
   wherein said antibody comprises a humanized heavy chain variable region and a humanized light chain variable region, wherein said humanized heavy chain variable region comprises the sequences set forth in SEQ ID NO:1, SEQ ID NO:2, and SEQ ID NO:3; and wherein said humanized light chain variable region comprises the sequences set forth in SEQ ID NO:4, SEQ ID NO:5, and SEQ ID NO:6.

2. The method of claim 1, comprising prior to said administering detecting a level of ROR-1 in said subject.

3. The method of claim 1, wherein said chemoresistant cancer is a chemoresistant breast cancer.

4. The method of claim 1, wherein said antibody is cirmtuzumab.

5. The method of claim 1, wherein said paclitaxel or docetaxel and said ROR-1 antagonist antibody are administered simultaneously or sequentially.

6. The method of claim 1, wherein said ROR-1 antagonist antibody is administered at a first time point and said paclitaxel or docetaxel is administered at a second time point, wherein said first time point precedes said second time point.

7. The method of claim 1, wherein said paclitaxel or docetaxel and said ROR-1 antagonist antibody are admixed prior to administration.

8. The method of claim 1, wherein said method comprises administering to said subject a therapeutically effective amount of paclitaxel.

9. The method of claim 1, wherein said paclitaxel or docetaxel is administered at an amount from about 5 mg/kg to about 15 mg/kg.

10. The method of claim 1, wherein said ROR-1 antagonist antibody is administered at an amount from about 1 mg/kg to about 10 mg/kg.

11. The method of claim 1, wherein said ROR-1 antagonist antibody is administered intravenously.

12. The method of claim 1, wherein said subject is a human.

13. The method of claim 1, wherein the cancer is breast cancer, ovarian cancer, prostate cancer, pancreatic cancer, adrenal cancer, lung cancer, testicular cancer, or colon cancer.

14. The method of claim 1, wherein the cancer is breast cancer.

15. The method of claim 1, wherein the cancer is prostate cancer.

* * * * *